United States Patent
Li et al.

(10) Patent No.: US 8,846,693 B2
(45) Date of Patent: Sep. 30, 2014

(54) OPTIONALLY SUBSTITUTED PYRAZOLO[3,4-D]PYRIMIDINE-4,6-DIONES

(75) Inventors: Peng Li, New York, NY (US); Jun Zhao, New York, NY (US); Hailin Zheng, New York, NY (US)

(73) Assignee: Intra-Cellular Therapies, Inc., New York, NY (US)

( * ) Notice: Subject to any disclaimer, the term of this patent is extended or adjusted under 35 U.S.C. 154(b) by 569 days.

(21) Appl. No.: 12/746,231

(22) PCT Filed: Dec. 6, 2008

(86) PCT No.: PCT/US2008/013410
§ 371 (c)(1),
(2), (4) Date: Jun. 4, 2010

(87) PCT Pub. No.: WO2009/073210
PCT Pub. Date: Jun. 11, 2009

(65) Prior Publication Data
US 2010/0273753 A1    Oct. 28, 2010

Related U.S. Application Data

(60) Provisional application No. 61/012,045, filed on Dec. 6, 2007.

(51) Int. Cl.
| | |
|---|---|
| C07D 487/04 | (2006.01) |
| A61K 31/519 | (2006.01) |
| A61P 25/24 | (2006.01) |
| A61P 25/22 | (2006.01) |
| A61P 15/10 | (2006.01) |
| A61P 9/12 | (2006.01) |

(52) U.S. Cl.
CPC .................................. C07D 487/04 (2013.01)
USPC ....................................... 514/262.1; 544/262

(58) Field of Classification Search
CPC .......................... C07D 487/04; A61K 31/519
USPC ....................................... 544/262; 514/262.1
See application file for complete search history.

(56) References Cited

U.S. PATENT DOCUMENTS

| | | | |
|---|---|---|---|
| 3,689,863 A | 9/1972 | Matsuoka et al. |
| 3,993,650 A | 11/1976 | Tarzia et al. |
| 4,663,326 A | 5/1987 | Hamilton |
| 4,824,848 A | 4/1989 | Naka et al. |
| 5,202,328 A | 4/1993 | De Laszlo et al. |
| 5,223,501 A | 6/1993 | Chakravarty et al. |
| 5,294,612 A | 3/1994 | Bacon et al. |
| 5,393,755 A | 2/1995 | Neustadt et al. |
| 5,409,934 A | 4/1995 | Smith et al. |
| 5,719,283 A | 2/1998 | Bell et al. |
| 5,939,419 A | 8/1999 | Tulshian |
| 6,133,273 A | 10/2000 | Gilbert et al. |
| 6,166,019 A | 12/2000 | Meyer et al. |
| 6,235,742 B1 | 5/2001 | Bell et al. |
| 6,423,716 B1 | 7/2002 | Matsuno et al. |
| 6,492,371 B2 | 12/2002 | Roylance |
| 6,498,165 B1 | 12/2002 | Armstrong et al. |
| 6,756,373 B1 | 6/2004 | Allerton et al. |
| 7,153,824 B2 | 12/2006 | Palmer et al. |
| 7,157,451 B2 | 1/2007 | Atwal et al. |
| 8,273,750 B2 | 9/2012 | Li et al. |
| 8,273,751 B2 | 9/2012 | Li et al. |
| 2003/0092908 A1 | 5/2003 | Pitts et al. |
| 2003/0162782 A1 | 8/2003 | Grossman et al. |
| 2004/0254183 A1 | 12/2004 | Basarab et al. |
| 2005/0048573 A1 | 3/2005 | Artis et al. |
| 2005/0075795 A1 | 4/2005 | Pandit |
| 2005/0113379 A1 | 5/2005 | Ge et al. |
| 2006/0160831 A1 | 7/2006 | Tsutsumi et al. |
| 2006/0252790 A1 | 11/2006 | Allen et al. |
| 2007/0208029 A1 | 9/2007 | Barlow et al. |
| 2008/0176961 A1 | 7/2008 | Greengard et al. |
| 2008/0194592 A1 | 8/2008 | Mates et al. |
| 2009/0137549 A1 | 5/2009 | Edward et al. |
| 2010/0087450 A1 | 4/2010 | Mates et al. |
| 2010/0173878 A1 | 7/2010 | Li et al. |
| 2010/0323997 A1 | 12/2010 | Fienberg et al. |
| 2011/0237561 A1 | 9/2011 | Li et al. |
| 2011/0245214 A1 | 10/2011 | Li et al. |
| 2011/0281832 A1 | 11/2011 | Li et al. |

(Continued)

FOREIGN PATENT DOCUMENTS

| | | |
|---|---|---|
| DE | 197 09 126 | 3/1997 |
| DE | 199 31 206 | 1/2001 |

(Continued)

OTHER PUBLICATIONS

Medina et al. "Therapeutic Utility of Phosphodiesterase Type I Inhibitors in Neurological Conditions," (Front. Neurosci., 2011, 5(21), pp. 1-5).*
U.S. Appl. No. 13/500,941, filed Apr. 9, 2012, Li et al.
Ahn, H. et al., "Potent Tetracyclic Guanine Inhibitors of PDE1 and PDE5 Cyclic Guanosine Monophosphate Phosphodiesterases with Oral Antihypertensive Activity", J. Med. Chem., 1997, 40(14), pp. 2196-2210.
Al-Afaleq, E., et al., "Heterocyclic o-Aminonitriles: Preparation of Pyrazolo[3,4-d]-pyrimidines with Modification of the substituents at the 1-position", Molecules, 6, pp. 621-638, (2001).
Banker, G.S. et al, "Modern Pharmaceutics, 3ed.", Marcel Dekker, New York, 1996, p. 596.
Bender et al; "Cyclic Nucleotide Phosphodiesterases: Molecular Regulation to Clinical Use", Pharmcol. Rev., 2006, 58, pp. 488-520.
Fienberg et al; "DARPP-32: Regulator of the Efficacy of Dopaminergic Neurotransmission", Science, (1998) 281, pp. 838-842.

(Continued)

Primary Examiner — Susanna Moore
(74) Attorney, Agent, or Firm — Hoxie & Associates, LLC

(57) ABSTRACT

1- or 2- or 7-(substituted)-3-(optionally hetero)arylamino-[1H,2H]-pyrazolo[3,4-d]pyrimidine-4,6(5H,7H)-dione derivatives, in free, salt or prodrug form, are useful as pharmaceuticals, particularly as phosphodiesterase 1 inhibitors, useful for the treatment of diseases involving disorders of the dopamine D1 receptor intracellular pathway, such as Parkinson's disease, depression, narcolepsy and damage to cognitive function, e.g., in schizophrenia or disorders that may be ameliorated through enhanced progesterone-signaling pathway, e.g., female sexual dysfunction.

20 Claims, No Drawings

(56) References Cited

U.S. PATENT DOCUMENTS

| | | |
|---|---|---|
| 2011/0312978 A1 | 12/2011 | Davis et al. |
| 2012/0053190 A1 | 3/2012 | Fienberg et al. |
| 2012/0071450 A1 | 3/2012 | Li et al. |
| 2012/0094966 A1 | 4/2012 | Li et al. |
| 2012/0136013 A1 | 5/2012 | Li et al. |
| 2012/0201754 A1 | 8/2012 | Li et al. |
| 2013/0085123 A1 | 4/2013 | Li et al. |

FOREIGN PATENT DOCUMENTS

| | | |
|---|---|---|
| EP | 0 063 381 | 10/1982 |
| EP | 0 166 054 | 1/1986 |
| EP | 0 201 188 | 12/1986 |
| EP | 0 237 289 | 9/1987 |
| EP | 0 306 185 | 8/1988 |
| EP | 0 353 941 | 7/1989 |
| EP | 0 383 465 | 2/1990 |
| EP | 0636626 | 2/1995 |
| EP | 0 911 333 | 4/1999 |
| EP | 1 097 706 | 11/2000 |
| EP | 1852108 | 11/2007 |
| JP | 53031694 | 3/1978 |
| JP | 63-010788 | 1/1988 |
| JP | 01265027 | 4/1988 |
| JP | 02289518 | 11/1990 |
| JP | 2006-527202 | 11/2006 |
| KR | 10-1991-0006866 | 9/1991 |
| NL | 1 186 466 | 7/1962 |
| WO | WO 91/19717 | 12/1991 |
| WO | WO 96/28429 | 9/1996 |
| WO | WO 97/05138 | 2/1997 |
| WO | WO 97/30710 | 8/1997 |
| WO | WO 98/28301 | 7/1998 |
| WO | WO 98/46606 | 10/1998 |
| WO | WO 98/52568 | 11/1998 |
| WO | WO 01/27113 | 4/2001 |
| WO | WO 02/074312 | 9/2002 |
| WO | WO 03/002567 | 1/2003 |
| WO | WO 03/020702 | 3/2003 |
| WO | WO 03/020724 | 3/2003 |
| WO | WO 03/037899 | 5/2003 |
| WO | WO 2004/018474 | 3/2004 |
| WO | WO 2004/056831 | 7/2004 |
| WO | WO 2004/087906 | 10/2004 |
| WO | WO 2007/025103 | 3/2007 |
| WO | WO 2007/031977 | 3/2007 |
| WO | WO 2007/143568 | 12/2007 |
| WO | WO 2006/133261 | 12/2008 |
| WO | WO 2009/022007 | 2/2009 |
| WO | WO 2009/131974 | 10/2009 |
| WO | WO 2011/153129 | 12/2011 |
| WO | WO 2011/153135 | 12/2011 |
| WO | WO 2011/153136 | 12/2011 |
| WO | WO 2011/153138 | 12/2011 |
| WO | WO 2012/171016 | 12/2012 |

OTHER PUBLICATIONS

Gilbert, A., et al., "Pyrazolopyrimidine-2,4-dione Sulfonamides: Novel and Selective Calcitonin Inducers," *J. Med. Chem.*, (2002), 45: pp. 2342-2345.
Greengard, P. et al., "Beyond the Dopamine Receptor: the DARPP-32/Protein Phosphatase-1 Cascade", Neuron, 1999, 23, pp. 435, 447.
Lugnier et al. (Pharmacology & Therapeutics, 2006, 109, pp. 306-398).
Lundqvist et al, *Nature* (2007) 447:817-822.
Mani, S.K. et al., "Requirement for DARPP-32 in Progesterone-Facilitated Sexual Receptivity in Female Rats and Mice", Science, 2000, 287, pp. 1053-1056.
Medina (Frontiers in Neuroscience, 2011, 5, pp. 21).
Morgan (Expert Opinion, 2006, 11(3), 403-417).
Murray, F. et al., "Expression and activity of cAMP phosphodiesterase isoforms in pulmonary artery smooth muscle cells from patients with pulmonary hypertension: role for PDE1", Am. J. Physiol. Lung Cell Mol. Physiol., 2007, 292, pp. L294-L303.
Nishi et al, *J Neurosci* (1997) 17:8147-8155.
Noguchi, M., et al., "A Facile Preparation of 7-(Substituted amino)-6 H-pyrrolo[3,7-d]-pyrimidine Derivatives1)", Bulletin of The Chemical Society of Japan, vol. 62, pp. 3043-3045, (Jan. 1, 1989).
Poulsen et al, *Bioorg & Med Chem Letter* (2001) 11:191-193.
Reed, T.M. et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning", The Journal of Neuroscience, 2002, 22(12), pp. 5188-5197.
Rybalkin, S.D. et al., "Cyclic GMP Phosphodiesterases and Regulation of Smooth Muscle Function", Circ. Res., 2003, 93, pp. 280-291.
Turko et al, *Mol Pharmacol* (1999) 56:124-130.
Wolff, M. E., "Burger's Medicinal Chemistry, 5ed, Part I", John Wiley & Sons, 1995, pp. 975-977.
Xia, Y. et al., Synthesis and Evaluation of Polycyclic Pyrazolo[34-d]pyrimidines as PDE1 and PDE5 cGMP Phosphodiesterase Inhibitors, Journal Medicinal Chemistry, 1997, 40, pp. 4372-4377.
U.S. Appl. No. 13/701,225, filed Mar. 2013, Li et al.
U.S. Appl. No. 13/701,284, filed Mar. 2013, Li et al.
U.S. Appl. No. 13/701,244, filed Apr. 2013, Li et al.
Gelbin, et al., "Ketene-S, N-acetals as synthons for heterocycles new synthesis of pyrimidinones", *Journal Fuer Praktische Chemie*, vol. 329, No. 5, pp. 753-766, (1987).
Goodman & Gilman, The Pharmacological Basis of Therapeutics, McGraw-Hill Interamericana. 2007, p. 892. (cited within text of Office Action from corresponding Costa Rican application, attached herein).
Park, et al., "Traumatic Brain Injury: Can the consequences be stopped?" CMAJ, 178(9), 1163-1170, (2008).
Tominaga et al. "Synthesis of pyrazolo [3,4-d]pyrimidine derivatives using ketene dithioacetals" *Journal of Heterocyclic Chemistry*, 27(3), 775-783 (1990).
Office Actions for U.S. Appl. No. 12/303,618, filed Dec. 5, 2008.
Boyd et al., "Dopamine Receptor Signaling and Current and Future Antipsychotic Drugs", *Current Antipsychotics, Handbook of Experimental Pharmacology*, 212:53-86, (2012) doi: 10.1007/978-3-642-25761-2_3.
Ehrman et al., Phosphodiesterase 1B Differentially Modulates The Effects Of Methamphetamine On Locomotor Activity And Spatial Learning Through DARPP32-Dependent Pathways: Evidence from PDE1B-DARPP32 Double-Knockout Mice, *Genes, Brain and Behavior*, 5:540-551 (2006).
Fienberg, "The DARPP-32 Knockout Mouse", *Brain Res. Rev.* 3:313-319 (2000).
Gilbert, A.M et al., "Novel and Selective Calcitonin-Inducing Agents", Journal of Medicinal Chemistry, vol. 43, No. 6, p. 1223-1233 (2000).
Girault et al., "The Neurobiology of Dopamine Signaling", *Arch Neurol*, 61(5):641-4 (2004).
Kakkar, et al., "Inhibition of Bovine Brain Calmodulin-Dependent Cyclic Nucleotide Phosphodiesterase Isozymes by Deprenyl", *Life Sciences*, 59(21):337-341 (1996).
Kakkar, et al. "Amantadine: an antiparkinsonian agent inhibits bovine brain 60 kDa calmodulin-dependent cyclic nucleotide phosphodiesterase isozyme", Brain Res. 749(2):290-294 (1997).
Kakkar, et al. "Calmodulin-dependent cyclic nucleotide phosphodiesterase (PDE1)" *Cell Mol Life Sci.* 55(8-9):1164-1186 (1999).
Keravis et al., "Cyclic Nucleotide Phsophodiesterase (ODE) Isozymes as Tagrets of the Intracellular Signalling Network: Benefits of PDE Inhibitors in Various Diseases and Perspectives for Future Therapeutic Developments", *British Journal of Pharmacology*, 165: 1288-1305 (2012).
Registry No. 353484-98-7, Registry (STN) [on-line], Entered STN: Aug. 29, 2001, Retrieved on Jan. 31, 2014.

\* cited by examiner

OPTIONALLY SUBSTITUTED PYRAZOLO[3,4-D]PYRIMIDINE-4,6-DIONES

CROSS REFERENCE TO RELATED APPLICATIONS

This application is a United States National Stage Application under 35 USC §371 of PCT/US2008/013410, filed Dec. 6, 2008, which claims priority from U.S. Provisional application No. 61/012,045, filed Dec. 6, 2007, the contents of each of which are hereby incorporated by reference.

STATEMENT REGARDING GOVERNMENT FUNDING

This invention was made, in part, with government support under Grant. No. 2R44MH067488 awarded by NIMH and Grant No. DAMD-17-03-1-0396 awarded by USAMRMC. The government has certain rights in the invention.

TECHNICAL FIELD

The present invention relates to novel 1- or 2- or 7-(substituted)-3-(optionally hetero)arylamino-[1H,2H]-pyrazolo[3,4-d]pyrimidine-4,6(5H,7H)-dione derivative compounds, processes for their production, their use as pharmaceuticals and pharmaceutical compositions comprising them. Of particular interest are novel compounds useful as inhibitors of phosphodiesterase 1 (PDE1), e.g., in the treatment of diseases involving disorders of the dopamine D1 receptor intracellular pathway, such as Parkinson's disease, depression, narcolepsy and damage to cognitive function, e.g., in schizophrenia or disorders that may be ameliorated through enhanced progesterone-signaling pathway, e.g., female sexual dysfunction.

BACKGROUND OF THE INVENTION

Eleven families of phosphodiesterases (PDEs) have been identified but only PDEs in Family I, the $Ca^{2+}$-calmodulin-dependent phosphodiesterases (CaM-PDEs), have been shown to mediate both the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a low level in the striatum. PDE1A is also expressed in the lung and heart. PDE1B is predominately expressed in the striatum, dentate gyrus, olfactory tract and cerebellum, and its expression correlates with brain regions having high levels of dopaminergic innervation. Although PDE1B is primarily expressed in the central nervous system, it may be detected in the heart. PDE1C is primarily expressed in olfactory epithelium, cerebellar granule cells, and striatum. PDE1C is also expressed in the heart and vascular smooth muscle.

Cyclic nucleotide phosphodiesterases decrease intracellular cAMP and cGMP signaling by hydrolyzing these cyclic nucleotides to their respective inactive 5'-monophosphates (5'AMP and 5'GMP). CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of nucleotide cyclases, resulting in increased cAMP and cGMP. These cyclic nucleotides in turn activate protein kinase A (PKA; cAMP-dependent protein kinase) and/or protein kinase G (PKG; cGMP-dependent protein kinase) that phosphorylate downstream signal transduction pathway elements such as DARPP-32 (dopamine and cAMP-regulated phosphoprotein) and cAMP responsive element binding protein (CREB). Phosphorylated DARPP-32 in turn inhibits the activity of protein phosphates-1 (PP-1), thereby increasing the state of phosphorylation of substrate proteins such as progesterone receptor (PR), leading to induction of physiologic responses. Studies in rodents have suggested that inducing cAMP and cGMP synthesis through activation of dopamine D1 or progesterone receptor enhances progesterone signaling associated with various physiological responses, including the lordosis response associated with receptivity to mating in some rodents. See Mani, et al., Science (2000) 287: 1053, the contents of which are incorporated herein by reference.

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), DARPP-32, and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), endorphin intracellular signaling pathway and progesterone signaling pathway. For example, inhibition of PDE1B should act to potentiate the effect of a dopamine D1 agonist by protecting cGMP and cAMP from degradation, and should similarly inhibit dopamine D2 receptor signaling pathways, by inhibiting PDE1 activity. Chronic elevation in intracellular calcium levels is linked to cell death in numerous disorders, particularly in neurodegenerative diseases such as Alzheimer's, Parkinson's and Huntington's Diseases and in disorders of the circulatory system leading to stroke and myocardial infarction. PDE1 inhibitors are therefore potentially useful in diseases characterized by reduced dopamine D1 receptor signaling activity, such as Parkinson's disease, restless leg syndrome, depression, narcolepsy and cognitive impairment. PDE1 inhibitors are also useful in diseases that may be alleviated by the enhancement of progesterone-signaling such as female sexual dysfunction.

There is thus a need for compounds that selectively inhibit PDE1 activity, especially PDE1B activity.

SUMMARY OF THE INVENTION

The invention provides novel compounds are surprisingly found to selectively inhibit phosphodiesterase 1 (PDE1) activity, e.g., PDE1A, PDE1B, and PDE1C activity, especially PDE1B activity.

In one embodiment, the Compounds of the Invention are pyrazolo[3,4-d]pyrimidine-4,6(5H,7H)-dione derivatives of formula Q

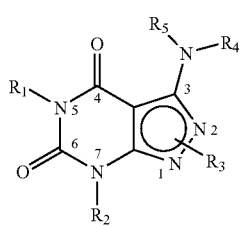

Formula Q wherein
(i) R₁ is H or C₁₋₆alkyl (e.g., methyl);
(ii) R₂ is
H,
C₁₋₆alkyl (e.g., isopropyl, isobutyl, 2-methylbutyl, 2,2-dimethyl propyl),
C₃₋₈cycloalkyl (e.g., cyclopentyl, cyclohexyl) optionally substituted with one or more amino (e.g., —NH₂), for example, 2-aminocyclopentyl or 2-aminocyclohexyl),
C₃₋₈heterocycloalkyl (e.g., pyrrolidinyl, for example, pyrrolidin-3-yl) optionally substituted with C₁₋₆alkyl (e.g., methyl), for example, 1-methylpyrrolidin-3-yl,
C₃₋₈cycloalkyl-C₁₋₆alkyl (e.g., cyclopropylmethyl),
C₁₋₆haloalkyl (e.g., trifluoromethyl, 2,2,2-trifluoroethyl),
C₀₋₆alkylaminoC₀₋₆alkyl (e.g., 2-(dimethylamino)ethyl, 2-aminopropyl),
hydroxyC₁₋₆alkyl (e.g., 3-hydroxy-2-methylpropyl),
arylC₀₋₆alkyl (e.g., benzyl),
heteroarylalkyl (e.g., pyridylmethyl),
C₁₋₆alkoxyarylC₁₋₆alkyl (e.g., 4-methoxybenzyl), or
-G-J wherein:
G is a single bond or, alkylene (e.g., methylene);
J is cycloalkyl or heterocycloalkyl (e.g., oxetan-2-yl, pyrolyin-3-yl, pyrolyin-2-yl) optionally substituted with alkyl (e.g., (1-methylpyrrolidin-2-yl));
(iii) R₃ is
a) D-E-F wherein
1. D is single bond, C₁₋₆alkylene (e.g., methylene), or arylC₁₋₆alkylene (e.g., benzylene or —CH₂C₆H₄—);
2. E is a C₁₋₆alkylene (e.g., methylene, ethynylene, prop-2-yn-1-ylene), arylene (e.g., phenylene or —C₆H₄—), C₁₋₆alkylarylene (e.g., -benzylene- or —CH₂C₆H₄—), aminoC₁₋₆alkylene (e.g., —CH₂N(H)—) or amino (e.g., —N(H)—); and
3. F is
C₁₋₆alkyl (e.g., isobutyl, isopropyl),
aryl (e.g., phenyl),
heteroaryl (e.g., 1,2,4-triazolyl, imidazolyl, pyridyl) optionally substituted with C₁₋₆alkyl, for example, pyrid-2-yl, imidazol-1-yl, 4-methylimidazolyl, 1-methylimidazol-2-yl, 1,2,4-triazol-1-yl,
heteroC₃₋₈cycloalkyl (e.g., piperidinyl, pyrrolidinyl) optionally substituted with C₁₋₆alkyl (e.g., methyl), for example, pyrrolidin-1-yl, pyrrolidin-2-yl, 1-methylpyrrolidin-2-yl, piperidin-2-yl, 1-methylpiperidin-2-yl, 1-ethylpiperidin-2-yl,
amino (e.g., —NH₂),
C₁₋₆alkoxy, or
—O-haloC₁₋₆alkyl (e.g., —O—CF₃), b) R₃ is a substituted heteroarylalkyl, e.g., substituted with C₁₋₆haloalkyl; or
c) R₃ is attached to one of the nitrogen atoms on the pyrazolo portion of Formula Q and is a moiety of Formula A

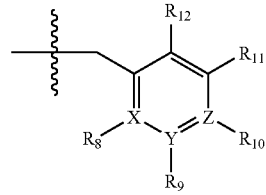

Formula A wherein X, Y and Z are, independently, N or C, and R₈, R₉, R₁₁ and R₁₂ are independently H or halogen (e.g., Cl or F); and R₁₀ is halogen, C₁₋₆alkyl, C₃₋₈cycloalkyl, C₁₋₆haloalkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), C₁₋₆alkoxadiazolyl (e.g., 5-methyl-1,2,4-oxadiazol), pyrazolyl (e.g., pyrazol-1-yl), C₁₋₆alkyl sulfonyl (e.g., methyl sulfonyl), arylcarbonyl (e.g., benzoyl), or heteroarylcarbonyl, C₁₋₆alkoxycarbonyl, (e.g., methoxycarbonyl), aminocarbonyl; preferably phenyl or pyridyl, e.g., 2-pyridyl; provided that when X, Y or X is nitrogen, R₈, R₉ or R₁₀, respectively, is not present;
(iv) R₄ is aryl (e.g., phenyl) optionally substituted with one or more halo (e.g., F or Cl), hydroxy or C₁₋₆alkoxy, heteroaryl (e.g., pyrid-4-yl, pyrid-2-yl or pyrazol-3-yl) or heteroC₃₋₆cycloalkyl (e.g., pyrrolidin-3-yl); and
(v) R₅ is H, C₁₋₆alkyl, C₃₋₈cycloalkyl (e.g., cyclopentyl), heteroaryl, aryl, p-benzylaryl (e.g., biphenyl-4-ylmethyl);
wherein "alk", "alkyl", "haloalkyl" or "alkoxy" refers to C₁₋₆ alkyl and "cycloalkyl" refers to C₃₋₈cycloalkyl;
in free, salt or prodrug form.
The invention further provides compounds of Formula Q as follows:
1.1. Formula Q wherein, R₁ is H or C₁₋₆alkyl (e.g., methyl);
1.2. Formula Q wherein, R₁ is C₁₋₆alkyl (e.g., methyl);
1.3. Formula Q wherein, R₁ is methyl;
Formula Q or any of 1.1-1.3 wherein, R₂ is H; C₁₋₆alkyl (e.g., isopropyl, isobutyl, 2-methylbutyl, 2,2-dimethyl propyl); C₃₋₈cycloalkyl (e.g., cyclopentyl, cyclohexyl) optionally substituted with one or more amino (e.g., —NH₂), for example, 2-aminocyclopentyl or 2-aminocyclohexyl); C₃₋₈heterocycloalkyl (e.g., pyrrolidinyl, for example, pyrrolidin-3-yl) optionally substituted with C₁₋₆alkyl (e.g., methyl), for example, 1-methylpyrrolidin-3-yl; C₃₋₈cycloalkyl-C₁₋₆alkyl (e.g., cyclopropylmethyl); haloC₁₋₆alkyl (e.g., trifluoromethyl, 2,2,2-trifluoroethyl); C₀₋₆alkylaminoC₀₋₆alkyl (e.g., 2-(dimethylamino)ethyl, 2-aminopropyl), hydroxyC₁₋₆alkyl (e.g., 3-hydroxy-2-methylpropyl); arylC₀₋₆alkyl (e.g., benzyl), heteroarylalkyl (e.g., pyridylmethyl), or alkoxyarylalkyl (e.g., 4-methoxybenzyl); or -G-J wherein: G is a single bond or, alkylene (e.g., methylene) and J is cycloalkyl or heterocycloalkyl (e.g., oxetan-2-yl, pyrolyin-3-yl, pyrolyin-2-yl) optionally substituted with alkyl (e.g., (1-methylpyrrolidin-2-yl));
1.4. Formula Q or any of 1.1-0, wherein $R_2$ is H,
1.5. Formula Q or any of 1.1-0, wherein $R_2$ is $C_{1-6}$ alkyl;
1.6. Formula 1.5 wherein, $R_2$ is isopropyl, isobutyl, 2,2-dimethylpropyl, or 2-methylbutyl;
1.7. Formula 1.5 wherein, $R_2$ is isobutyl;
1.8. Formula 1.5 wherein, $R_2$ is 2,2-dimethylpropyl;
1.9. Formula Q or any of 1.1-1.5, wherein $R_2$ is hydroxy$C_{1-6}$ alkyl;
1.10. Formula 1.9, wherein $R_2$ is 3-hydroxy-2-methylpropyl;
1.11. Formula Q or any of 1.1-1.5, wherein $R_2$ is $C_{1-6}$alkoxyaryl$C_{1-6}$alkyl (e.g., $C_{1-6}$alkoxybenzyl);
1.12. Formula 1.11 wherein $R_2$ is p-methoxybenzyl;
1.13. Formula Q or 1.1 wherein $R_2$ is $C_{3-8}$cycloalkyl (e.g., cyclopentyl, cyclohexyl) optionally substituted with one or more amino (e.g., —NH$_2$), for example, 2-aminocyclopentyl or 2-aminocyclohexyl);
1.14. Formula 1.13 wherein $R_2$ is cyclopentyl or cyclohexyl;
1.15. Formula 1.13 wherein $R_2$ is 2-aminocyclopentyl;
1.16. Formula 1.13 wherein $R_2$ is 2-aminocyclohexyl;
1.17. Formula Q or any of 1.1-1.5, wherein $R_2$ is $C_{1-6}$haloalkyl;
1.18. Formula 1.17, wherein $R_2$ is 2,2,2-trifluoroethyl;
1.19. Formula Q or any of 1.1-1.5, wherein $R_2$ is $C_{3-8}$heterocycloalkyl (e.g., pyrrolidinyl, for example, pyrrolidin-3-yl) optionally substituted with $C_{1-6}$alkyl (e.g., methyl), for example, 1-methylpyrrolidin-3-yl;
1.20. Formula 1.19, wherein $R_2$ is pyrrolidinyl (e.g., pyrrolidin-3-yl);
1.21. Formula 1.19, wherein $R_2$ is 1-methylpyrrolidin-3-yl;
1.22. Formula Q or any of 1.1-1.5, wherein $R_2$ is $C_{3-8}$cycloalkyl-$C_{1-6}$alkyl (e.g., cyclopropylmethyl);
1.23. Formula 1.22, wherein $R_2$ is cyclopropylmethyl;
1.24. Formula Q or any of 1.1-1.5, wherein $R_2$ is $C_{0-6}$alkylamino$C_{0-6}$alkyl (e.g., 2-(dimethylamino)ethyl, 2-aminopropyl);
1.25. Formula 1.24, wherein $R_2$ is 2-(dimethylamino)ethyl;
1.26. Formula 1.24, wherein $R_2$ is 2-aminopropyl;
1.27. Formula Q or any of 1.1-1.5, wherein $R_2$ is aryl$C_{0-6}$alkyl (e.g., benzyl);
1.28. Formula 1.26, wherein $R_2$ is benzyl;
1.29. Formula Q or any of 1.1-1.5, wherein $R_2$ is heteroarylalkyl (e.g., pyridylmethyl);
1.30. Formula 1.29, wherein $R_2$ is pyridylmethyl;
1.31. Formula Q or any of 1.1-1.5, wherein $R_2$ is -G-J wherein: G is a single bond or, $C_{1-6}$alkylene (e.g., methylene) and J is cycloalkyl or heterocycloalkyl (e.g., oxetan-2-yl, pyrolyin-3-yl, pyrolyin-2-yl) optionally substituted with alkyl (e.g., (1-methylpyrrolidin-2-yl));
1.32. Formula 1.31, wherein G is $C_{1-6}$alkylene;
1.33. Formula 1.31, wherein G is methylene;
1.34. Formula 1.31, wherein G is a single bond; 1.35. Any of formulae 1.31-1.34, wherein J is cycloalkyl or heterocycloalkyl (e.g., oxetan-2-yl, pyrolyin-3-yl, pyrolyin-2-yl) optionally substituted with alkyl (e.g., 1-methylpyrrolidin-2-yl);
1.36. Any of formulae 1.31-1.34, wherein J is oxetan-2-yl, pyrolyin-3-yl, pyrolyin-2-yl;
1.37. Any of formulae 1.31-1.34, wherein J is 1-methylpyrrolidin-2-yl;
1.38. Any of the preceding formulae wherein $R_3$ is D-E-F;
1.39. Formula 1.38, wherein D is single bond, $C_{1-6}$alkylene (e.g., methylene), or aryl$C_{1-6}$alkylene (e.g., benzylene or —CH$_2$C$_6$H$_4$—);
1.40. Formula 1.38, wherein D is $C_{1-6}$alkylene (e.g., methylene);
1.41. Formula 1.38, wherein D is methylene;
1.42. Formula 1.38, wherein D is aryl$C_{1-6}$alkylene;
1.43. Formula 1.38, wherein D is benzylene;
1.44. Any of formulae 1.38-1.43, wherein E is $C_{1-6}$alkylene (e.g., methylene, ethynylene, prop-2-yn-1-ylene), arylene (e.g., phenylene or —C$_6$H$_4$—), $C_{1-6}$alkylarylene (e.g., -benzylene- or —CH$_2$C$_6$H$_4$—), amino$C_{1-6}$alkylene (e.g., —CH$_2$N(H)—) or amino (e.g., —N(H)—);
1.45. Formula 1.44, wherein E is $C_{1-6}$alkylene (e.g., methylene or ethynylene);
1.46. Formula 1.44, wherein E is methylene;
1.47. Formula 1.44, wherein E is ethynylene;
1.48. Formula 1.44, wherein E is amino$C_{1-6}$alkylene (e.g., —CH$_2$N(H)—);
1.49. Formula 1.44, wherein E is arylene (e.g., phenylene or —C$_6$H$_4$—);
1.50. Formula 1.44, wherein E is phenylene or —C$_6$H$_4$—;
1.51. Any of formulae 1.38-1.50, wherein F is $C_{1-6}$alkyl (e.g., isobutyl, isopropyl); aryl (e.g., phenyl); heteroaryl (e.g., 1,2,4-triazolyl, imidazolyl, pyridyl) optionally substituted with $C_{1-6}$alkyl, for example, pyrid-2-yl, imidazol-1-yl, 4-methylimidazolyl, 1-methylimidazol-2-yl, 1,2,4-triazol-1-yl; hetero$C_{3-8}$cycloalkyl (e.g., piperidinyl, pyrrolidinyl) optionally substituted with $C_{1-6}$alkyl (e.g., methyl), for example, pyrrolidin-1-yl, pyrrolidin-2-yl, 1-methylpyrrolidin-2-yl, piperidin-2-yl, 1-methylpiperidin-2-yl, 1-ethylpiperidin-2-yl; amino (e.g., —NH$_2$); $C_{1-6}$alkoxy; or —O-halo$C_{1-6}$alkyl (e.g., —O—CF$_3$);
1.52. Formula 1.51, wherein F is aryl (e.g., phenyl);
1.53. Formula 1.51, wherein F is phenyl;
1.54. Formula 1.51, wherein F is alkoxy (e.g., methoxy);
1.55. Formula 1.51 or 1.54, wherein F is methoxy;
1.56. Formula 1.51, wherein F is —O—$C_{1-6}$haloalkyl (e.g., —OCF$_3$);
1.57. Formula 1.51 or 1.56, wherein F is —OCF$_3$;
1.58. Formula 1.51, wherein F is —NH$_2$;
1.59. Formula 1.51, wherein F is hetero$C_{3-8}$cycloalkyl (e.g., piperidinyl, pyrrolidinyl) optionally substituted with $C_{1-6}$alkyl (e.g., methyl), for example, pyrrolidin-1-yl, pyrrolidin-2-yl, 1-methylpyrrolidin-2-yl, piperidin-2-yl, 1-methylpiperidin-2-yl, 1-ethylpiperidin-2-yl;
1.60. Formula 1.51 or 1.59 wherein F is pyrrolidin-1-yl;
1.61. Formula 1.51 or 1.59 wherein F is pyrrolidin-2-yl;
1.62. Formula 1.51 or 1.59 wherein F is 1-methylpyrrolidin-2-yl;
1.63. Formula 1.51 or 1.59 wherein F is piperidin-2-yl;
1.64. Formula 1.51 or 1.59 wherein F is 1-methylpiperidin-2-yl or 1-ethylpiperidin-2-yl;
1.65. Formula 1.51, wherein F is $C_{1-6}$alkyl (e.g., isobutyl, isopropyl);
1.66. Formula 1.51 or 1.65, wherein F is isobutyl;
1.67. Formula 1.51 or 1.65, wherein F is isopropyl;

1.68. Formula 1.51, wherein F is heteroaryl (e.g., 1,2,4-triazolyl, imidazolyl, pyridyl) optionally substituted with $C_{1-6}$alkyl, for example, pyrid-2-yl, imidazol-1-yl, 4-methylimidazol-1-yl, 1-methylimidazol-2-yl, 1,2,4-triazol-1-yl;

1.69. Formula 1.51 or 1.68, wherein F is pyridyl (e.g., pyrid-2-yl);

1.70. Formula 1.51 or 1.68, wherein F is imidazolyl optionally substituted with $C_{1-6}$alkyl;

1.71. Formula 1.51 or 1.68, wherein F is imidazol-1-yl;

1.72. Formula 1.51 or 1.68, wherein F is 4-methylimidazol-1-yl;

1.73. Formula 1.51 or 1.68, wherein F is 1-methylimidazol-2-yl;

1.74. Formula 1.51 or 1.68, wherein F is 1,2,4-triazol-1-yl;

1.75. Any of formulae 1.1-1.37, wherein $R_3$ is a substituted heteroarylalkyl, e.g., substituted with $C_{1-6}$haloalky;

1.76. Any of formulae 1.1-1.37, wherein $R_3$ is attached to one of the nitrogen atoms on the pyrazolo portion of Formula I and is a moiety of Formula A as hereinbefore described in Formula Q;

1.77. Formula 1.76, wherein $R_8$, $R_9$, $R_{11}$ and $R_{12}$ of Formula A are each H and $R_{10}$ is phenyl;

1.78. Formula 1.76, wherein $R_8$, $R_9$, $R_{11}$ and $R_{12}$ are each H and $R_{10}$ is pyridyl or thiadizolyl;

1.79. Formula 1.76, wherein $R_8$, $R_9$, $R_{11}$ and $R_{12}$ are each H and $R_{10}$ is 2-pyridyl;

1.80. Formula 1.76, wherein $R_8$, $R_9$, $R_{11}$ and $R_{12}$ are each H and $R_{10}$ is 4,6-dimethylpyrid-2-yl or 2-pyrrolinyl;

1.81. Formula 1.76, wherein X, Y and Z are all C, 1.82. Any of the preceding formulae, wherein $R_4$ aryl (e.g., phenyl) optionally substituted with one or more halo (e.g., F or Cl), hydroxy or $C_{1-6}$alkoxy, heteroaryl (e.g., pyrid-4-yl, pyrid-2-yl or pyrazol-3-yl) or heteroC$_{3-6}$cycloalkyl (e.g., pyrrolidin-3-yl);

1.83. Formula 1.82, wherein $R_4$ is aryl (e.g., phenyl), heteroaryl (e.g., pyrid-4-yl, pyrid-2-yl or pyrazol-3-yl) or heterocycloalkyl (e.g., pyrrolidin-3-yl);

1.84. Formula 1.82 or 1.83, wherein $R_4$ is aryl (e.g., phenyl) optionally substituted with one or more halo, hydroxy or $C_{1-6}$alkoxy;

1.85. Formula 1.82 or 1.83, wherein $R_4$ is phenyl optionally substituted with one or more halo, hydroxy or $C_{1-6}$alkoxy;

1.86. Formula 1.82 or 1.83, wherein $R_4$ is phenyl, 4-fluorophenyl, 4-hydroxyphenyl, 2-hydroxyphenyl, 2,4-dichlorophenyl;

1.87. Formula 1.82 or 1.83, wherein $R_4$ is heteroaryl;

1.88. Formula 1.82 or 1.83, wherein $R_4$ is pyrid-4-yl, pyrid-2-yl or pyrazol-3-yl;

1.89. Formula 1.82 or 1.83, wherein $R_4$ is heterocycloalkyl (e.g., pyrrolidin-3-yl)

1.90. Any of the preceding formulae wherein $R_5$ is H, $C_{1-6}$alkyl, $C_{3-8}$cycloalkyl (e.g., cyclopentyl), heteroaryl, aryl, p-benzylaryl (e.g., biphenyl-4-ylmethyl);

1.91. Formula 1.90, wherein $R_5$ is H, 1.92. Formula 1.90, wherein $R_5$ is $C_{1-6}$alkyl;

1.93. A compound selected from any of Examples 1-17;

1.94. A compound selected from the compounds of Examples 7, 8, 9, 15, 16 and 17 below;

1.95. A compound selected from any of the following:

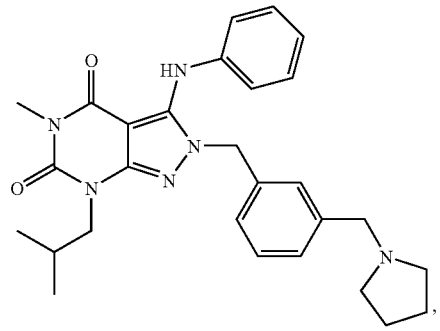

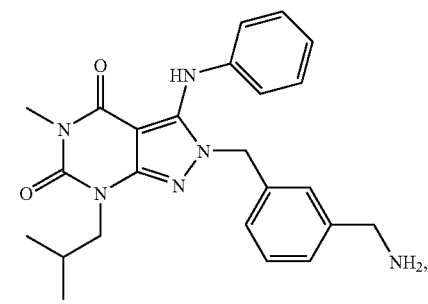

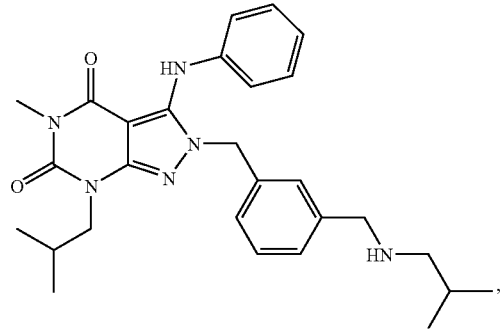

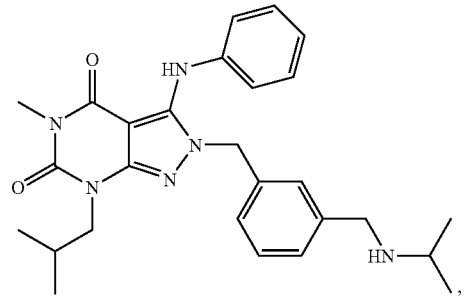

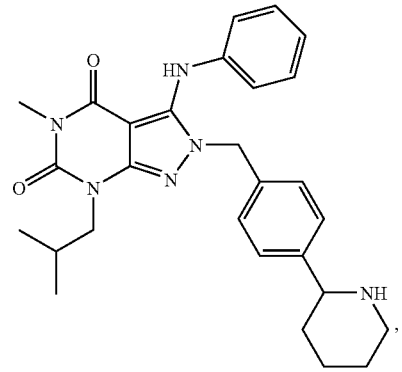

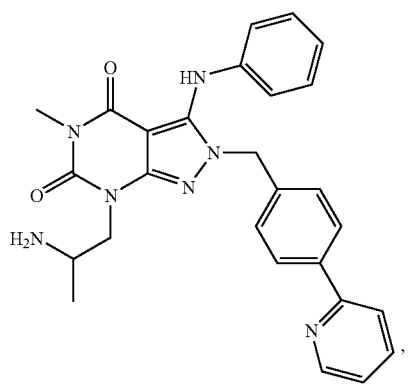
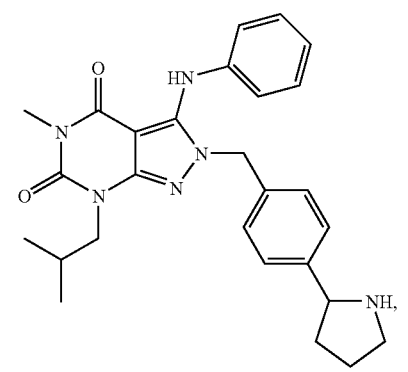
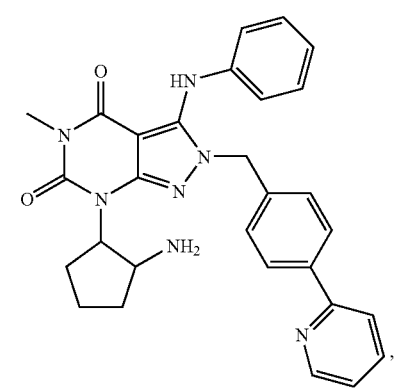
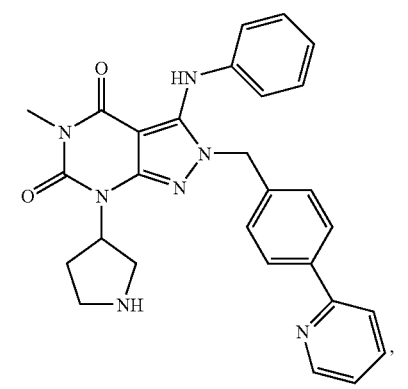
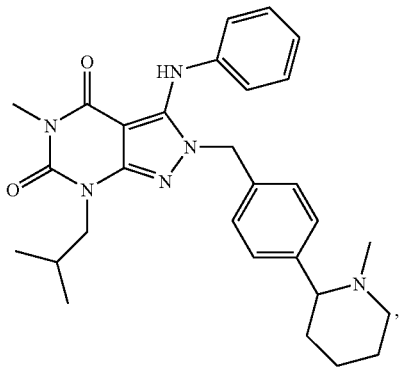
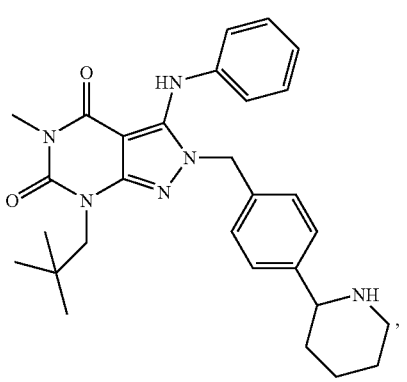
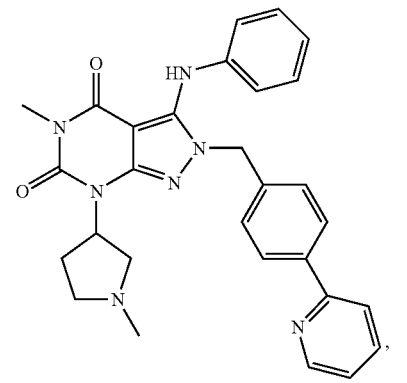
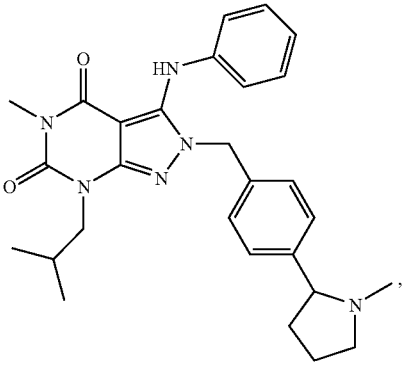

-continued
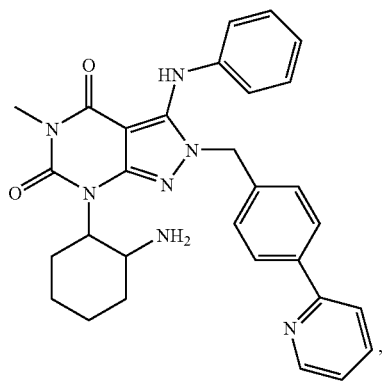
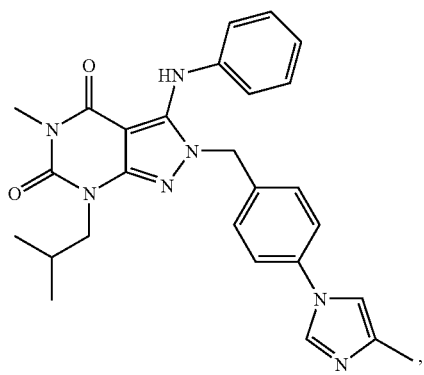
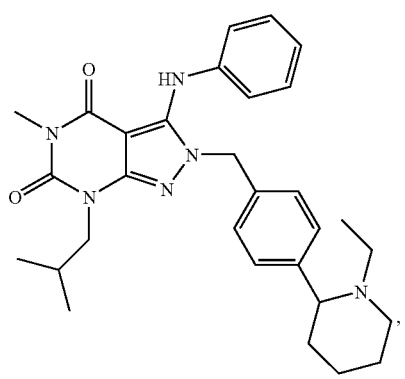
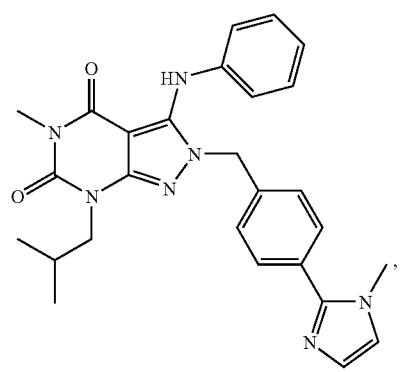
-continued
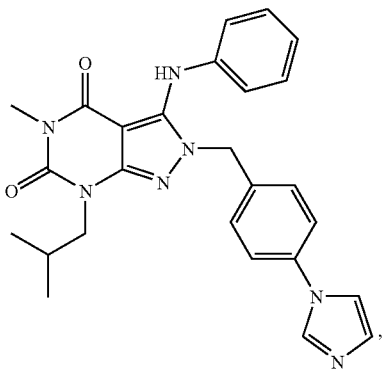
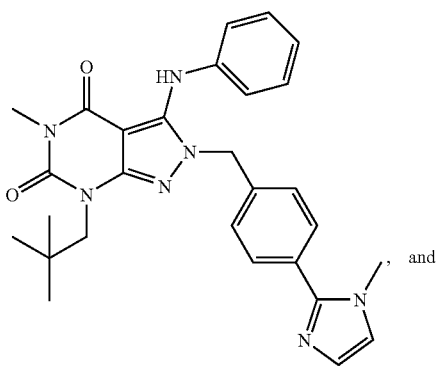, and
1.96. A compound selected from any of the following:
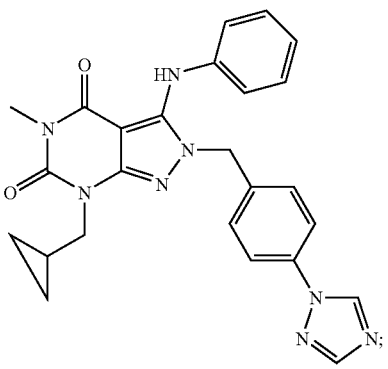
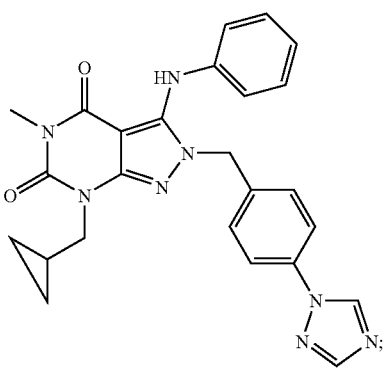

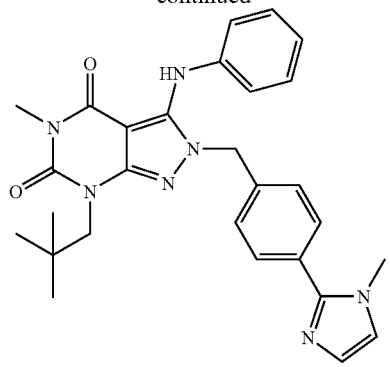
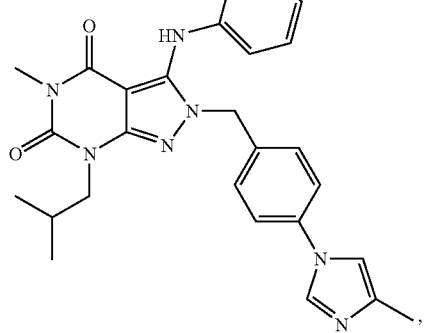
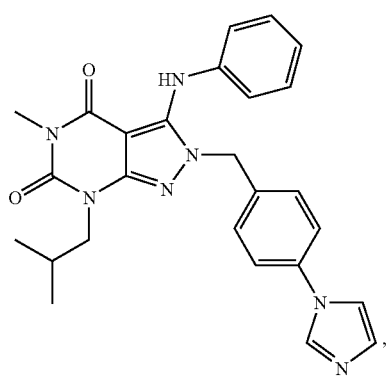
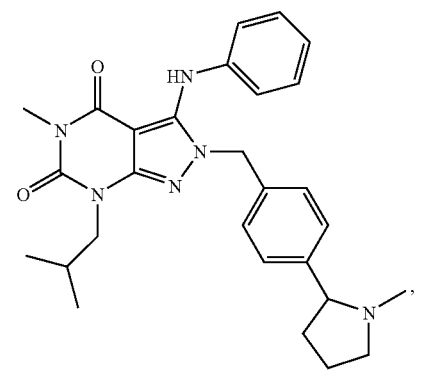
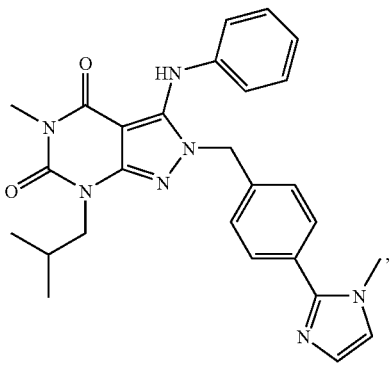
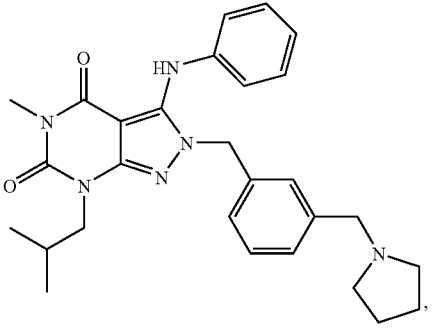
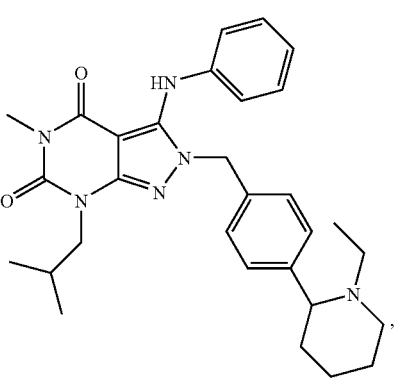
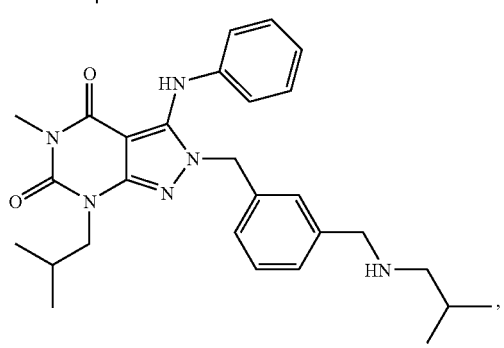

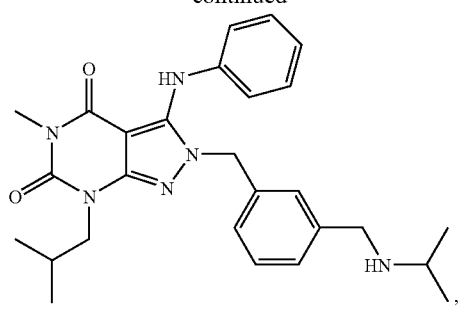
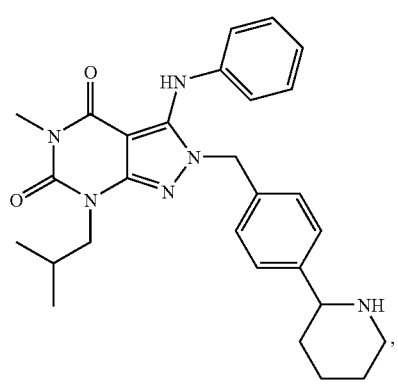
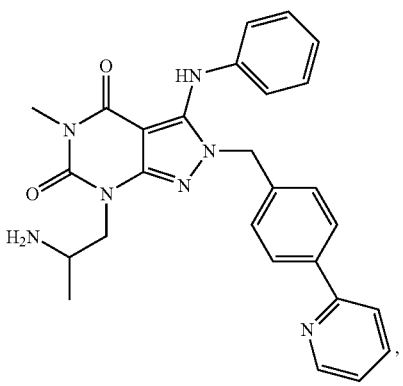
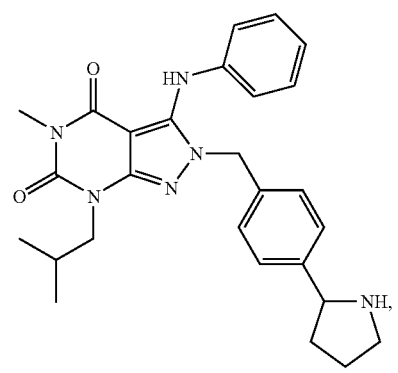
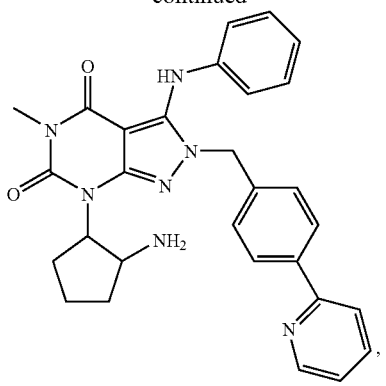
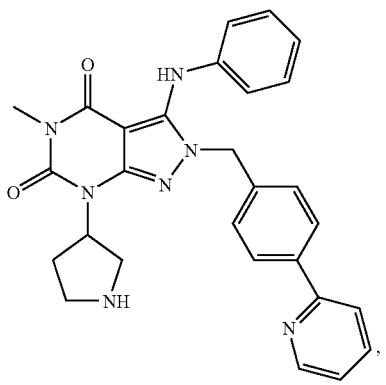
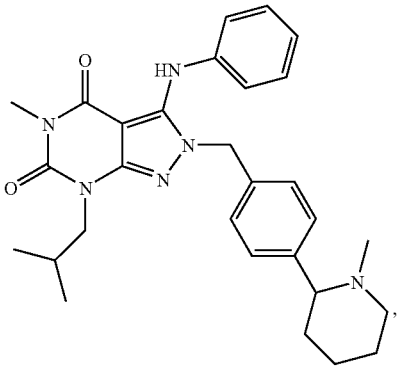
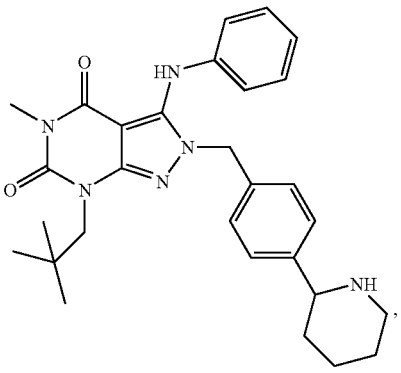

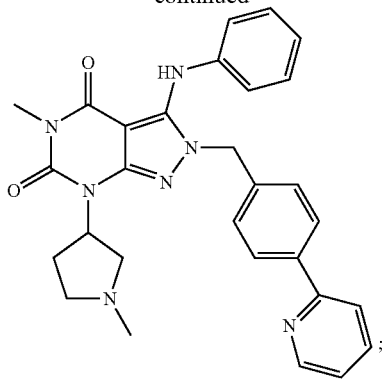

1.97. Any one of the preceding formulae wherein the compounds inhibit phosphodiesterase-mediated (e.g., PDE1-mediated, especially PDE1B-mediated) hydrolysis of cGMP, e.g., with an IC$_{50}$ of less than 1 µM, preferably less than preferably less than 250 nM, preferably less than 50 nM, more preferably less than 25 nM in an immobilized-metal affinity particle reagent PDE assay, for example, as described in Example 19;

such compounds according to any of the preceding formulae being in free, salt or prodrug form.

In a further embodiment, the invention provides a Compound of Formula Q or any of 1.1-1.97, provided that when -D-E- is an heteroarylalkyl or arylalkyl (e.g., benzyl), F is not aryl or heteroaryl. In a further embodiment, the invention provides a Compound of Formula Q or any of 1.1-1.97, provided that when G is a single bond, J is not cycloalkyl. In a further embodiment, the invention provides a Compound of Formula Q or any of 1.1-1.97, provided that when $R_4$ is aryl (e.g., phenyl), and $R_3$ is a moiety of Formula A, $R_{10}$ is a 5-fluoropyrid-2-yl, 6-fluoropyrid-2-yl, 4,6-dimethylpyrid-2-yl, 3,4-dihydro-2H-pyrol-5-yl, or 1,2,4-triazolyl.

In another embodiment, the Compounds of the Invention are pyrazolo[3,4-d]pyrimidine-4,6(5H,7H)-dione derivatives of formula Q-I

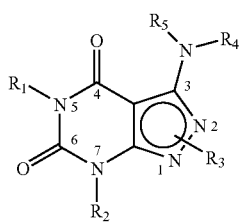

Formula Q-I wherein
(i) $R_1$ is H or $C_{1-6}$alkyl (e.g., methyl);
(ii) $R_2$ is H, alkyl (e.g., isopropyl, isobutyl, 2-methylbutyl, 2,2-dimethyl propyl), cycloalkyl (e.g., cyclopentyl, cyclohexyl), haloalkyl (e.g., trifluoromethyl, 2,2,2-trifluoroethyl), alkylaminoalkyl (e.g., 2-(dimethylamino) ethyl), hydroxyalkyl (e.g., 3-hydroxy-2-methyl propyl), arylalkyl (e.g., benzyl), heteroarylalkyl (e.g., pyridylmethyl), or alkoxyarylalkyl (e.g., 4-methoxybenzyl);
(iii) $R_3$ is D-E-F wherein
  1. D is single bond, $C_{1-6}$alkylene (e.g., methylene), or aryl$C_{1-6}$alkylene (e.g., benzylene or —CH$_2$C$_6$H$_4$—);
  2. E is a $C_{1-6}$alkylene (e.g., methylene, ethynylene, prop-2-yn-1-ylene), arylene (e.g., phenylene or —C$_6$H$_4$—), $C_{1-6}$alkylarylene (e.g., -benzylene- or —CH$_2$C$_6$H$_4$—), amino$C_{1-6}$alkylene (e.g., —CH$_2$N(H)—) or amino (e.g., —N(H)—); and
  3. F is
    $C_{1-6}$alkyl (e.g., isobutyl, isopropyl),
    aryl (e.g., phenyl),
    heteroaryl (e.g., 1,2,4-triazolyl, imidazolyl, pyridyl) optionally substituted with $C_{1-6}$alkyl, for example, pyrid-2-yl, imidazol-1-yl, 4-methylimidazolyl, 1-methylimidazol-2-yl, 1,2,4-triazol-1-yl,
    hetero$C_{3-8}$cycloalkyl (e.g., piperidinyl, pyrrolidinyl) optionally substituted with $C_{1-6}$alkyl (e.g., methyl), for example, pyrrolidin-1-yl, pyrrolidin-2-yl, 1-methylpyrrolidin-2-yl, piperidin-2-yl, 1-methylpiperidin-2-yl, 1-ethylpiperidin-2-yl,
    amino (e.g., —NH$_2$),
    $C_{1-6}$alkoxy, or
    —O-halo$C_{1-6}$alkyl (e.g., —O—CF$_3$),
    provided that when -D-E- is an heteroarylalkyl or arylalkyl (e.g., benzyl), F is not aryl or heteroaryl;
(iv) $R_4$ is aryl (e.g., phenyl), heteroaryl (e.g., pyrid-4-yl, pyrid-2-yl or pyrazol-3-yl) or heterocycloalkyl (e.g., pyrrolidin-3-yl); and
(v) $R_5$ is H, alkyl, cycloalkyl (e.g., cyclopentyl), heteroaryl, aryl, p-benzylaryl (e.g., biphenyl-4-ylmethyl);
wherein "alk", "alkyl", "haloalkyl" or "alkoxy" refers to $C_{1-6}$ alkyl and "cycloalkyl" refers to $C_{3-8}$ cycloalkyl;
in free, salt or prodrug form.

The invention also provides a Compound of Formula I

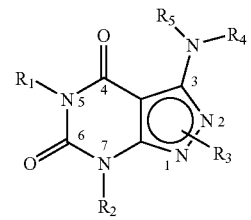

Formula I wherein
(i) $R_1$ is H or alkyl (e.g., methyl);
(ii) $R_2$ is H, alkyl (e.g., isopropyl, isobutyl, 2-methylbutyl, 2,2-dimethyl propyl), cycloalkyl (e.g., cyclopentyl, cyclohexyl), haloalkyl (e.g., trifluoromethyl, 2,2,2-trifluoroethyl), alkylaminoalkyl (e.g., 2-(dimethylamino) ethyl), hydroxyalkyl (e.g., 3-hydroxy-2-methyl propyl), arylalkyl (e.g., benzyl), heteroarylalkyl (e.g., pyridylmethyl), or alkoxyarylalkyl (e.g., 4-methoxybenzyl);
(iii) $R_3$ is D-E-F wherein
  1. D is single bond, alkylene (e.g., methylene), or arylalkylene (e.g., benzylene or —CH$_2$C$_6$H$_4$—);
  2. E is a alkylene (e.g., methylene, ethynylene, prop-2-yn-1-ylene), arylene (e.g., phenylene or —C$_6$H$_4$—), alkylarylene (e.g., -benzylene- or —CH$_2$C$_6$H$_4$—), aminoalkylene (e.g., —CH$_2$N(H)—) or amino (e.g., —N(H)—); and
  3. F is alkyl (e.g., isobutyl), aryl (e.g., phenyl), heteroaryl (e.g., pyrid-2-yl, 1,2,4-triazolyl), hetero$C_{3-6}$cycloalkyl (e.g., pyrrolidin-1-yl), amino (e.g., —NH$_2$), $C_{1-4}$alkoxy, or —O-haloalkyl (e.g., —O—CF$_3$);
provided that when -D-E- is an heteroarylalkyl or arylalkyl (e.g., benzyl), F is not aryl or heteroaryl.

(iv) R$_4$ is aryl (e.g., phenyl), heteroaryl (e.g., pyrid-4-yl, pyrid-2-yl or pyrazol-3-yl) or heterocycloalkyl (e.g., pyrrolidin-3-yl); and
(v) R$_5$ is H, alkyl, cycloalkyl (e.g., cyclopentyl), heteroaryl, aryl, p-benzylaryl (e.g., biphenyl-4-ylmethyl);
wherein "alk", "alkyl", "haloalkyl" or "alkoxy" refers to C$_{1-6}$ alkyl and "cycloalkyl" refers to C$_{3-6}$ cycloalkyl;
in free, salt or prodrug form.

The invention further provides compounds of Formula I as follows:

2.1 Formula I wherein R$_1$ is methyl;
2.2 Formula I or 2.1 wherein R$_2$ is C$_{1-6}$ alkyl;
2.3 Formula 2.2 wherein R$_2$ is isopropyl, isobutyl, 2,2-dimethylpropyl, or 2-methylbutyl;
2.4 Formula I or 2.1 wherein R$_2$ is hydroxy C$_{1-6}$ alkyl;
2.5 Formula I or 2.1 wherein R$_2$ is 3-hydroxy-2-methyl propyl;
2.6 Formula I or 2.1 wherein R$_2$ is C$_{1-6}$ alkoxy-benzyl;
2.7 Formula 2.6 wherein R$_2$ is p-methoxybenzyl;
2.8 Formula I or 2.1 wherein R$_2$ is C$_{3-6}$ cycloalkyl;
2.9 Formula 2.8 wherein R$_2$ is cyclopentyl or cyclohexyl;
2.10 Formula I or 2.1 wherein R$_2$ is C$_{1-6}$ haloalkyl;
2.11 Formula 2.10 wherein R$_2$ is 2,2,2-trifluoroethyl;
2.12 Any of the preceding formulae wherein R$_3$ is D-E-F and D is single bond, alkylene (e.g., methylene), or arylalkylene (e.g., -benzylene- or —CH$_2$C$_6$H$_4$—);
2.13 Any of the preceding formulae wherein R$_3$ is D-E-F and D is alkylene (e.g., methylene);
2.14 Any of the preceding formulae I-2.11 wherein R$_3$ is D-E-F and D is methylene
2.15 Any of the preceding formulae I-2.11 wherein R$_3$ is D-E-F and D is benzylene;
2.16 Any of the preceding formulae I-2.15, wherein R$_3$ is D-E-F and E is alkylene (e.g., methylene or ethynylene), arylene (e.g., phenylene), alkylarylene (e.g., -benzylene-), aminoalkylene (e.g., —CH$_2$N(H)—) or amino (e.g., —N(H)—);
2.17 Any of the preceding formulae I-2.16, wherein R$_3$ is D-E-F and E is alkylene (e.g., methylene or ethynylene);
2.18 Any of the preceding formulae I-2.17, wherein R$_3$ is D-E-F and E is methylene;
2.19 Any of the preceding formulae I-2.17, wherein R$_3$ is D-E-F and E is ethynylene;
2.20 Any of the preceding formulae I-2.17, wherein R$_3$ is D-E-F and E is aminoalkylene (e.g., —CH$_2$N(H)—);
2.21 Any of the preceding formulae I-2.20, wherein R$_3$ is D-E-F and F is alkyl (e.g., isobutyl), aryl (e.g., phenyl), heteroaryl (e.g., pyrid-2-yl, 1,2,4-triazolyl), heteroC$_{3-6}$cycloalkyl (e.g., pyrrolidin-1-yl), amine (e.g., —NH$_2$), alkoxy (e.g., methoxy) or —O-haloalkyl (—OCF$_3$);
2.22 Any of the preceding formulae I-2.21, wherein R$_3$ is D-E-F and F is aryl (e.g., phenyl);
2.23 Any of the preceding formulae I-2.22, wherein R$_3$ is D-E-F and F is phenyl;
2.24 Any of the preceding formulae I-2.21, wherein R$_3$ is D-E-F and F is alkoxy (e.g., methoxy) or —O-haloalkyl (e.g., —OCF$_3$);
2.25 Any of the preceding formulae I-2.21 or 2.24, wherein R$_3$ is D-E-F and F is methoxy;
2.26 Any of the preceding formulae I-2.21 or 2.24, wherein R$_3$ is D-E-F and F is —OCF$_3$;
2.27 Any of the preceding formulae I-2.21, wherein R$_3$ is D-E-F and F is —NH$_2$;
2.28 Any of the preceding formulae I-2.21, wherein R$_3$ is D-E-F and F is heteroC$_{3-6}$cycloalkyl (e.g., pyrrolidin-1-yl);
2.29 Any of the preceding formulae I-2.21 or 2.28, wherein R$_3$ is D-E-F and F is pyrrolidin-1-yl;
2.30 Any of the preceding formulae I-2.21, wherein R$_3$ is D-E-F and F is alkyl (e.g., isobutyl);
2.31 Any of the preceding formulae I-2.21 or 2.30, wherein R$_3$ is D-E-F and F is isobutyl;
2.32 Any of the preceding formulae I or any of 2.1-2.31, wherein R$_4$ is aryl (e.g., phenyl), heteroaryl (e.g., pyrid-4-yl, pyrid-2-yl or pyrazol-3-yl) or heterocycloalkyl (e.g., pyrrolidin-3-yl);
2.33 Any of the preceding formulae or any of 2.1-2.32, wherein R$_4$ is phenyl;
2.34 Any of the preceding formulae wherein R$_4$ is heteroaryl;
2.35 Any of the preceding formulae wherein R$_4$ is pyrid-4-yl, pyrid-2-yl or pyrazol-3-yl;
2.36 Any of the preceding formulae wherein R$_4$ is heterocycloalkyl (e.g., pyrrolidin-3-yl)
2.37 Any of the preceding formulae wherein R$_5$ is H,
2.38 A compound selected from the compounds of Examples 7, 8, 9, 15, 16 and 17 below; and/or
2.39 Any one of the preceding formulae wherein the compounds inhibit phosphodiesterase-mediated (e.g., PDE1-mediated, especially PDE1B-mediated) hydrolysis of cGMP, e.g., with an IC$_{50}$ of less than 1 μM, preferably less than 25 nM in an immobilized-metal affinity particle reagent PDE assay, for example, as described in Example 19;

such compounds according to any of the preceding formulae being in free, salt or prodrug form.

In another embodiment, the Compounds of the Invention are pyrazolo[3,4-d]pyrimidine-4,6(5H,7H)-dione derivatives of formula Q-II

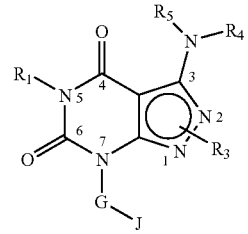

Formula Q-II wherein
(i) R$_1$ is H or alkyl (e.g., methyl);
(ii) G is a single bond or, alkylene (e.g., methylene);
(iii) J is cycloalkyl or heterocycloalkyl (e.g., oxetan-2-yl, pyrolyin-3-yl, pyrolyin-2-yl) optionally substituted with alkyl (e.g., (1-methylpyrrolidin-2-yl)); or
-G-J is
C$_{3-8}$cycloalkyl (e.g., cyclopentyl, cyclohexyl) substituted with one or more amino (e.g., —NH$_2$), for example, 2-aminocyclopentyl or 2-aminocyclohexyl),
C$_{3-8}$heterocycloalkyl (e.g., pyrrolidinyl, for example, pyrrolidin-3-yl) optionally substituted with C$_{1-6}$alkyl (e.g., methyl), for example, 1-methylpyrrolidin-3-yl,
C$_{3-8}$cycloalkyl-C$_{1-6}$alkyl (e.g., cyclopropylmethyl), aminoC$_{1-6}$alkyl (e.g., 2-aminopropyl),
provided that when G is a single bond, J is not an unsubstituted cycloalkyl;

(iv) $R_3$ is
a) D-E-F wherein
1. D is single bond, $C_{1-6}$alkylene (e.g., methylene), or aryl$C_{1-6}$alkylene (e.g., benzylene or —$CH_2C_6H_4$—);
2. E is a $C_{1-6}$alkylene (e.g., methylene, ethynylene, prop-2-yn-1-ylene), arylene (e.g., phenylene or —$C_6H_4$—), $C_{1-6}$alkylarylene (e.g., -benzylene- or —$CH_2C_6H_4$—), amino$C_{1-6}$alkylene (e.g., —$CH_2N(H)$—) or amino (e.g., —N(H)—); and
3. F is
$C_{1-6}$alkyl (e.g., isobutyl, isopropyl),
aryl (e.g., phenyl),
heteroaryl (e.g., 1,2,4-triazolyl, imidazolyl, pyridyl) optionally substituted with $C_{1-6}$alkyl, for example, pyrid-2-yl, imidazol-1-yl, 4-methylimidazolyl, 1-methylimidazol-2-yl, 1,2,4-triazol-1-yl,
hetero$C_{3-8}$cycloalkyl (e.g., piperidinyl, pyrrolidinyl) optionally substituted with $C_{1-6}$alkyl (e.g., methyl), for example, pyrrolidin-1-yl, pyrrolidin-2-yl, 1-methylpyrrolidin-2-yl, piperidin-2-yl, 1-methylpiperidin-2-yl, 1-ethylpiperidin-2-yl, amino (e.g., —$NH_2$),
$C_{1-6}$alkoxy, or
—O-halo$C_{1-6}$alkyl (e.g., —O—$CF_3$),
b) $R_3$ is a substituted heteroarylalkyl, e.g., substituted with haloalkyl; or
c) $R_3$ is attached to one of the nitrogen atoms on the pyrazolo portion of Formula Q-II and is
a moiety of Formula A

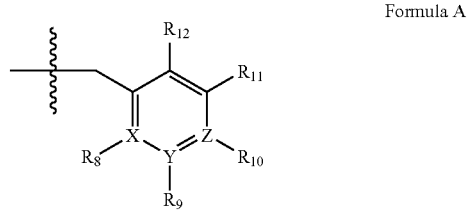

Formula A wherein X, Y and Z are, independently, N or C, and $R_8$, $R_9$, $R_{11}$ and $R_{12}$ are independently H or halogen (e.g., Cl or F); and $R_{10}$ is halogen, alkyl, cycloalkyl, haloalkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), alkyl sulfonyl (e.g., methyl sulfonyl), arylcarbonyl (e.g., benzoyl), or heteroarylcarbonyl, alkoxycarbonyl, (e.g., methoxycarbonyl), aminocarbonyl; preferably phenyl or pyridyl, e.g., 2-pyridyl; provided that when X, Y or X is nitrogen, $R_8$, $R_9$ or $R_{10}$, respectively, is not present;
(v) $R_4$ is aryl (e.g., phenyl) optionally substituted with one or more halo (e.g., F or Cl) or hydroxyl, heteroaryl (e.g., pyrid-4-yl, pyrid-2-yl or pyrazol-3-yl) or hetero$C_{3-6}$cycloalkyl (e.g., pyrrolidin-3-yl); and
(vi) $R_5$ is H, $C_{1-6}$alkyl, $C_{3-8}$cycloalkyl (e.g., cyclopentyl), heteroaryl, aryl, p-benzylaryl (e.g., biphenyl-4-ylmethyl),
wherein "alk", "alkyl", "haloalkyl" or "alkoxy" refers to $C_{1-6}$ alkyl and "cycloalkyl" refers to $C_{3-6}$ cycloalkyl;
in free, salt or prodrug form.

In another embodiment, the Compounds of the Invention are pyrazolo[3,4-d]pyrimidine-4,6(5H,7H)-dione derivatives of formula II

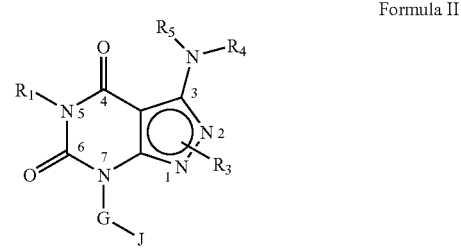

Formula II wherein
(i) $R_1$ is H or alkyl (e.g., methyl);
(ii) G is a single bond or, alkylene (e.g., methylene);
(iii) J is cycloalkyl or heterocycloalkyl (e.g., oxetan-2-yl, pyrolyin-3-yl, pyrolyin-2-yl) optionally substituted with alkyl (e.g., (1-methylpyrrolidin-2-yl));
provided that when G is a single bond, J is not cycloalkyl;
(iv) $R_3$ is
a) D-E-F wherein
1. D is single bond, alkylene (e.g., methylene), arylalkylene (e.g., benzylene or —$CH_2C_6H_4$—);
2. E is a alkylene (e.g., methylene, ethynylene, prop-2-yn-1-ylene), arylene (e.g., phenylene or —$C_6H_4$—), alkylarylene (e.g., -benzylene- or —$CH_2C_6H_4$—), aminoalkylene (e.g., —$CH_2N(H)$—) or amino (e.g., —N(H)—); and
3. F is alkyl (e.g., isobutyl), aryl (e.g., phenyl), heteroaryl (e.g., pyrid-2-yl, 1,2,4-triazolyl), hetero$C_{3-6}$cycloalkyl (e.g., pyrrolidin-1-yl), amino (e.g., —$NH_2$), $C_{1-4}$alkoxy, or —O-haloalkyl (e.g., —O—$CF_3$);
b) $R_3$ is a substituted heteroarylalkyl, e.g., substituted with haloalkyl; or
c) $R_3$ is attached to one of the nitrogen atoms on the pyrazolo portion of Formula II and is
a moiety of Formula A

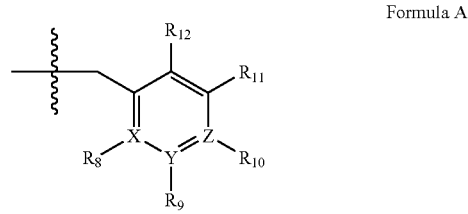

Formula A wherein X, Y and Z are, independently, N or C, and $R_8$, $R_9$, $R_{11}$ and $R_{12}$ are independently H or halogen (e.g., Cl or F); and $R_{10}$ is halogen, alkyl, cycloalkyl, haloalkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), alkyl sulfonyl (e.g., methyl sulfonyl), arylcarbonyl (e.g., benzoyl), or heteroarylcarbonyl, alkoxycarbonyl, (e.g., methoxycarbonyl), aminocarbonyl; preferably phenyl or pyridyl, e.g., 2-pyridyl; provided that when X, Y or X is nitrogen, $R_8$, $R_9$ or $R_{10}$, respectively, is not present;

(v) $R_4$ is aryl (e.g., phenyl), heteroaryl (e.g., pyrid-4-yl, pyrid-2-yl or pyrazol-3-yl) or heterocycloalkyl (e.g., pyrrolidin-3-yl); and (vi) $R_5$ is H, alkyl, cycloalkyl (e.g., cyclopentyl), heteroaryl, aryl, p-benzylaryl (e.g., biphenyl-4-ylmethyl);

wherein "alk", "alkyl", "haloalkyl" or "alkoxy" refers to $C_{1-6}$ alkyl and "cycloalkyl" refers to $C_{3-6}$ cycloalkyl; in free, salt or prodrug form.

The invention further provides compounds of Formula II as follows:

3.1 Formula II wherein $R_1$ is methyl;
3.2 Formula II or 3.1, wherein G is a single bond or alkylene (e.g., methylene) and J is cycloalkyl or heterocycloalkyl (e.g., oxetan-2-yl, pyrolyin-3-yl, pyrolyin-2-yl) optionally substituted with alkyl (e.g., (1-methylpyrrolidin-2-yl);
3.3 Formula II or 3.1 or 3.2 wherein G is alkylene (e.g., methylene);
3.4 Formula II or any of 3.1-3.3 wherein G is methylene;
3.5 Formula II or any of 3.1-3.4 wherein J is cycloalkyl or heterocycloalkyl (e.g., oxetan-2-yl, pyrolyin-3-yl, pyrolyin-2-yl) optionally substituted with alkyl (e.g., 1-methylpyrrolidin-2-yl);
3.6 Formula II or any of 3.1-3.5 wherein J is oxetan-2-yl, pyrolyin-3-yl, pyrolyin-2-yl;
3.7 Formula II or any of 3.1-3.5 wherein J is (1-methylpyrrolidin-2-yl);
3.8 Any of the preceding formulae wherein $R_3$ is D-E-F and D is single bond, alkylene (e.g., methylene), or arylalkylene (e.g., -benzylene-);
3.9 Any of the preceding formulae wherein D is alkylene (e.g., methylene);
3.10 Any of the preceding formulae II -3.9 wherein $R_3$ is D-E-F and D is methylene;
3.11 Any of the preceding formulae II-3.8 wherein $R_3$ is D-E-F and D is benzylene;
3.12 Any of the preceding formulae II-3.11 wherein $R_3$ is D-E-F and E is a alkylene (e.g., methylene, ethynylene, prop-2-yn-1-ylene), arylene (e.g., phenylene or —$C_6H_4$—), alkylarylene (e.g., -benzylene- or —$CH_2C_6H_4$—), aminoalkylene (e.g., —$CH_2N(H)$—) or amino (e.g., —N(H)—);
3.13 Any of the preceding formulae II-3.12, wherein $R_3$ is D-E-F and E is alkylene (e.g., methylene or ethynylene);
3.14 Any of the preceding formulae II-3.13, wherein $R_3$ is D-E-F and E is methylene;
3.15 Any of the preceding formulae II-3.13, wherein $R_3$ is D-E-F and E is ethynylene;
3.16 Any of the preceding formulae II-3.12, wherein $R_3$ is D-E-F and E is aminoalkylene (e.g., —$CH_2N(H)$—);
3.17 Any of the preceding formulae II-3.16, wherein $R_3$ is D-E-F and F is alkyl (e.g., isobutyl), aryl (e.g., phenyl), heteroaryl (e.g., pyrid-2-yl, 1,2,4-triazolyl), heteroC$_{3-6}$cycloalkyl (e.g., pyrrolidin-1-yl), amino (e.g., —$NH_2$), $C_{1-4}$alkoxy, or —O—haloalkyl (e.g., —O—$CF_3$);
3.18 Any of the preceding formulae II-3.17, wherein $R_3$ is D-E-F and F is aryl (e.g., phenyl);
3.19 Any of the preceding formulae II-3.18, wherein $R_3$ is D-E-F and F is phenyl;
3.20 Any of the preceding formulae II-3.17, wherein $R_3$ is D-E-F and F is —O-alkyl (e.g., methoxy) or —O-haloalkyl (e.g., —$OCF_3$);

3.21 Any of the preceding formulae II-3.17 or 3.20 wherein $R_3$ is D-E-F and F is methoxy;
3.22 Any of the preceding formulae II-3.17 or 3.20, wherein $R_3$ is D-E-F and F is —$OCF_3$;
3.23 Any of the preceding formulae II-3.17, wherein $R_3$ is D-E-F and F is —$NH_2$;
3.24 Any of the preceding formulae II-3.17, wherein $R_3$ is D-E-F and F is heteroC$_{3-6}$cycloalkyl (e.g., pyrrolidin-1-yl);
3.25 Any of the preceding formulae II-3.17 or 3.24, wherein $R_3$ is D-E-F and F is pyrrolidin-1-yl;
3.26 Any of the preceding formulae II-3.17, wherein $R_3$ is D-E-F and F is alkyl;
3.27 Any of the preceding formulae II-3.17 or 3.26, wherein F is isobutyl;
3.28 Any of the preceding formulae II-3.7 wherein $R_3$ is a moiety of Formula A wherein $R_8$, $R_9$, $R_{11}$ and $R_{12}$ are each H and $R_{10}$ is phenyl;
3.29 Any of the preceding formulae II-3.7 wherein $R_3$ is a moiety of Formula A wherein $R_8$, $R_9$, $R_{11}$ and $R_{12}$ are each H and $R_{10}$ is pyridyl or thiadizolyl;
3.30 Formula 3.29 wherein $R_3$ is a moiety of Formula A wherein $R_8$, $R_9$, $R_{11}$ and $R_{12}$ are each H and $R_{10}$ is 2-pyridyl optionally substituted with fluoro (e.g., 6-fluoropyrid-2-yl);
3.31 Any of the preceding formulae II-3.7 or 3.28-3.30, wherein X, Y and Z are all C
3.32 Any of the preceding formulae II-3.31, wherein $R_4$ is aryl (e.g., phenyl), heteroaryl (e.g., pyrid-4-yl, pyrid-2-yl or pyrazol-3-yl) or heterocycloalkyl (e.g., pyrrolidin-3-yl);
3.33 Any of the preceding formulae II-3.32, wherein $R_4$ is phenyl;
3.34 Any of the preceding formulae II-3.31, wherein $R_4$ is heteroaryl (e.g., pyrid-4-yl, pyrid-2-yl or pyrazol-3-yl);
3.35 Any of the preceding formulae II-3.31 or 3.34, wherein $R_4$ is pyrid-4-yl, pyrid-2-yl or pyrazol-3-yl;
3.36 Any of the preceding formulae II-3.31 or 3.34, wherein $R_4$ is pyrrolidin-3-yl;
3.37 Any of the preceding formulae wherein $R_5$ is H;
3.38 A compound selected from the compounds of Examples 6, 12, 13 and 14 below; and/or
3.39 Any one of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 19;

such compounds according to any of the preceding formulae being in free, salt or prodrug form.

In yet another embodiment, the Compounds of the Invention are compounds of Formula Q-III wherein

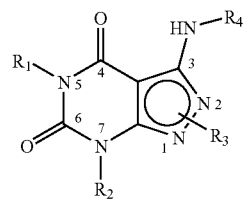

Formula Q-III wherein
(i) $R_1$ is H or alkyl (e.g., methyl);
(ii) $R_2$ is alkyl (e.g., isopropyl, isobutyl, isopropyl, 2,2-dimethylpropyl);
(iii) $R_3$ is
  a) D-E-F wherein
    1. D is single bond, $C_{1-6}$alkylene (e.g., methylene), or arylC$_{1-6}$alkylene (e.g., benzylene or —CH$_2$C$_6$H$_4$—);
    2. E is a $C_{1-6}$alkylene (e.g., methylene, ethynylene, prop-2-yn-1-ylene), arylene (e.g., phenylene or —C$_6$H$_4$—), $C_{1-6}$alkylarylene (e.g., -benzylene- or —CH$_2$C$_6$H$_4$—), aminoC$_{1-6}$alkylene (e.g., —CH$_2$N(H)—) or amino (e.g., —N(H)—); and
    3. F is
      $C_{1-6}$alkyl (e.g., isobutyl, isopropyl), aryl (e.g., phenyl),
      heteroaryl (e.g., 1,2,4-triazolyl, imidazolyl, pyridyl) optionally substituted with $C_{1-6}$alkyl, for example, pyrid-2-yl, imidazol-1-yl, 4-methylimidazolyl, 1-methylimidaz-2-yl, 1,2,4-triazol-1-yl,
      heteroC$_{3-8}$cycloalkyl (e.g., piperidinyl, pyrrolidinyl) optionally substituted with $C_{1-6}$alkyl (e.g., methyl), for example, pyrrolidin-1-yl, pyrrolidin-2-yl, 1-methylpyrrolidin-2-yl, piperidin-2-yl, 1-methylpiperidin-2-yl, 1-ethylpiperidin-2-yl,
      amino (e.g., —NH$_2$),
      $C_{1-6}$alkoxy, or
      —O-haloC$_{1-6}$alkyl (e.g., —O—CF$_3$),
  b) $R_3$ is a substituted heteroarylalkyl, e.g., substituted with haloalkyl; or
  c) $R_3$ is attached to one of the nitrogen atoms on the pyrazolo portion of Formula Q-III and is a moiety of Formula A

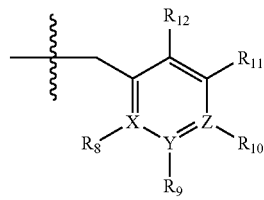

Formula A wherein X, Y and Z are, independently, N or C, and $R_8$, $R_9$, $R_{11}$ and $R_{12}$ are independently H or halogen (e.g., Cl or F); and $R_{10}$ is halogen, alkyl, cycloalkyl, haloalkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), alkyl sulfonyl (e.g., methyl sulfonyl), arylcarbonyl (e.g., benzoyl), or heteroarylcarbonyl, alkoxycarbonyl, (e.g., methoxycarbonyl), aminocarbonyl; preferably phenyl or pyridyl, e.g., 2-pyridyl; provided that when X, Y or X is nitrogen, $R_8$, $R_9$ or $R_{10}$, respectively, is not present;
(iv) $R_4$ is aryl (e.g., phenyl) optionally substituted with one or more halo (e.g., F or Cl) or hydroxyl, heteroaryl (e.g., pyrid-4-yl, pyrid-2-yl or pyrazol-3-yl) or heteroC$_{3-6}$cycloalkyl (e.g., pyrrolidin-3-yl);

wherein "alk", "alkyl", "haloalkyl" or "alkoxy" refers to $C_{1-6}$ alkyl and "cycloalkyl" refers to $C_{3-6}$ cycloalkyl;
in free, salt or prodrug form.

In a further embodiment, the Compound of Formula Q-III includes the proviso that when $R_4$ is unsubstituted aryl (e.g., phenyl), and $R_3$ is a moiety of Formula A, wherein $R_{10}$ is a 5-fluoropyrid-2-yl, 6-fluoropyrid-2-yl, 4,6-dimethylpyrid-2-yl, 3,4-dihydro-2H-pyrol-5-yl, or 1,2,4-triazolyl, In still another embodiment, the Compounds of the Invention are compounds of Formula III wherein

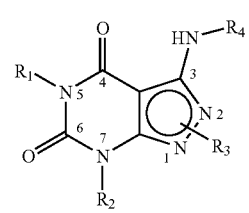

Formula III wherein
(i) $R_1$ is H or alkyl (e.g., methyl);
(ii) $R_2$ is alkyl (e.g., isopropyl, isobutyl, isopropyl, 2,2-dimethylpropyl);
(iii) $R_3$ is
  a) D-E-F wherein
    1. D is single bond, alkylene (e.g., methylene) or arylalkylene (e.g., benzylene or —CH$_2$C$_6$H$_4$—);
    2. E is a alkylene (e.g., methylene, ethynylene, prop-2-yn-1-ylene), arylene (e.g., phenylene or —C$_6$H$_4$—), alkylarylene (e.g., -benzylene- or —CH$_2$C$_6$H$_4$—), aminoalkylene (e.g., —CH$_2$N(H)—) or amino (e.g., —N(H)—); and
    3. F is alkyl (e.g., isobutyl), aryl (e.g., phenyl), heteroaryl (e.g., pyrid-2-yl, 1,2,4-triazolyl), hetero C$_{3-6}$cycloalkyl (e.g., pyrrolidin-1-yl), amino (e.g., —NH$_2$), $C_{1-4}$alkoxy, or —O-haloalkyl (e.g., —O—CF$_3$);
  b) $R_3$ is a substituted heteroarylalkyl, e.g., substituted with haloalkyl; or
  c) $R_3$ is attached to one of the nitrogen atoms on the pyrazolo portion of Formula III and is
     a moiety of Formula A

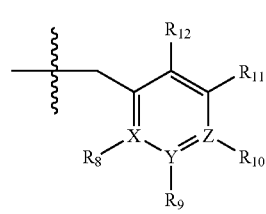

Formula A wherein X, Y and Z are, independently, N or C, and $R_8$, $R_9$, $R_{11}$ and $R_{12}$ are independently H or halogen (e.g., Cl or F); and $R_{10}$ is halogen, alkyl, cycloalkyl, haloalkyl (e.g., trifluoromethyl), aryl (e.g., phenyl), heteroaryl (e.g., pyridyl, (for example, pyrid-2-yl) or e.g., thiadiazolyl (for example, 1,2,3-thiadiazol-4-yl), diazolyl, triazolyl (e.g., 1,2,4-triazol-1-yl), tetrazolyl (e.g., tetrazol-5-yl), alkoxadiazolyl (e.g., 5-methyl-1,2,4-oxadiazol), pyrazolyl (e.g., pyrazol-1-yl), alkyl sulfonyl (e.g., methyl sulfonyl), arylcarbonyl (e.g., benzoyl), or heteroarylcarbonyl, alkoxycarbonyl, (e.g., methoxycarbonyl), aminocarbonyl; preferably phenyl or pyridyl, e.g., 2-pyridyl; provided that when X, Y or X is nitrogen, $R_8$, $R_9$ or $R_{10}$, respectively, is not present;
(iv) $R_4$ is aryl (e.g., phenyl), heteroaryl (e.g., pyrid-4-yl, pyrid-2-yl or pyrazol-3-yl) or heterocycloalkyl (e.g., pyrrolidin-3-yl); provided that when $R_4$ is aryl (e.g., phenyl), and $R_3$ is a moiety of Formula A, $R_{10}$ is a 5-fluoropyrid-2-yl, 6-fluoropyrid-2-yl, 4,6-dimethylpyrid-2-yl, 3,4-dihydro-2H-pyrol-5-yl, or 1,2,4-triazolyl, wherein "alk", "alkyl", "haloalkyl" or "alkoxy" refers to $C_{1-6}$ alkyl and "cycloalkyl" refers to $C_{3-6}$ cycloalkyl;
in free, salt or prodrug form.

The invention further provides compounds of Formula III as follows:
4.1 Formula III wherein $R_1$ is methyl;
4.2 Formula III or 4.1 wherein $R_2$ is $C_{1-6}$ alkyl;
4.3 Formula III, 4.1 or 4.2, wherein $R_2$ is isobutyl, 2,2-dimethyl propyl, or 2-methylbutyl;
4.4 Formula III or any of 4.1-4.3, wherein $R_2$ is hydroxy $C_{1-6}$ alkyl;
4.5 Formula III or any of 4.1-4.3, wherein $R_2$ is 3-hydroxy-2-methyl propyl;
4.6 Formula III or 4.1 wherein $R_2$ is $C_{1-6}$ alkoxy-benzyl;
4.7 Formula 4.6 wherein $R_2$ is p-methoxybenzyl;
4.8 Formula III or 4.1 wherein $R_2$ is $C_{3-6}$ cycloalkyl;
4.9 Formula 4.8 wherein $R_2$ is cyclopentyl or cyclohexyl;
4.10 Formula III or 4.1 wherein $R_2$ is $C_{1-6}$ haloalkyl;
4.11 Formula 4.10 wherein $R_2$ is 2,2,2-trifluoroethyl;
4.12 Any of the preceding formulae III or any of 4.1-4.11, wherein $R_3$ is a moiety of Formula A wherein $R_8$, $R_9$, $R_{11}$ and $R_{12}$ are each H and $R_{10}$ is phenyl;
4.13 Any of the preceding formulae III or any of 4.1-4.12, wherein $R_3$ is a moiety of Formula A wherein $R_8$, $R_9$, $R_{11}$ and $R_{12}$ are each H and $R_{10}$ is pyridyl or thiadiazolyl;
4.14 Formula III or any of 4.1-4.13, wherein $R_3$ is a moiety of Formula A wherein $R_8$, $R_9$, $R_{11}$ and $R_{12}$ are each H and $R_{10}$ is 2-pyridyl;
4.15 Formula III or any of 4.1-4.13, wherein $R_3$ is a moiety of Formula A wherein $R_8$, $R_9$, $R_{11}$ and $R_{12}$ are each H and $R_{10}$ is 4,6-dimethylpyrid-2-yl or 2-pyrrolinyl
4.16 Any of the preceding formulae III or any of 4.1-4.15, wherein X, Y and Z are all C;
4.17 Any of the preceding formulae III or any of 4.1-4.11 or 4.16, wherein $R_3$ is D-E-F and D is single bond, alkylene (e.g., methylene) or arylalkylene (e.g., -benzyl-);
4.18 Any of the preceding formulae III or any of 4.1-4.11 or 4.16-4.17, wherein $R_3$ is D-E-F and D is alkylene (e.g., methylene);
4.19 Any of the preceding formulae III or any of 4.1-4.11 or 4.16-4.18, wherein $R_3$ is D-E-F and D is methylene
4.20 Any of the preceding formulae III or any of 4.1-4.11 or 4.16, wherein $R_3$ is D-E-F and D is benzylene;
4.21 Any of the preceding formulae III or any of 4.1-4.11 or 4.16-4.20, wherein $R_3$ is D-E-F and E is alkylene (e.g., methylene or ethynylene), arylene (e.g., phenylene), alkylarylene (e.g., -benzylene-), aminoalkylene (e.g., —$CH_2N(H)$—) or amino (e.g., —N(H)—);
4.22 Any of the preceding formulae III or any of 4.1-4.11 or 4.16-4.21, wherein $R_3$ is D-E-F and E is alkylene (e.g., methylene or ethynylene);
4.23 Any of the preceding formulae III or any of 4.1-4.11 or 4.16-4.22, wherein $R_3$ is D-E-F and E is methylene;
4.24 Any of the preceding formulae III or any of 4.1-4.11 or 4.16-4.22, wherein $R_3$ is D-E-F and E is ethynylene;
4.25 Any of the preceding formulae III or any of 4.1-4.11 or 4.16-4.20, wherein $R_3$ is D-E-F and E is aminoalkylene (e.g., —$CH_2N(H)$—);
4.26 Any of the preceding formulae III or any of 4.1-4.11 or 4.16-4.25, wherein $R_3$ is D-E-F and F is alkyl (e.g., isobutyl), aryl (e.g., phenyl), heteroaryl (e.g., pyrid-2-yl, 1,2,4-triazolyl), heteroC$_{3-6}$cycloalkyl (e.g., pyrrolidin-1-yl), amine (e.g., —$NH_2$), alkoxy (e.g., methoxy) or —O-haloalkyl (—$OCF_3$);
4.27 Any of the preceding formulae III or any of 4.1-4.11 or 4.16-4.26, wherein $R_3$ is D-E-F and F is aryl (e.g., phenyl);
4.28 Any of the preceding formulae III or any of 4.1-4.11 or 4.16-4.27, wherein $R_3$ is D-E-F and F is phenyl;
4.29 Any of the preceding formulae III or any of 4.1-4.11 or 4.16-4.25, wherein $R_3$ is D-E-F and F is alkoxy (e.g., methoxy) or —O-haloalkyl (e.g., —$OCF_3$);
4.30 Any of the preceding formulae III or any of 4.1-4.11 or 4.16-4.25 or 4.29, wherein $R_3$ is D-E-F and F is methoxy;
4.31 Any of the preceding formulae III or any of 4.1-4.11 or 4.16-4.25 or 4.29, wherein $R_3$ is D-E-F and F is —$OCF_3$;
4.32 Any of the preceding formulae III or any of 4.1-4.11 or 4.16-4.25, wherein $R_3$ is D-E-F and F is —$NH_2$;
4.33 Any of the preceding formulae III or any of 4.1-4.11 or 4.16-4.25, wherein $R_3$ is D-E-F and F is heteroC$_{3-6}$cycloalkyl (e.g., pyrrolidin-1-yl);
4.34 Any of the preceding formulae III or any of 4.1-4.11 or 4.16-4.25 or 4.33, wherein $R_3$ is D-E-F and F is pyrrolidin-1-yl;
4.35 Any of the preceding formulae III or any of 4.1-4.11 or 4.16-4.25, wherein $R_3$ is D-E-F and F is alkyl (e.g., isobutyl);
4.36 Any of the preceding formulae III or any of 4.1-4.11 or 4.16-4.25 or 4.35, wherein $R_3$ is D-E-F and F is isobutyl;
4.37 Any of the preceding formulae III or any of 4.1-4.36, wherein $R_4$ is aryl (e.g., phenyl), heteroaryl (e.g., pyrid-4-yl, pyrid-2-yl or pyrazol-3-yl) or heterocycloalkyl (e.g., pyrrolidin-3-yl); provided that when $R_4$ is aryl (e.g., phenyl), and $R_3$ is a moiety of Formula A, $R_{10}$ is a 5-fluoropyrid-2-yl, 6-fluoropyrid-2-yl, 4,6-dimethylpyrid-2-yl, 3,4-dihydro-2H-pyrol-5-yl, or 1,2,4-triazolyl;
4.38 Any of the preceding formulae III or any of 4.1-4.37, wherein $R_4$ is heterocycloalkyl (e.g., pyrrolidin-3-yl);
4.39 Any of the preceding formulae III or any of 4.1-4.38, wherein $R_4$ is pyrrolidin-3-yl);
4.40 Any of the preceding formulae III or any of 4.1-4.37 or 4.39, wherein $R_4$ is pyrid-4-yl, pyrid-2-yl or pyrazol-3-yl;
4.41 Any of the preceding formulae III or any of 4.1-4.37 or 4.40, wherein $R_4$ is aryl, provided that when $R_4$ is aryl (e.g., phenyl), and $R_3$ is a moiety of Formula A, $R_{10}$ is a 5-fluoropyrid-2-yl, 6-fluoropyrid-2-yl, 4,6-dimethylpyrid-2-yl, 3,4-dihydro-2H-pyrol-5-yl, or 1,2,4-triazolyl;
4.42 Any of the preceding formulae III or any of 4.1-4.37 or 4.40-4.41, wherein $R_4$ is phenyl, provided that when $R_4$ is aryl (e.g., phenyl), and $R_3$ is a moiety of Formula A, $R_{10}$ is a 5-fluoropyrid-2-yl, 6-fluoropyrid-2-yl, 4,6-dimethylpyrid-2-yl, 3,4-dihydro-2H-pyrol-5-yl, or 1,2,4-triazolyl;
4.43 A compound selected from the compounds of Examples 1-5 and 9-11, below; and/or
4.44 Any one of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than 25 nM in an immobilized-metal affinity particle reagent PDE assay, for example, as described in Example 19;

The invention further provides a Compound of Formula Q, Q-I, Q-II or Q-III as hereinbefore defined as follows:

5.1 Formula Q, Q-I, Q-II or Q-III, wherein $R_2$ is $C_{3-8}$cycloalkyl (e.g., cyclopentyl, cyclohexyl) is substituted with one or more amino (e.g., —$NH_2$), for example, 2-aminocyclopentyl or 2-aminocyclohexyl), 5.2 Formula 5.1, wherein $R_2$ is 2-aminocyclopentyl;

5.3 Formula 5.1, wherein $R_2$ is 2-aminocyclohexyl;

5.4 Formula Q, Q-I, Q-II or Q-III, wherein $R_2$ is 2-aminopropyl;

5.5 Formula Q, Q-I, Q-II or Q-III, wherein $R_2$ is $C_{3-8}$heterocycloalkyl (e.g., pyrrolidinyl, for example, pyrrolidin-3-yl) optionally substituted with $C_{1-6}$alkyl (e.g., methyl), for example, 1-methylpyrrolidin-3-yl;

5.6 Formula 5.5, wherein $R_2$ is pyrrolidinyl (e.g., pyrrolidin-3-yl) optionally substituted with $C_{1-6}$alkyl;

5.7 Formula 5.5, wherein $R_2$ is 1-methylpyrrolidin-3-yl;

5.8 Formula Q, Q-I, Q-II or Q-III, wherein $R_2$ is $C_{3-8}$cycloalkyl-$C_{1-6}$alkyl (e.g., cyclopropylmethyl);

5.9 Formula 5.8, wherein $R_2$ is cyclopropylmethyl;

5.10 Formula Q, Q-I, Q-II or Q-III, or any of 5.1-5.9, wherein $R_4$ is aryl (e.g., phenyl) optionally substituted with one or more halo (e.g., F or Cl), hydroxy or $C_{1-6}$alkoxy;

5.11 Formula 5.10, wherein $R_4$ is phenyl optionally substituted with one or more halo;

5.12 Formula 5.10, wherein $R_4$ is phenyl substituted with one or more fluoro or chloro;

5.13 Formula 5.10, wherein $R_4$ is phenyl substituted with one or more hydroxy;

5.14 Formula Q, Q-I, Q-II or Q-III, or any of 5.1-5.13, wherein $R_3$ is D-E-F and F is amino;

5.15 Formula Q, Q-I, Q-II or Q-III, or any of 5.1-5.13, wherein $R_3$ is D-E-F and F is isopropyl;

5.16 Formula Q, Q-I, Q-II or Q-III, or any of 5.1-5.13, wherein $R_3$ is D-E-F and F is piperidinyl (e.g., piperidin-2-yl);

5.17 Formula Q, Q-I, Q-II or Q-III, or any of 5.1-5.13, wherein $R_3$ is D-E-F and F is pyrrolidin-2-yl;

5.18 Formula Q, Q-I, Q-II or Q-III, or any of 5.1-5.13, wherein $R_3$ is D-E-F and F is 1-methylpyrrolidin-2-yl;

5.19 Formula Q, Q-I, Q-II or Q-III, or any of 5.1-5.13, wherein $R_3$ is D-E-F and F is 1-methylpiperidin-2-yl or 1-ethylpiperidin-2-yl;

5.20 Formula Q, Q-I, Q-II or Q-III, or any of 5.1-5.13, wherein $R_3$ is D-E-F and F is imidazolyl (e.g., imidazol-1-yl);

5.21 Formula Q, Q-I, Q-II or Q-III, or any of 5.1-5.13, wherein $R_3$ is D-E-F and F is 1-methylimidazol-2-yl;

5.22 A compound selected from any of the following:

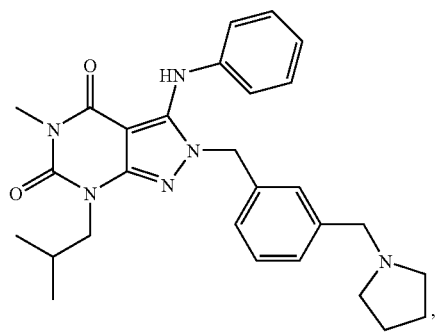

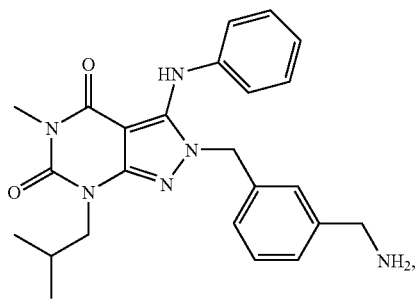

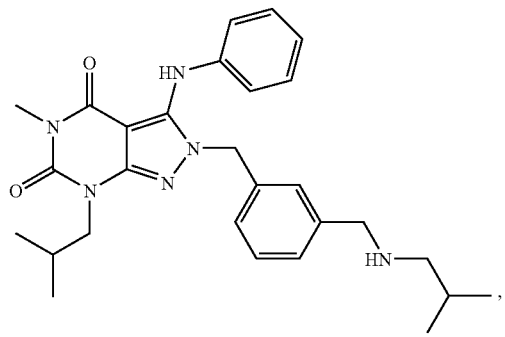

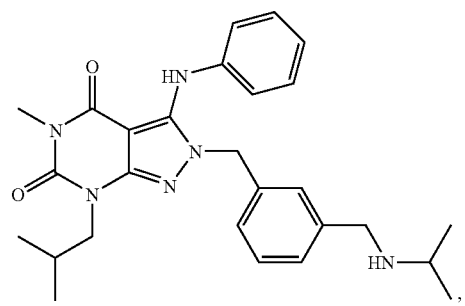

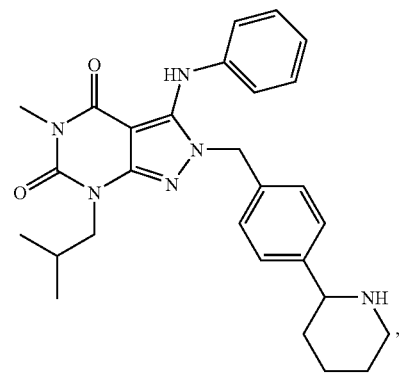

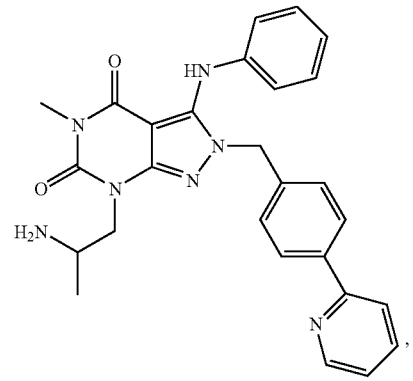

-continued
| 31 | 32 |
|---|---|
| 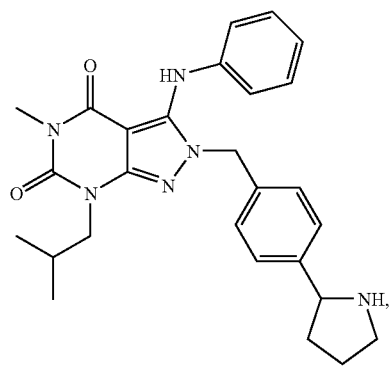 | 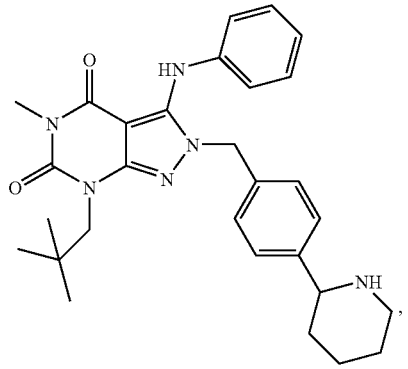 |
| 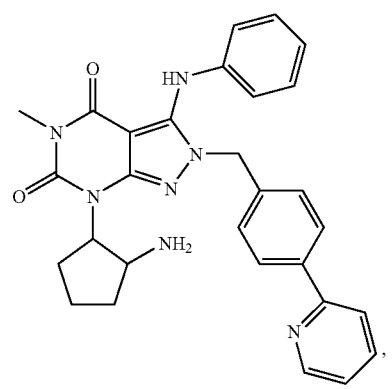 | 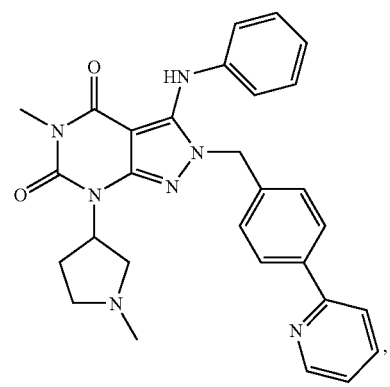 |
| 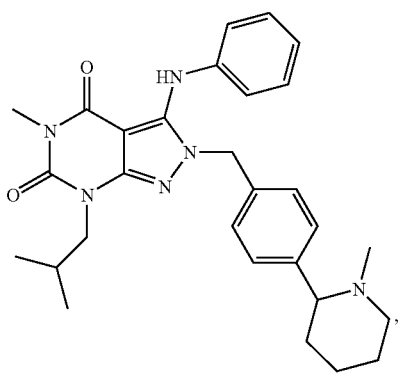 | 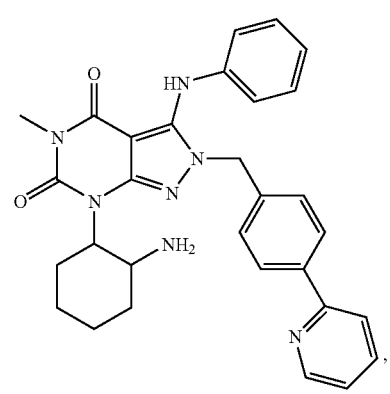 |

33
-continued
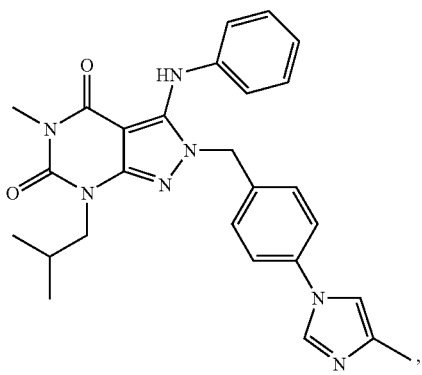
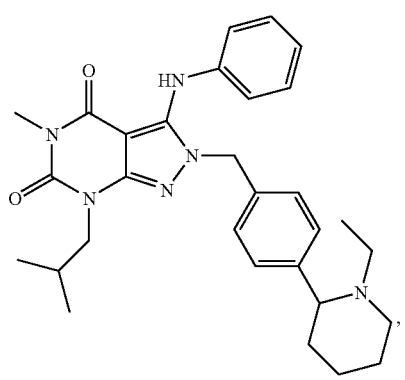
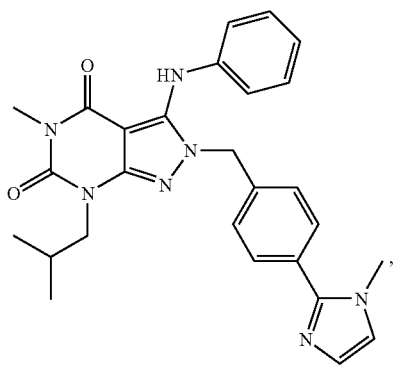
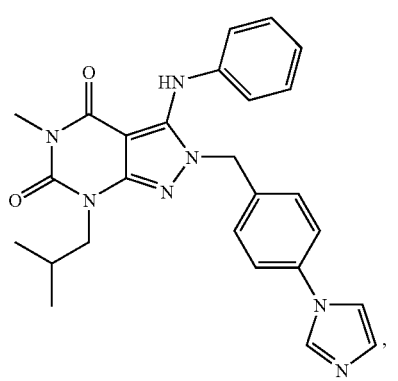
34
-continued
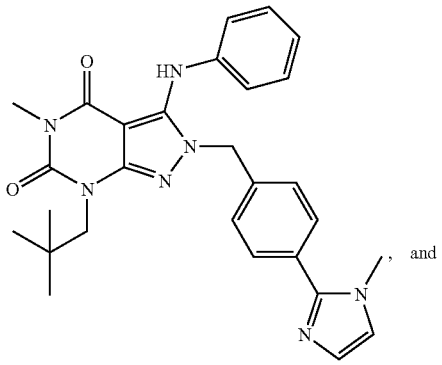, and
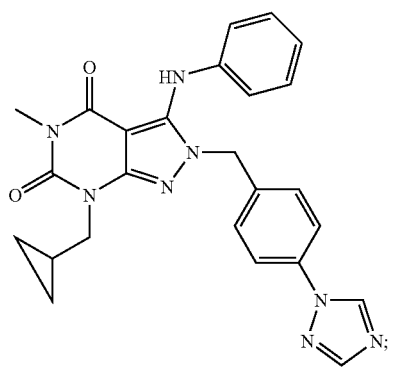
5.23 A compound selected from any of the following:
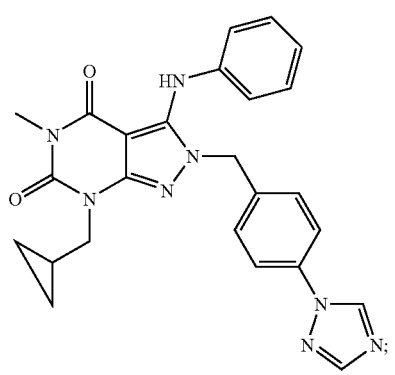
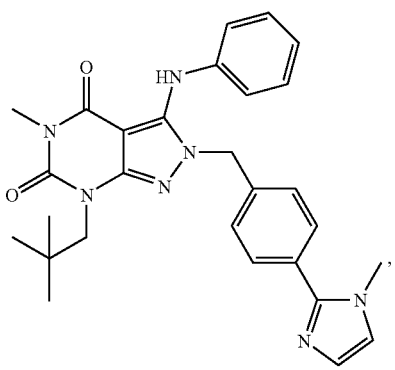

35
-continued
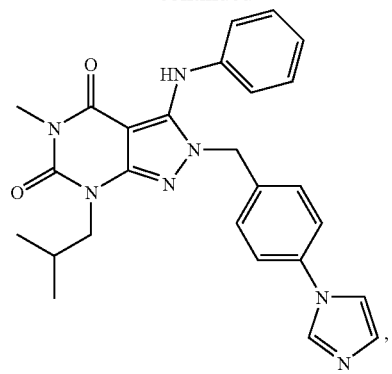
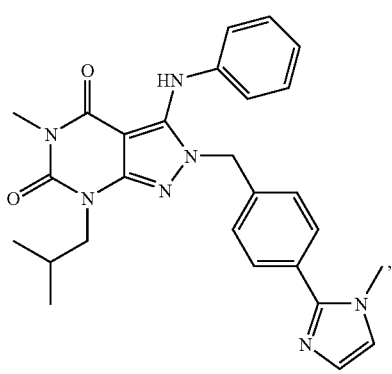
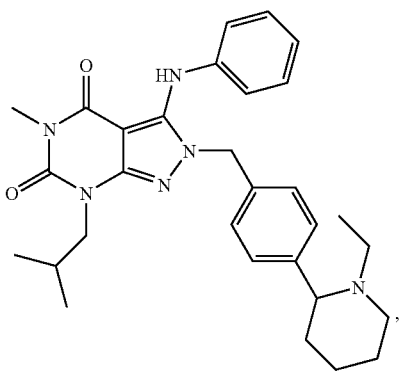
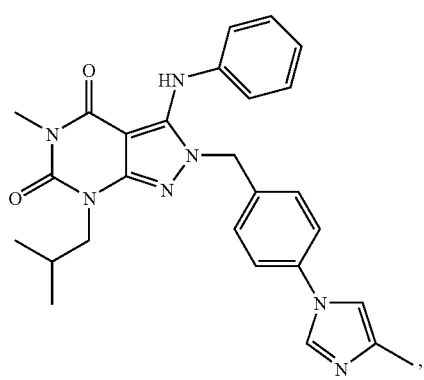
36
-continued
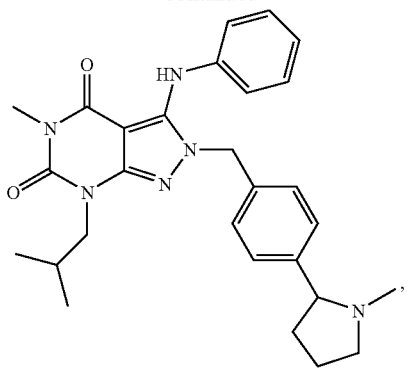
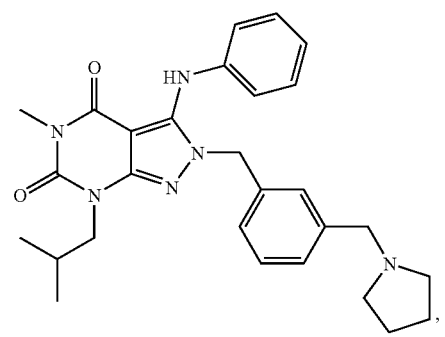
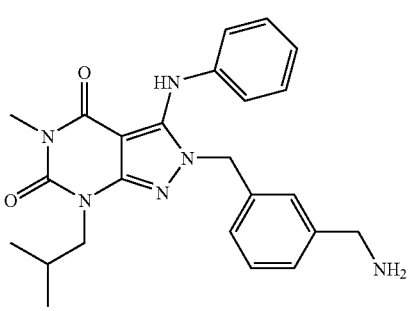
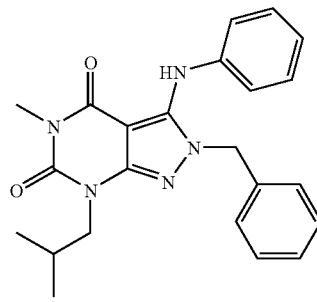
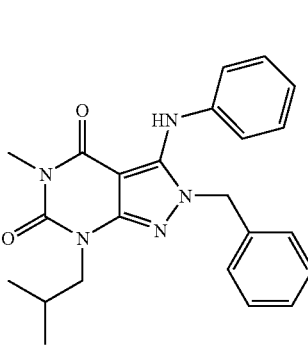

-continued

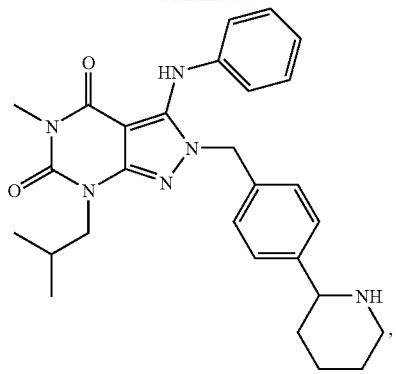

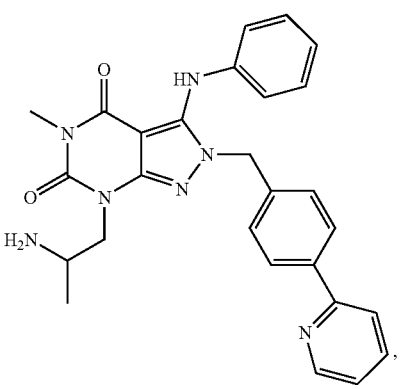

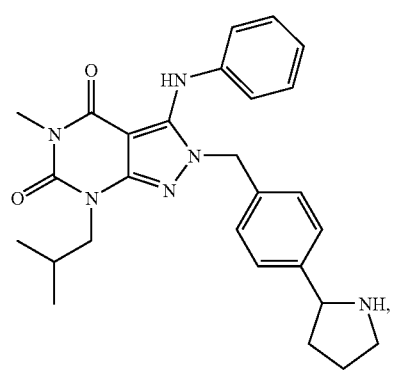

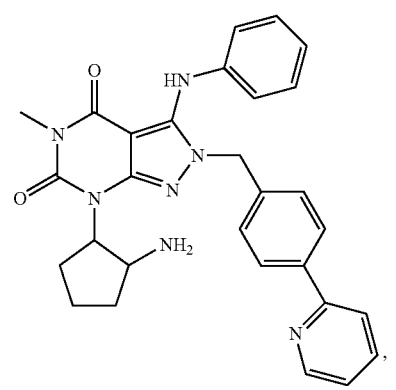

-continued

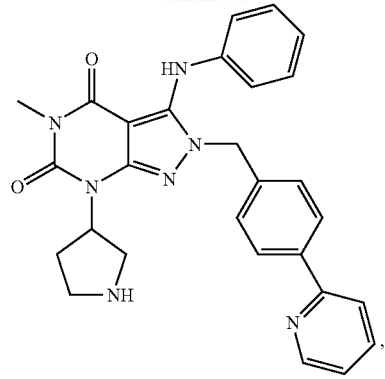

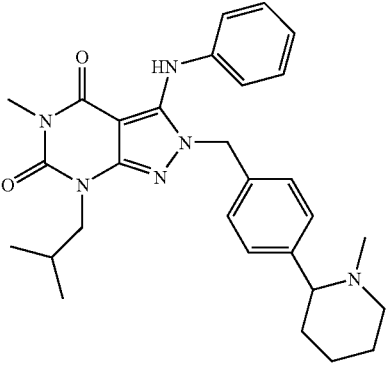

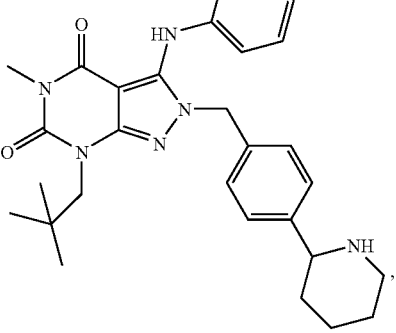

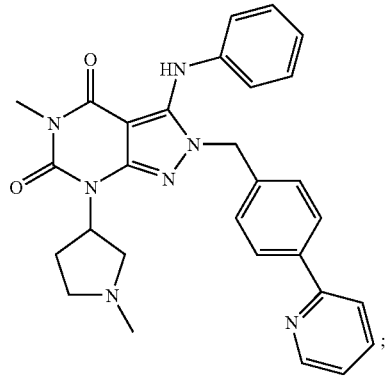

5.24 Any one of the preceding formulae wherein the compounds inhibit phosphodiesterase-mediated (e.g., PDE1-mediated, especially PDE1B-mediated) hydrolysis of cGMP, e.g., with an $IC_{50}$ of less than 1 μM, preferably less than preferably less than 250 nM, preferably less than 50 nM, more preferably less than 25 nM in an immobilized-metal affinity particle reagent PDE assay, for example, as described in Example 19, in free, salt or prodrug form.

In a preferred embodiment, the Compound of the Invention is a compound selected from formula 5.23.

If not otherwise specified or clear from context, the following terms herein have the following meanings:

(a) "Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.

(b) "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy.

(c) "Heterocycloalkyl" refers to a $C_{3-6}$cycloalkyl containing at least one or more heteroatom selected from a group consisting of N, O and S. Examples of heterocycloalkyl include, but are not limited to, oxetane, pyrrolidine, 3,4-dihydro-2H-pyrrole and tetrahydro-2H-pyran.

(d) "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

(e) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

(f) For ease of reference, the atoms on the pyrazolo-pyrimidine core of the Compounds of the Invention are numbered in accordance with the numbering depicted in Formula I, II or III, unless otherwise noted.

Compounds of the Invention herein refer to 1- or 2- or 7-(substituted)-3-(optionally hetero)arylamino-[1H,2H]-pyrazolo[3,4-d]pyrimidine-4,6(5H,7H)-dione derivative, Compounds of Formula Q, Q-I, I, Q-II, II, Q-III, III and/or any of Formulae 1.1-1.97, 2.1-2.39, 3.1-3.39, 4.1-4.44, and/or 5.1-5.24, which may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention may in some cases also exist in prodrug form. A prodrug form is compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. As will be appreciated the term thus embraces conventional pharmaceutical prodrug forms.

The invention also provides methods of making the Compounds of the Invention, novel intermediates useful for making Compounds of the Invention, and methods of using the Compounds of the Invention for treatment of diseases and disorders as set forth below (especially treatment of diseases characterized by reduced dopamine D1 receptor signaling activity, such as Parkinson's disease, Tourette's Syndrome, Autism, fragile X syndrome, ADHD, restless leg syndrome, depression, cognitive impairment of schizophrenia, narcolepsy and diseases that may be alleviated by the enhancement of progesterone-signaling such as female sexual dysfunction).

In another embodiment, the invention also provides a pharmaceutical composition comprising a Compound of the Invention in free, pharmaceutically acceptable salt or prodrug form, in admixture with a pharmaceutically acceptable carrier.

DETAILED DESCRIPTION OF THE INVENTION

Methods of Making Compounds of the Invention

The compounds of the Invention and their pharmaceutically acceptable salts may be made using the methods as described and exemplified herein and by methods similar thereto and by methods known in the chemical art. Such methods include, but are not limited to, those described below. If not commercially available, starting materials for these processes may be made by procedures, which are selected from the chemical art using techniques which are similar or analogous to the synthesis of known compounds. All references cited herein are hereby incorporated in their entirety by reference.

The Compounds of the Invention include their enantiomers, diastereoisomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

Melting points are uncorrected and (dec) indicates decomposition. Temperature are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is in the delta values of major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

| Terms and abbreviations: | |
| --- | --- |
| BuLi = | n-butyllithium |
| Bu$^t$OH = | tert-butyl alcohol, |
| CAN = | ammonium cerium (IV) nitrate, |
| DIPEA = | diisopropylethylamine, |
| DMF = | N,N-dimethylforamide, |
| DMSO = | dimethyl sulfoxide, |
| Et$_2$O = | diethyl ether, |
| EtOAc = | ethyl acetate, |
| equiv. = | equivalent(s), |
| h = | hour(s), |
| HPLC = | high performance liquid chromatography, |
| K$_2$CO$_3$ = | potassium carbonate, |
| LDA = | lithium diisopropylamide |
| MeOH = | methanol, |
| NaHCO$_3$ = | sodium bicarbonate, |
| NBS = | N-bromosuccinimide |
| NCS = | N-chlorosuccinimide |
| NH$_4$OH = | ammonium hydroxide, |
| Pd$_2$(dba)$_3$ = | tris[dibenzylideneacetone]dipalladium(0) |
| PMB = | p-methoxybenzyl, |
| POCl$_3$ = | phosphorous oxychloride, |
| SOCl$_2$ = | thionyl chloride, |
| TFA = | trifluoroacetic acid, |
| THF = | tetrahedrofuran. |

The synthetic methods in this invention are illustrated below. The significances for the R groups are as set forth above for formula Q, Q-I, I, Q-II, II, Q-III or III unless otherwise indicated.

In an aspect of the invention, intermediate compounds of formula IIb can be synthesized by reacting a compound of formula IIa with a dicarboxylic acid, acetic anhydride and acetic acid mixing with heat for about 3 hours and then cooled:

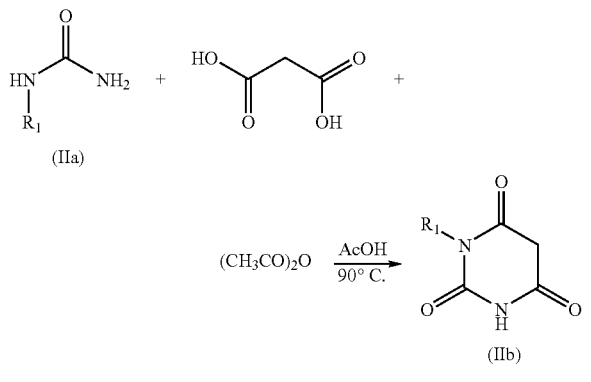

wherein $R_1$ is H or $C_{1-4}$alkyl [e.g., methyl].

Intermediate IIc can be prepared by for example reacting a compound of IIb with for example a chlorinating compound such as POCl$_3$, sometimes with small amounts of water and heated for about 4 hours and then cooled:

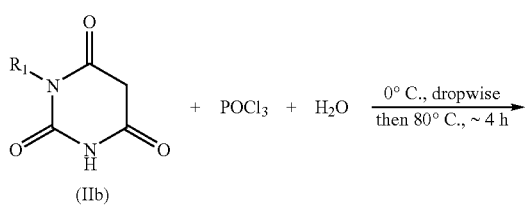

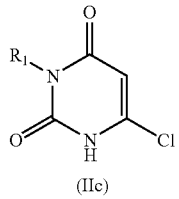

Intermediate IId may be formed by reacting a compound of IIc with for example a P$^1$-L in a solvent such as DMF and a base such as K$_2$CO$_3$ at room temperature or with heating:

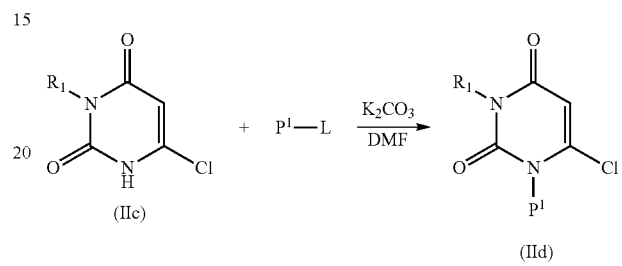

wherein P$^1$ is a protective group [e.g., p-methoxybenzyl group (PMB)]; L is a leaving group such as a halogen, mesylate, or tosylate.

Intermediate IIe may be prepared by reacting a compound of IId with hydrazine or hydrazine hydrate in a solvent such as methanol and refluxed for about 4 hours and then cooled:

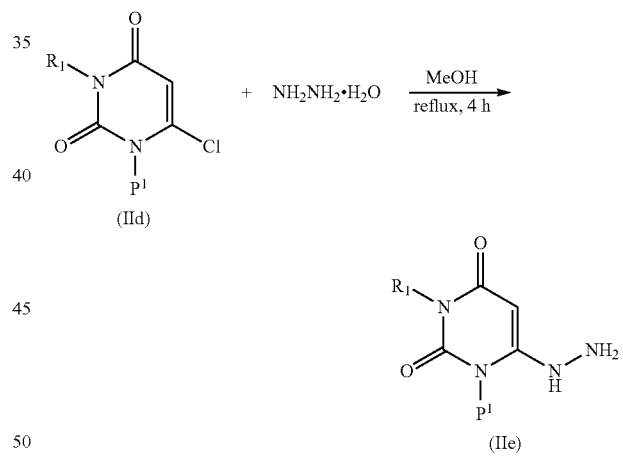

Intermediate IIf can be synthesized by reacting a compound of IIe with for example an aryl isothiocyanate or isocyanate in a solvent such as DMF and heated at 110° C. for about 2 days and then cooled:

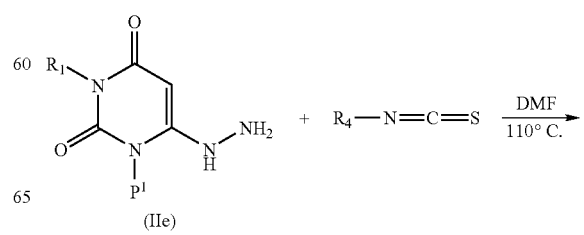

-continued

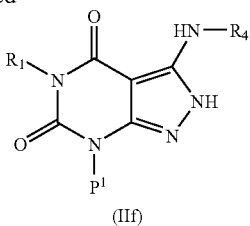

(IIf)

wherein $R_4$ is (hetero)aryl or (hetero)arylmethyl [e.g., phenyl or benzyl].

Intermediate IIg may be formed by reacting a compound of IIf with for example a $R_3$-L in a solvent such as DMF and a base such as $K_2CO_3$ at room temperature or with heating:

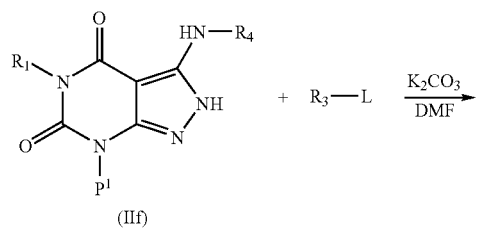

wherein $R_3$ is as defined previously [e.g. -D-E-F or moiety of Formula A]; L is a leaving group such as a halogen, mesylate, or tosylate.

Intermediate IIh may be synthesized from a compound of IIg by removing the protective group $P^1$ with an appropriate method. For example, if $P^1$ is a p-methoxybenzyl group, then it can be removed with $AlCl_3$ in the presence of anisole at room temperature:

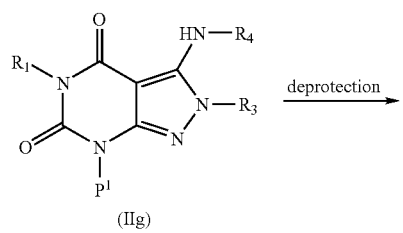

Compound I may be formed by reacting a compound of IIh with for example a $R_2$-L and/or $R_5$-L in a solvent such as DMF and a base such as $K_2CO_3$ at room temperature or with heating:

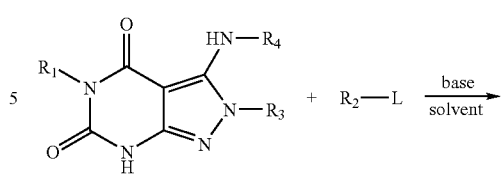

(IIh)

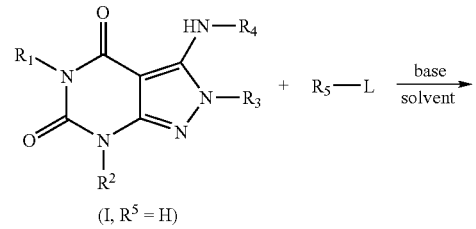

(I, $R^5$ = H)

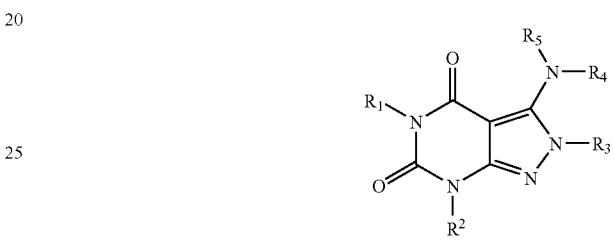

(I)

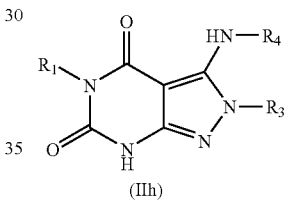

(IIh)

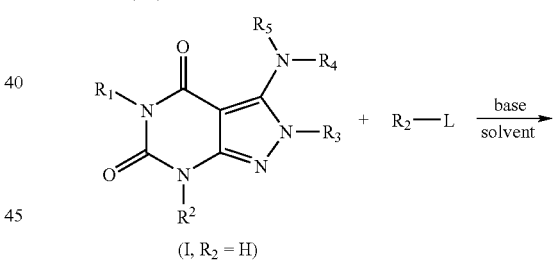

(I, $R_2$ = H)

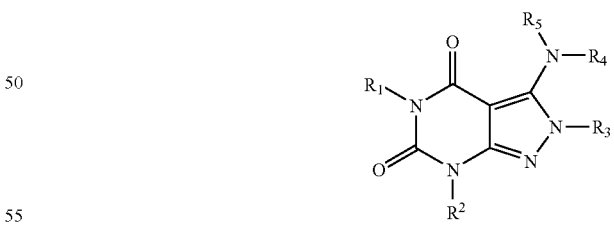

(I)

wherein $R_2$ and $R_5$ are as defined previously [e.g. a cyclopentyl group]; X is a leaving group such as a halogen, mesylate, or tosylate.

There is an alternative approach for the synthesis of compound I.

Intermediate IIIa may be formed by reacting a compound of IIc with for example a $R_2$-L in a solvent such as DMF and a base such as $K_2CO_3$ at room temperature or with heating:

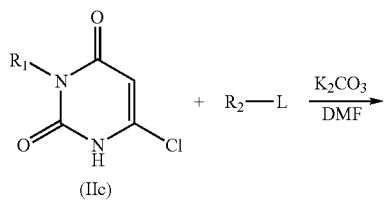

(IIc)

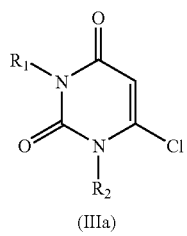

(IIIa)

Intermediate IIIb may be prepared by reacting a compound of IIIa with hydrazine or hydrazine hydrate in a solvent such as methanol and heated for about several hours and then cooled:

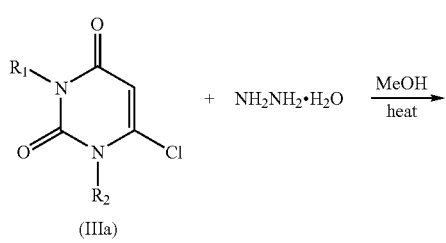

(IIIb)

Intermediate IIIc can be synthesized by reacting a compound of IIIb with for example an aryl isothiocyanate or isocyanate in a solvent such as DMF and heated at 110° C. for about 2 days and then cooled:

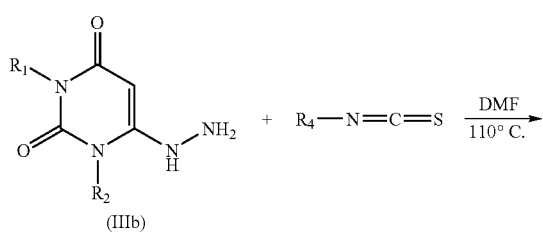

(IIIc)

Compound I may be formed by reacting a compound of IIIc with for example a $R_3$-L in a solvent such as DMF and a base such as $K_2CO_3$ at room temperature or with heating. The obtained product I ($R_5$=H) may further react with for example a $R_5$-L under basic condition to give compound I:

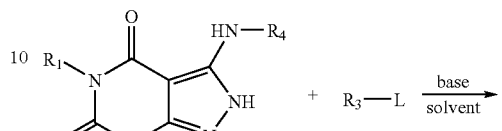

(IIIc)

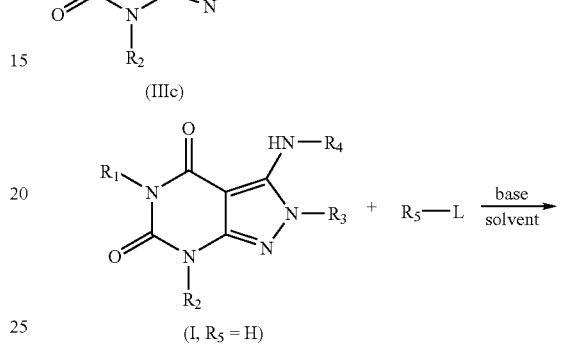

(I, $R_5$ = H)

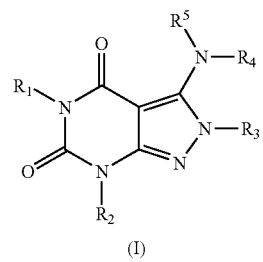

(I)

The third approach for making compound I is described below.

Intermediate IVa may be formed by for example reacting a compound of IIIb with $POCl_3$ and DMF.

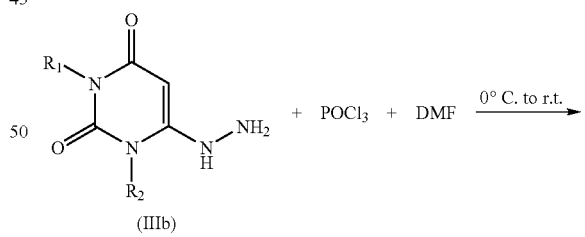

(IIIb)

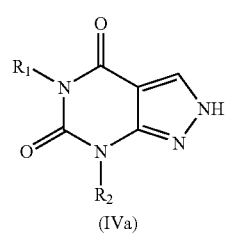

(IVa)

Intermediate IVb may be formed by reacting a compound of IVa with for example a $R_3$-L in a solvent such as DMF and a base such as $K_2CO_3$ at room temperature or with heating.

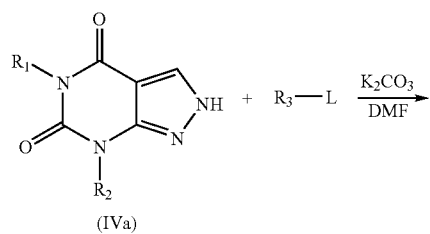 + R₃—L $\xrightarrow{\text{K}_2\text{CO}_3}{\text{DMF}}$ (IVa)

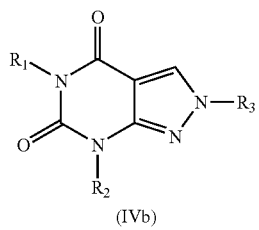

(IVb)

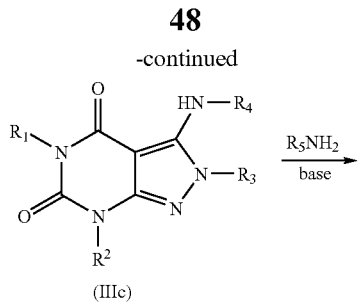 $\xrightarrow{\text{R}_5\text{NH}_2}{\text{base}}$ (IIIc)

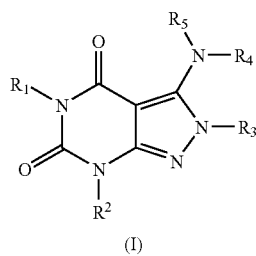

(I)

Intermediate IVc may be formed by reacting a compound of IVb with for example NCS, NBS or I₂ in a solvent such as THF and a base such as LDA or BuLi at low temperature.

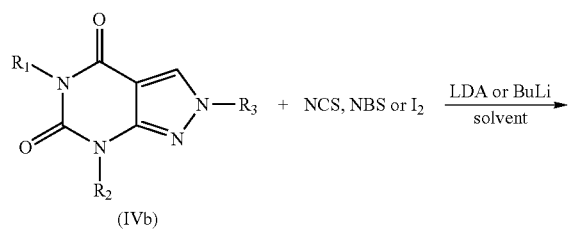 $\xrightarrow{\text{LDA or BuLi}}{\text{solvent}}$ (IVb)

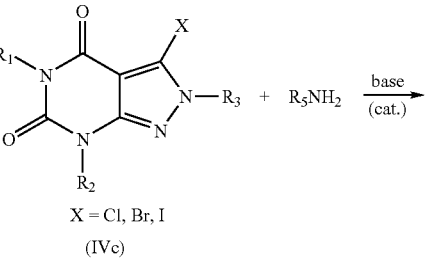 $\xrightarrow[\text{(cat.)}]{\text{base}}$ (IVc) X = Cl, Br, I

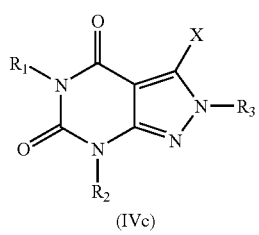

(IVc) X = Cl, Br, I

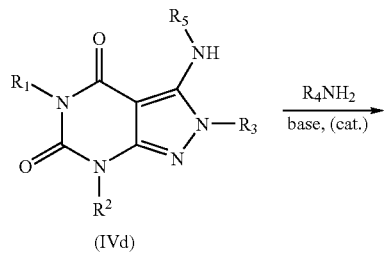 $\xrightarrow[\text{base, (cat.)}]{\text{R}_4\text{NH}_2}$ (IVd)

Compound I may be formed by the amination of IVc, IVd, or IIIc under basic conditions. An appropriate catalyst such as Pd₂(dba)₃ may be required in order to get good yields.

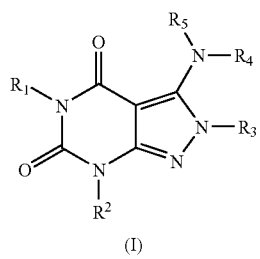

(I)

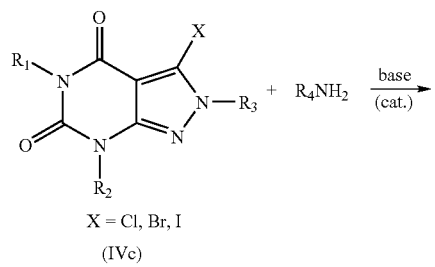 + R₄NH₂ $\xrightarrow[\text{(cat.)}]{\text{base}}$

X = Cl, Br, I
(IVc)

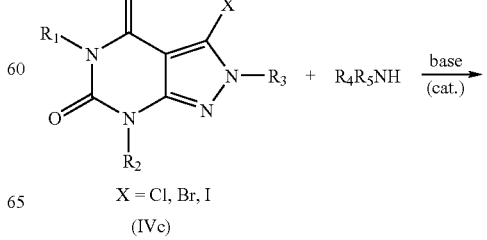 + R₄R₅NH $\xrightarrow[\text{(cat.)}]{\text{base}}$

X = Cl, Br, I
(IVc)

-continued

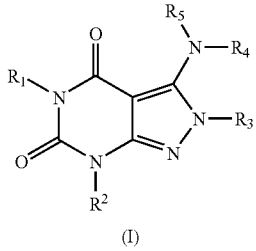

(I)

The Compounds of the Invention, wherein $R_3$ is a (heterocycloalkyl)-benzyl, e.g., 4-(piperidin-2-yl)benzyl, may also be prepared by reacting Intermediate (I) with an N-protected (heterocycloalkyl)phenyl)methanol, e.g., BOC-protected tert-butyl 2-(4-(hydroxymethyl)phenyl)piperidine-1-carboxylate, in the presence of, e.g., triphenyl phosphine. The product can then be deprotected to get the Compound of the Invention.

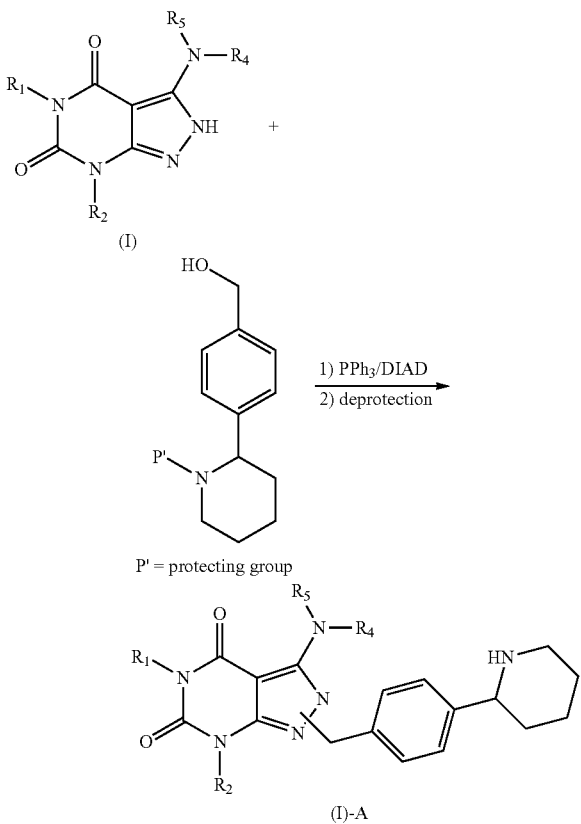

The Compounds of the Invention, wherein $R_3$ is a (alkyl-heterocycloalkyl)-benzyl, e.g., 4-(1-methylpiperidin-2-yl) benzyl, may be prepared by subjecting compound (I)-A above to reductive alkylation.

The invention thus provides methods of making Compounds of the Invention as described above, for example, comprising
  (i) reacting a 2H-pyrazolo[3,4-d]pyrimidine-4,6(5H,7H)-dione of Formula with a compound of formula L-$R_3$ wherein L is a leaving group, e.g., halogen, mesylate, or tosylate, and $R_3$ is as hereinbefore described, for example wherein $R_3$ is D-E-F or $R_3$ is a moiety of Formula A e.g., under basic conditions, for example wherein the 2H-pyrazolo[3,4-d]pyrimidine-4,6(5H, 7H)-dione is a compound of Formula IIIc:

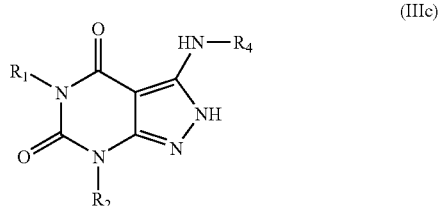

(IIIc)

wherein $R_1$, $R_2$ and $R_4$ are as defined above or $R_2$ is of formula G-J, e.g., with reference to Formula Q, Q-I, I, Q-II, II, Q-III or III; and/or
  (ii) reacting a 2H-pyrazolo[3,4-d]pyrimidine-4,6(5H,7H)-dione with a compound of formula L-$R_2$ wherein L is a leaving group, e.g., halogen, mesylate, or tosylate, and $R_2$ is as hereinbefore described, for example wherein $R^2$ is isobutyl, methylpyrrolidine, or methyloxetane, e.g., under basic conditions, for example wherein the 2H-pyrazolo[3,4-d]pyrimidine-4,6(5H,7H)-dione is a compound of Formula IIh:

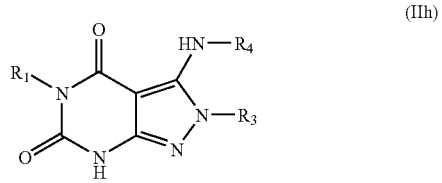

(IIh)

wherein $R_1$, $R_3$ and $R_4$ are as defined above, e.g., with reference to Formula I.

Methods of Using Compounds of the Invention

The Compounds of the Invention are useful in the treatment of diseases characterized by disruption of or damage to cAMP and cGMP mediated pathways, e.g., as a result of increased expression of PDE1 or decreased expression of cAMP and cGMP due to inhibition or reduced levels of inducers of cyclic nucleotide synthesis, such as dopamine and nitric oxide (NO). By preventing the degradation of cAMP and cGMP by PDE1B, thereby increasing intracellular levels of cAMP and cGMP, the Compounds of the Invention potentiate the activity of cyclic nucleotide synthesis inducers.

The invention provides methods of treatment of any one or more of the following conditions:
  (i) Neurodegenerative diseases, including Parkinson's disease, restless leg, tremors, dyskinesias, Huntington's disease, Alzheimer's disease, and drug-induced movement disorders;
  (ii) Mental disorders, including depression, attention deficit disorder, attention deficit hyperactivity disorder, bipolar illness, anxiety, sleep disorders, e.g., narcolepsy, cognitive impairment, dementia, Tourette's syndrome, autism, fragile X syndrome, psychostimulant withdrawal, and drug addiction;
  (iii) Circulatory and cardiovascular disorders, including cerebrovascular disease, stroke, congestive heart disease, hypertension, pulmonary hypertension, and sexual dysfunction;
  (iv) Respiratory and inflammatory disorders, including asthma, chronic obstructive pulmonary disease, and allergic rhinitis, as well as autoimmune and inflammatory diseases;

(v) Any disease or condition characterized by low levels of cAMP and/or cGMP (or inhibition of cAMP and/or cGMP signaling pathways) in cells expressing PDE1; and/or (vi) Any disease or condition characterized by reduced dopamine D1 receptor signaling activity, comprising administering an effective amount of a Compound of the Invention, e.g., a compound according to any of Formula I, II or III or any of 2.1-2.39, 3.1-3.39 or 4.1-4.44, to a human or animal patient in need thereof. Similarly, the Invention also provides methods of treating one or more of the conditions above, e.g., (i) Neurodegenerative diseases, including Parkinson's disease, restless leg, tremors, dyskinesias, Huntington's disease, Alzheimer's disease, and drug-induced movement disorders;

(ii) Mental disorders, including depression, attention deficit disorder, attention deficit hyperactivity disorder, bipolar illness, anxiety, sleep disorders, e.g., narcolepsy, cognitive impairment, dementia, Tourette's syndrome, autism, fragile X syndrome, psychostimulant withdrawal, and drug addiction;

(iii) Circulatory and cardiovascular disorders, including cerebrovascular disease, stroke, congestive heart disease, hypertension, pulmonary hypertension, and sexual dysfunction;

(iv) Respiratory and inflammatory disorders, including asthma, chronic obstructive pulmonary disease, and allergic rhinitis, as well as autoimmune and inflammatory diseases;

(v) Any disease or condition characterized by low levels of cAMP and/or cGMP (or inhibition of cAMP and/or cGMP signaling pathways) in cells expressing PDE1; and/or (vi) Any disease or condition characterized by reduced dopamine D1 receptor signaling activity, comprising administering an effective amount of a Compound of the Invention, e.g., a compound according to any of Formula Q, Q-I, Q-II or Q-III or any of Formulae 1.1-1.97 or 5.1-5.24, to a human or animal patient in need thereof.

In an especially preferred embodiment, the invention provides methods of treatment or prophylaxis for narcolepsy. In this embodiment, PDE1 Inhibitors may be used as a sole therapeutic agent, but may also be used in combination or for co-administration with other active agents. Thus, the invention further comprises a method of treating narcolepsy comprising administering simultaneously, sequentially, or contemporaneously administering therapeutically effective amounts of (i) a PDE1 Inhibitor, e.g., a compound according to any of Formulae I, II or III or any of 2.1-2.39, 3.1-3.39 or 4.1-4.44, and (ii) a compound to promote wakefulness or regulate sleep, e.g., selected from (a) central nervous system stimulants-amphetamines and amphetamine like compounds, e.g., methylphenidate, dextroamphetamine, methamphetamine, and pemoline; (b) modafinil, (c) antidepressants, e.g., tricyclics (including imipramine, desipramine, clomipramine, and protriptyline) and selective serotonin reuptake inhibitors (including fluoxetine and sertraline); and/or (d) gamma hydroxybutyrate (GHB).

to a human or animal patient in need thereof.

The invention also methods of treatment or prophylaxis for narcolepsy comprising comprises a method of treating narcolepsy comprising administering an effective amount of a Compound of the Invention, e.g., a compound according to any of Formula Q, Q-I, Q-II or Q-III or any of Formulae 1.1-1.97 or 5.1-5.24, to a human or animal patient in need thereof. The invention further comprises a method of treating narcolepsy comprising administering simultaneously, sequentially, or contemporaneously administering therapeutically effective amounts of (i) a PDE1 Inhibitor, e.g., a compound according to any of Q, Q-I, Q-II or Q-III or any of Formulae 1.1-1.97 or 5.1-5.24, and (ii) a compound to promote wakefulness or regulate sleep, e.g., selected from (a) central nervous system stimulants-amphetamines and amphetamine like compounds, e.g., methylphenidate, dextroamphetamine, methamphetamine, and pemoline; (b) modafinil, (c) antidepressants, e.g., tricyclics (including imipramine, desipramine, clomipramine, and protriptyline) and selective serotonin reuptake inhibitors (including fluoxetine and sertraline); and/or (d) gamma hydroxybutyrate (GHB).

to a human or animal patient in need thereof.

In another embodiment, the invention further provides methods of treatment or prophylaxis of a condition which may be alleviated by the enhancement of the progesterone signaling comprising administering an effective amount of a Compound of the Invention, e.g., a compound according to any of Formula I, II or III or any of 2.1-2.39, 3.1-3.39 or 4.1-4.44, to a human or animal patient in need thereof. Similarly, an effective amount of a Compound of Formula Q, Q-I, Q-II or Q-III or any of 1.1-1.97 or 5.1-5.24 may be administered to a human or animal patient in need thereof for the treatment or prophylaxis of a condition which may be alleviated by the enhancement of the progesterone signaling. Disease or condition that may be ameliorated by enhancement of progesterone signaling include, but are not limited to, female sexual dysfunction, secondary amenorrhea (e.g., exercise amenorrhoea, anovulation, menopause, menopausal symptoms, hypothyroidism), pre-menstrual syndrome, premature labor, infertility, for example infertility due to repeated miscarriage, irregular menstrual cycles, abnormal uterine bleeding, osteoporosis, autoimmune disease, multiple sclerosis, prostate enlargement, prostate cancer, and hypothyroidism. For example, by enhancing progesterone signaling, the PDE 1 inhibitors may be used to encourage egg implantation through effects on the lining of uterus, and to help maintain pregnancy in women who are prone to miscarriage due to immune response to pregnancy or low progesterone function. The novel PDE 1 inhibitors, e.g., as described herein, may also be useful to enhance the effectiveness of hormone replacement therapy, e.g., administered in combination with estrogen/estradiol/estriol and/or progesterone/progestins in postmenopausal women, and estrogen-induced endometrial hyperplasia and carcinoma. The methods of the invention are also useful for animal breeding, for example to induce sexual receptivity and/or estrus in a nonhuman female mammal to be bred.

In this embodiment, PDE 1 Inhibitors may be used in the foregoing methods of treatment or prophylaxis as a sole therapeutic agent, but may also be used in combination or for co-administration with other active agents, for example in conjunction with hormone replacement therapy. Thus, the invention further comprises a method of treating disorders that may be ameliorated by enhancement of progesterone signaling comprising administering simultaneously, sequentially, or contemporaneously administering therapeutically effective amounts of (i) a PDE 1 Inhibitor, e.g., a compound according to any of Formula I, II or III or any of 2.1-2.39, 3.1-3.39 or 4.1-4.44;

(ii) a hormone, e.g., selected from estrogen and estrogen analogues (e.g., estradiol, estriol, estradiol esters) and progesterone and progesterone analogues (e.g., progestins)

to a human or animal patient in need thereof.

In another embodiment, PDE 1 Inhibitors of Formula Q, Q-I, Q-II or Q-III or any of 1.1-1.97 or 5.1-5.24 may be used in the foregoing methods of treatment or prophylaxis as a sole therapeutic agent, but may also be used in combination or for co-administration with other active agents, for example in conjunction with hormone replacement therapy. Thus, the invention further comprises a method of treating disorders that may be ameliorated by enhancement of progesterone signaling comprising administering simultaneously, sequentially, or contemporaneously administering therapeutically effective amounts of (i) a PDE 1 Inhibitor, e.g., a compound according to any of Formula Q, Q-I, Q-II or Q-III or any of 1.1-1.97 or 5.1-5.24;

(ii) a hormone, e.g., selected from estrogen and estrogen analogues (e.g., estradiol, estriol, estradiol esters) and progesterone and progesterone analogues (e.g., progestins)

to a human or animal patient in need thereof.

The invention also provides a method for enhancing or potentiating dopamine D1 intracellular signaling activity in a cell or tissue comprising contacting said cell or tissue with an amount of a Compound of the Invention, e.g., a Compound of Formula Q, Q-I, I, Q-II, II, Q-III, III or any of 1.1-1.97, 2.1-2.39, 3.1-3.39, 4.1-4.44 or 5.1-5.24 sufficient to inhibit PDE1B activity.

The invention also provides a method for enhancing or potentiating progesterone signaling activity in a cell or tissue comprising contacting said cell or tissue with an amount of a Compound of the Invention, e.g., a Compound of Formula Q, Q-I, I, Q-II, II, Q-III, III or any of 1.1-1.97, 2.1-2.39, 3.1-3.39, 4.1-4.44 or 5.1-5.24 sufficient to inhibit PDE1B activity.

The invention also provides a method for treating a PDE1-related, especially PDE1B-related disorder, a dopamine D1 receptor intracellular signaling pathway disorder, or disorders that may be alleviated by the enhancement of the progesterone signaling pathway in a patient in need thereof comprising administering to the patient an effective amount of a Compound of the Invention, e.g., a Compound of Formula Q, Q-I, I, Q-II, II, Q-III, III or any of 1.1-1.97, 2.1-2.39, 3.1-3.39, 4.1-4.44 or 5.1-5.24, that inhibits PDE1B, wherein PDE1B activity modulates phosphorylation of DARPP-32 and/or the GluR1 AMPA receptor.

The present invention also provides (i) a Compound of the Invention, e.g., a Compound of Formula Q, Q-I, I, Q-II, II, Q-III, III or any of 1.1-1.97, 2.1-2.39, 3.1-3.39, 4.1-4.44 or 5.1-5.24, for use as a pharmaceutical, for example for use in any method or in the treatment of any disease or condition as hereinbefore set forth, (ii) the use of a Compound of the Invention, e.g., a Compound of Formula Q, Q-I, I, Q-II, II, Q-III, III or any of 1.1-1.97, 2.1-2.39, 3.1-3.39, 4.1-4.44 or 5.1-5.24, in the manufacture of a medicament for treating any disease or condition as hereinbefore set forth, (iii) a pharmaceutical composition comprising a Compound of the Invention, e.g., a Compound of Formula Q, Q-I, I, Q-II, II, Q-III, III or any of 1.1-1.97, 2.1-2.39, 3.1-3.39, 4.1-4.44 or 5.1-5.24, in combination or association with a pharmaceutically acceptable diluent or carrier, and (iv) a pharmaceutical composition comprising a Compound of the Invention, e.g., a Compound of Formula Q, Q-I, I, Q-II, II, Q-III, III or any of 1.1-1.97, 2.1-2.39, 3.1-3.39, 4.1-4.44 or 5.1-5.24, in combination or association with a pharmaceutically acceptable diluent or carrier for use in the treatment of any disease or condition as hereinbefore set forth.

The words "treatment" and "treating" are to be understood accordingly as embracing prophylaxis and treatment or amelioration of symptoms of disease as well as treatment of the cause of the disease Compounds of the Invention, e.g., a Compound of Formula Q, Q-I, I, Q-II, II, Q-III, III or any of 1.1-1.97, 2.1-2.39, 3.1-3.39, 4.1-4.44 or 5.1-5.24, are in particular useful for the treatment of Parkinson's disease, narcolepsy and female sexual dysfunction.

Compounds of the Invention, e.g., a Compound of Formula Q, Q-I, I, Q-II, II, Q-III, III or any of 1.1-1.97, 2.1-2.39, 3.1-3.39, 4.1-4.44 or 5.1-5.24, may be used as a sole therapeutic agent, but may also be used in combination or for co-administration with other active agents. For example, as Compounds of the Invention potentiate the activity of D1 agonists, such as dopamine, they may be simultaneously, sequentially, or contemporaneously administered with conventional dopaminergic medications, such as levodopa and levodopa adjuncts (carbidopa, COMT inhibitors, MAO-B inhibitors), dopamine agonists, and anticholinergics, e.g., in the treatment of a patient having Parkinson's disease. In addition, the novel PDE 1 inhibitors, e.g., as described herein, may also be administered in combination with estrogen/estradiol/estriol and/or progesterone/progestins to enhance the effectiveness of hormone replacement therapy or treatment of estrogen-induced endometrial hyperplasia or carcinoma.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Invention, together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

EXAMPLES

Example 1

7-isopropyl-5-methyl-3-(phenylamino)-2-(4-(pyridin-2-yl)benzyl)-2H-pyrazolo[3,4-d]pyrimidine-4,6(5H,7H)-dione

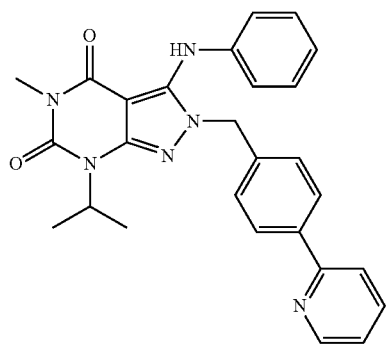 [SMILES: CC(C)n1c(=O)n(C)c(=O)c2c(Nc3ccccc3)n(Cc3ccc(-c4ccccn4)cc3)nc21]

Methylethylketone (1.2 mL) is added into a 0.5~5 mL reaction vessel containing 5-methyl-3-(phenylamino)-2-(4-(pyridin-2-yl)benzyl)-2H-pyrazolo[3,4-d]pyrimidine-4,6(5H,7H)-dione (25 mg, 0.0589 mmol), isopropyl iodide (0.0707 mmol) and $Cs_2CO_3$ (0.0707 mmol). The sealed vessel is put onto a Biotage Microwave instrument and the microwave reaction is carried out at 140° C. for 1 hour. The obtained crude product is then purified by silica-gel flash chromatography to give pure product MS (ESI) m/z 467.2 $[M+H]^+$.

Example 2

2-(4-(4,6-dimethylpyridin-2-yl)benzyl)-7-isobutyl-5-methyl-3-(phenylamino)-2H-pyrazolo[3,4-d]pyrimidine-4,6(5H,7H)-dione

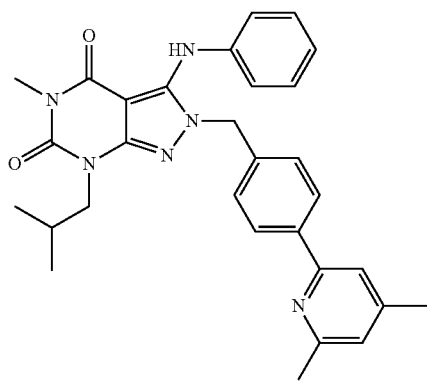

(a) 1-Methylpyrimidine-2,4,6(1H,3H,5H)-trione

To a solution of malonic acid (80 g, 0.79 mol) and methylurea (50 g, 0.68 mol) in 180 ml of acetic acid at 70° C., acetic anhydride (130 ml, 1.37 mol) is added slowly. After the completion of the addition, the reaction mixture is stirred at 90° C. for 3 hours, and then cooled to room temperature. The solvent is removed under reduced pressure, and the residue is treated with 350 mL of ethanol to precipitate out yellowish solid. The solid is recrystallized from ethanol to give 63.1 g product as crystalline solids (Yield: 65.8%). m.p.=131.2-133.1° C. [Lit.[1]: m.p.=130-131.5° C.].

(b) 6-Chloro-3-methylpyrimidine-2,4(1H,3H)-dione

Water (2.7 mL) is added dropwise to a suspension of 1-methylpyrimidine-2,4,6(1H,3H,5H)-trione (14.2 g, 100 mol) in $POCl_3$ (95 mL) at 0° C. The reaction mixture is then heated at 80° C. for 5 hours. The resulting brownish solution is cooled, and $POCl_3$ is evaporated under reduced pressure. The residue is treated with MeOH, and the obtained solid is recrystallized from ethanol to give 11.5 g product (Yield: 71.6%). m.p.=279-282° C. (dec) [Lit.[2]: 280-282° C.]. $^1$H NMR (400 MHz, DMSO-$d_6$) δ3.10 (S, 3H), 5.90 (S, 1H), 12.4 (br, 1H).

(c) 6-Chloro-1-isobutyl-3-methylpyrimidine-2,4(1H,3H)-dione

A mixture of 6-chloro-3-methylpyrimidine-2,4(1H,3H)-dione (3 g, 18.8 mmol), isobutyl iodide (5 mL, 43.5 mmol) and potassium carbonate (5.3 g, 38.4 mmol) in anhydrous DMF (200 mL) is heated at 50° C. for 8 hours. Additional isobutyl iodide (4.3 mL, 37.5 mmol) is added, and the reaction mixture heated at 50° C. for 24 hours. After hot filtration, the filtrate is evaporated to dryness under reduced pressure. The obtained oil is further purified by silica-gel flash chromatography to give 2.1 g of pure product (Yield: 52%).

(d) 6-Hydrazinyl-1-isobutyl-3-methylpyrimidine-2,4(1H,3H)-dione

To a solution of 6-chloro-1-isobutyl-3-methylpyrimidine-2,4(1H,3H)-dione (2.0 g 9.3 mmol) in EtOH (8 mL), hydrazine monohydrate (1.3 mL) in EtOH (3 mL) is added slowly. The reaction mixture is refluxed for 5 hours, and then cooled. A large amount of AcOEt is added into the reaction mixture, and then cooled and filtered to give 1.95 g of product as yellowish solids (Yield: 100%).

(e) 7-Isobutyl-5-methyl-3-(phenylamino)-2H-pyrazolo[3,4-d]pyrimidine-4,6(5H,7H)-dione Phenyl isothiocyanate (0.17 mL, 1.4 mmol) is added to a solution of 6-hydrazinyl-1-isobutyl-3-methylpyrimidine-2,4(1H,3H)-dione (31 mg, 0.47 mmol) in DMF (10 mL). The reaction mixture is heated at 120° C. for 6 hours, and then evaporated to remove solvent under reduced pressure. The residue is further purified by silica-gel flash chromatography to give 20 mg of product (Yield: 41%). $^1$H NMR (400 MHz, DMSO-$d_6$) δ0.95 (s, 3H), 0.97 (s, 3H), 2.30 (m, 1H), 3.37 (s, 3H), 3.77 (d, 2H), 7.16-7.43 (m, 5H), 7.61 (s, 1H). MS (FAB) m/z 314.3 $[M+H]^+$.

(f) 7-isobutyl-5-methyl-3-(phenylamino)-2-(4-(4,4,5,5-tetramethyl-1,3,2-dioxaborolan-2-yl)benzyl)-2H-pyrazolo[3,4-d]pyrimidine-4,6(5H,7H)-dione A mixture of 7-isobutyl-5-methyl-3-(phenylamino)-1H-pyrazolo[3,4-d]pyrimidine-4,6(5H,7H)-dione (12.0 mg, 0.0383 mmol), 2-(4-(bromomethyl)phenyl)-4,4,5,5-tetramethyl-1,3,2-dioxaborolane (0.0383 mmol) and potassium carbonate (5.3 mg, 0.0383 mmol) in acetone (2.5 mL) is stirred at room temperature overnight. The solvent is evaporated under reduced pressure. The residue is directly purified by chromatography to give 7.0 mg product as white solids (Yield: 38.0%). MS (ESI) m/z 530.3 [M+H]⁺.

(g) 2-(4-(4,6-dimethylpyridin-2-yl)benzyl)-7-isobutyl-5-methyl-3-(phenylamino)-2H-pyrazolo[3,4-d]pyrimidine-4,6(5H,7H)-dione A mixture of 7-isobutyl-5-methyl-3-(phenylamino)-2-(4-(4,4,5,5-tetramethyl-1,3,2-dioxaborolan-2-yl)benzyl)-2H-pyrazolo[3,4-d]pyrimidine-4,6(5H,7H)-dione (41 mg, 0.077 mmol), 2-bromo-4,6-dimethylpyridine (14.3 mg, 0.077), tetrakis(triphenylphosphine)palladium(0) (3 mg), and 1M NaHCO₃ aqueous solution (116 uL) in dioxane (350 μL) was heated at 100° C. for 4 hours, and then cooled to room temperature. The mixture was filtered through a 0.45 μm microfilter, and then purified by a semi-preparative HPLC to give pure product as a white powder. MS (ESI) m/z 509.2 [M+H]⁺

Example 3

2-(biphenyl-4-ylmethyl)-7-isobutyl-5-methyl-3-(pyridin-4-ylamino)-2H-pyrazolo[3,4-d]pyrimidine-4,6(5H,7H)-dione

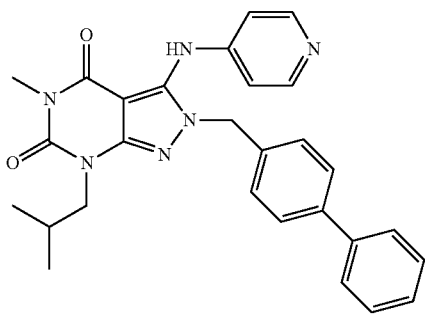 [SMILES: CC(C)Cn1c(=O)n(C)c(=O)c2c(Nc3ccncc3)n(Cc3ccc(-c4ccccc4)cc3)nc21]

(a) 7-(4-methoxybenzyl)-5-methyl-1H-pyrazolo[3,4-d]pyrimidine-4,6(5H,7H)-dione

To a solution of 6-hydrazinyl-1-(4-methoxybenzyl)-3-methylpyrimidine-2,4(1H,3H)-dione (4.0 g, 14.5 mmol) in anhydrous DMF (200 mL) is added POCl₃ (16 mL) dropwise with IPA-dry ice bath cooling. After the completion of the addition, the mixture is allowed to warm up to room temperature and stirred at r.t. overnight. DMF is removed under reduced pressure, and the residue is treated with cold water very carefully. The generated precipitate is filtered, washed with water to give pure product as white solids (3.74 g, yield: 90%). MS (ESI) m/z 287.1 [M+H]⁺

(b) 2-(biphenyl-4-ylmethyl)-7-(4-methoxybenzyl)-5-methyl-2H-pyrazolo[3,4-d]pyrimidine-4,6(5H,7H)-dione A mixture of 7-(4-methoxybenzyl)-5-methyl-1H-pyrazolo[3,4-d]pyrimidine-4,6(5H,7H)-dione (1 g, 3.49 mmol), biphenylmethyl bromide (0.91 g, 3.67 mmol) and K₂CO₃ (1.45 g, 10.5 mmol) in DMF (25 mL) is stirred at r.t. overnight. After DMF is removed under reduced pressure, the residue is diluted with water (100 mL), and then extracted with CH₂Cl₂ four times. The combined organic phase is washed water twice, evaporated to dryness to give 1.6 g of crude product. MS (ESI) m/z 453.2 [M+H]⁺.

(c) 2-(biphenyl-4-ylmethyl)-5-methyl-2H-pyrazolo[3,4-d]pyrimidine-4,6(5H,7H)-dione To a solution of 2-(biphenyl-4-ylmethyl)-7-(4-methoxybenzyl)-5-methyl-2H-pyrazolo[3,4-d]pyrimidine-4,6(5H,7H)-dione in CH₂Cl₂ (90 mL) is added TFA (10 mL) slowly at room temperature, followed by adding trifluoromethanesulfonic acid (4 mL) dropwise. After the reaction mixture is stirred at r.t. for 3 hours, solvent is removed under reduced pressure, and the obtained residue is basified by adding cold pre-diluted ammonium hydroxide (NH₃ content, 7%) at 0° C. The mixture is extracted with ethyl acetate four times. The combined organic phase is washed with brine, dried over anhydrous Na₂SO₄, and then filtered. The filtrate is evaporated to dryness to give crude product in almost quantitative yield. MS (ESI) m/z 333.1 [M+H]⁺.

(d) 2-(biphenyl-4-ylmethyl)-7-isobutyl-5-methyl-2H-pyrazolo[3,4-d]pyrimidine-4,6(5H,7H)-dione Methylethylketone (20 mL) is added into a 20 mL reaction vessel containing 52-(biphenyl-4-ylmethyl)-5-methyl-2H-pyrazolo[3,4-d]pyrimidine-4,6(5H,7H)-dione (800 mg, 2.41 mmol), isobutyl iodide (556 μL, 4.81 mmol) and K₂CO₃ (666 mg, 4.81 mmol). The sealed vessel is put onto a Biotage Microwave instrument and the microwave reaction is carried out at 140° C. for 1 hour. After routine workup, 800 mg of product is obtained white solids. MS (ESI) m/z 389.2 [M+H]⁺.

(e) 2-(biphenyl-4-ylmethyl)-3-iodo-7-isobutyl-5-methyl-2H-pyrazolo[3,4-d]pyrimidine-4,6(5H,7H)-dione 2-(biphenyl-4-ylmethyl)-7-isobutyl-5-methyl-2H-pyrazolo[3,4-d]pyrimidine-4,6(5H,7H)-dione (203 mg, 0.523 mmol) is dissolved in anhydrous THF (5 mL), and then cooled to −78° C. 1.8 M solution of LDA in THF (600 uL) is added dropwise with rigorous stirring at −78° C., followed by the addition of iodine (160 mg, 0.63 mmol) in THF. The reaction mixture is stirred at −78° C. for an hour, and then is allowed to warm up to room temperature before quenching. The mixture is poured into saturated NH₄Cl solution, and then extracted with ethyl acetate three times. The combined organic phase is washed with potassium iodide aqueous solution (1 M), water, and then dried over Na₂SO₄. Solvent is removed under reduced vacuum to give crude product was white solids. MS (ESI) m/z 515.1 [M+H]⁺.

(f) 2-(biphenyl-4-ylmethyl)-7-isobutyl-5-methyl-3-(pyridin-4-ylamino)-2H-pyrazolo[3,4-d]pyrimidine-4,6(5H,7H)-dione 2-(biphenyl-4-ylmethyl)-3-iodo-7-isobutyl-5-methyl-2H-pyrazolo[3,4-d]pyrimidine-4,6(5H,7H)-dione (13.6 mg, 0.026 mmol) is dissolved in anhydrous and degassed THF, and then 4-pyridyl amine (13 mg, 0.132 mmol), Pd₂(dba)₃ (12 mg, 0.013 mmol) and Xantphos (9 mg, 0.016 mmol) are added, followed by ᵗBuOK (7.5 mg, 0.065 mmol). The reaction mixture is heated in microwave at 150° C. for 40 minutes.

After cooling and filtration, the filtrate is purified by a semi-preparative HPLC to give product. MS (ESI) m/z 481.2 [M+H]+

Example 4

2-(biphenyl-4-ylmethyl)-7-isobutyl-5-methyl-3-(pyridin-2-ylamino)-2H-pyrazolo[3,4-d]pyrimidine-4,6(5H,7H)-dione

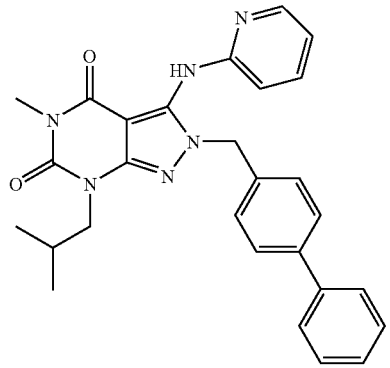 [SMILES: CC(C)Cn1c(=O)n(C)c(=O)c2c(Nc3ccccn3)n(Cc3ccc(-c4ccccc4)cc3)nc21]

The synthesis method is analogous to example 3 wherein 2-(biphenyl-4-ylmethyl)-3-chloro-7-isobutyl-5-methyl-2H-pyrazolo[3,4-d]pyrimidine-4,6(5H,7H)-dioneis is used instead of 2-(biphenyl-4-ylmethyl)-3-iodo-7-isobutyl-5-methyl-2H-pyrazolo[3,4-d]pyrimidine-4,6(5H,7H)-dione, and 2-pyridyl amine is added in step (f) instead of 4-pyridyl amine. MS (ESI) m/z 481.2 [M+H]+.

Example 5

2-(biphenyl-4-ylmethyl)-5-methyl-7-neopentyl-3-(pyridin-4-ylamino)-2H-pyrazolo[3,4-d]pyrimidine-4,6(5H,7H)-dione

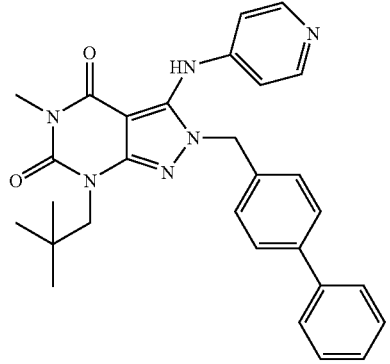 [SMILES: Cn1c(=O)c2c(Nc3ccncc3)n(Cc3ccc(-c4ccccc4)cc3)nc2n(CC(C)(C)C)c1=O]

A mixture of 5-methyl-7-neopentyl-3-(pyridin-4-ylamino)-1H-pyrazolo[3,4-d]pyrimidine-4,6(5H,7H)-dione (20 mg, 0.061 mmol), p-biphenylmethyl bromide (80 mg, 0.31 mmol) and potassium carbonate (8.5 mg, 0.061 mmol) in acetone (0.6 mL) is stirred at room temperature overnight. The solvent is evaporated under reduced pressure. The residue is purified by a semi-preparative HPLC to give product as white solids. MS (ESI) m/z 495.2 [M+H]+

Example 6

5-methyl-7-(oxetan-2-ylmethyl)-3-(phenylamino)-2-(4-(pyridin-2-yl)benzyl)-2H-pyrazolo[3,4-d]pyrimidine-4,6(5H,7H)-dione

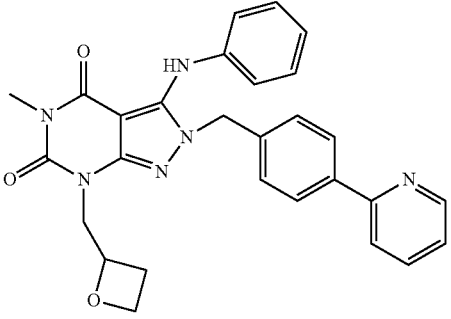 [SMILES: Cn1c(=O)c2c(Nc3ccccc3)n(Cc3ccc(-c4ccccn4)cc3)nc2n(CC2CCO2)c1=O]

The synthesis method is analogous to example 1 wherein 2-(iodomethyl)oxetane is used instead of isopropyl iodide. MS (ESI) m/z 495.2 [M+H]+

Example 7

7-isobutyl-5-methyl-3-(phenylamino)-2-(3-phenylprop-2-ynyl)-2H-pyrazolo[3,4-d]pyrimidine-4,6(5H,7H)-dione

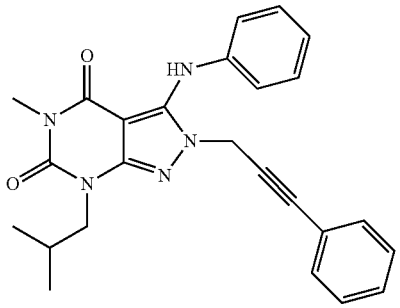 [SMILES: CC(C)Cn1c(=O)n(C)c(=O)c2c(Nc3ccccc3)n(CC#Cc3ccccc3)nc21]

A mixture of 7-isobutyl-5-methyl-3-(phenylamino)-2H-pyrazolo[3,4-d]pyrimidine-4,6(5H,7H)-dione (48.6 mg, 0.155 mmol), (3-bromoprop-1-ynyl)benzene (60.5 mg, 0.31 mmol) and potassium carbonate (42.8 mg, 0.31 mmol) in DMF (1.5 mL) is stirred at room temperature overnight. The mixture is filtered through a 0.45 μm microfilter and the filtrate is purified by a semi-preparative HPLC to give pure product as white solids. MS (ESI) m/z 428.2 [M+H]+.

Example 8

7-isobutyl-5-methyl-3-(phenylamino)-2-(4-(trifluoromethoxy)benzyl)-2H-pyrazolo[3,4-d]pyrimidine-4,6(5H,7H)-dione

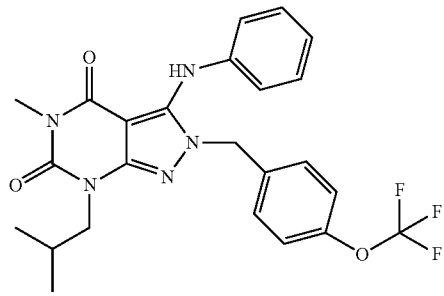 [SMILES: CC(C)Cn1c(=O)n(C)c(=O)c2c(Nc3ccccc3)n(Cc3ccc(OC(F)(F)F)cc3)nc21]

The synthesis method is analogous to example 7 wherein 1-(bromomethyl)-4-(trifluoromethoxy)benzene is used instead of (3-bromoprop-1-ynyl)benzene. MS (ESI) m/z 488.1 [M+H]+.

Example 9

(S)-2-(biphenyl-4-ylmethyl)-7-isobutyl-5-methyl-3-(pyrrolidin-3-ylamino)-2H-pyrazolo[3,4-d]pyrimidine-4,6(5H,7H)-dione

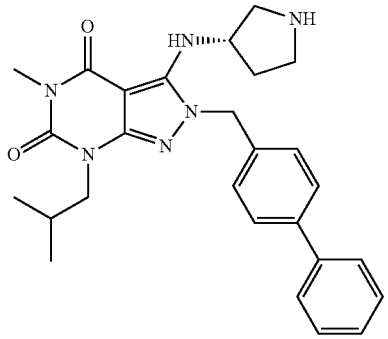 [SMILES: CC(C)Cn1c(=O)n(C)c(=O)c2c(N[C@H]3CCNC3)n(Cc3ccc(-c4ccccc4)cc3)nc21]

2-(biphenyl-4-ylmethyl)-3-chloro-7-isobutyl-5-methyl-2H-pyrazolo[3,4-d]pyrimidine-4,6(5H,7H)-dione (25 mg, 0.056 mmol) is dissolved in anhydrous and degassed THF, and then (S)-tert-butyl 3-aminopyrrolidine-1-carboxylate (64 mg, 0.34 mmol), Pd$_2$(dba)$_3$ (25 mg, 0.026 mmol) and Xantphos (16 mg, 0.026 mmol) are added, followed by $^t$BuOK (7.5 mg, 0.067 mmol). The reaction mixture is heated in microwave at 130° C. for 2.5 h. After cooling, solvent is removed. The residue is diluted with ethyl acetate (50 mL), and then washed with sodium carbonate aqueous solution three times. Solvent is removed under reduced pressure, the residue is treated with 50% TFA in CH$_2$Cl$_2$ (v/v) at room temperature for 6 hours. Evaporation to remove TFA and solvent, and the residue is purified by a semi-preparative HPLC to give pure product. MS (ESI) m/z 473.2 [M+H]+.

Example 10

2-(biphenyl-4-ylmethyl)-7-isobutyl-5-methyl-3-(pyridin-3-ylamino)-2H-pyrazolo[3,4-d]pyrimidine-4,6(5H,7H)-dione

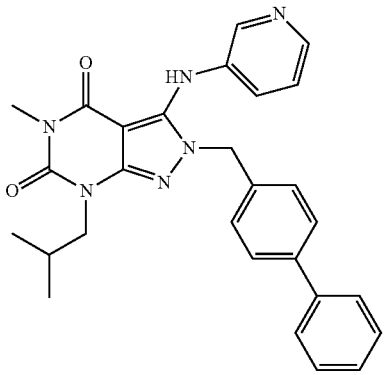 [SMILES: CC(C)Cn1c(=O)n(C)c(=O)c2c(Nc3cccnc3)n(Cc3ccc(-c4ccccc4)cc3)nc21]

The synthesis method is analogous to example 3 wherein 2-(biphenyl-4-ylmethyl)-3-chloro-7-isobutyl-5-methyl-2H-pyrazolo[3,4-d]pyrimidine-4,6(5H,7H)-dioneis is used instead of 2-(biphenyl-4-ylmethyl)-3-iodo-7-isobutyl-5-methyl-2H-pyrazolo[3,4-d]pyrimidine-4,6(5H,7H)-dione, and 3-pyridyl amine is added instead of 4-pyridyl amine. MS (ESI) m/z 481.2 [M+H]+.

Example 11

3-(1H-pyrazol-3-ylamino)-2-(biphenyl-4-ylmethyl)-7-isobutyl-5-methyl-2H-pyrazolo[3,4-d]pyrimidine-4,6(5H,7H)-dione

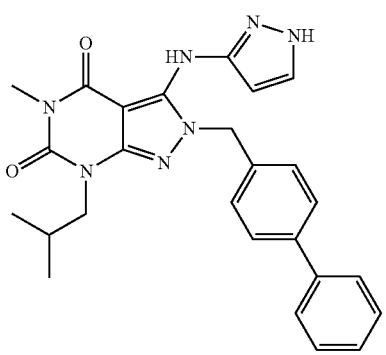 [SMILES: CC(C)Cn1c(=O)n(C)c(=O)c2c(Nc3cc[nH]n3)n(Cc3ccc(-c4ccccc4)cc3)nc21]

The synthesis method is analogous to example 3 wherein 2-(biphenyl-4-ylmethyl)-3-chloro-7-isobutyl-5-methyl-2H-pyrazolo[3,4-d]pyrimidine-4,6(5H,7H)-dioneis is used instead of 2-(biphenyl-4-ylmethyl)-3-iodo-7-isobutyl-5-methyl-2H-pyrazolo[3,4-d]pyrimidine-4,6(5H,7H)-dione, and 1H-pyrazol-3-amine is added instead of 4-pyridyl amine. MS (ESI) m/z 470.2 [M+H]+.

Example 12

5-methyl-3-(phenylamino)-2-(4-(pyridin-2-yl)benzyl)-7-(pyrrolidin-3-ylmethyl)-2H-pyrazolo[3,4-d]pyrimidine-4,6(5H,7H)-dione

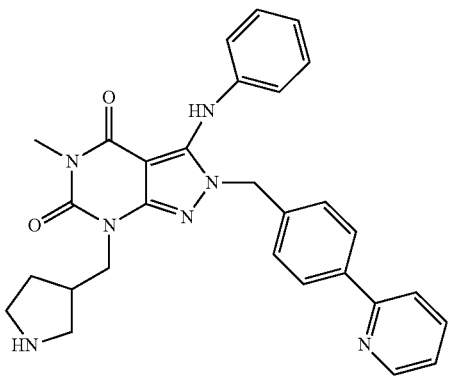 [SMILES: Cn1c(=O)c2c(Nc3ccccc3)n(Cc3ccc(-c4ccccn4)cc3)nc2n(CC2CCNC2)c1=O]

The synthesis method is analogous to example 1 wherein tert-butyl 3-(bromomethyl)pyrrolidine-1-carboxylate is used instead of isopropyl iodide. The obtained product is then deprotected by treating with 50% TFA in CH$_2$Cl$_2$ at room temperature to give the final product as white solids. MS (ESI) m/z 508.2 [M+H]+

Example 13

5-methyl-3-(phenylamino)-2-(4-(pyridin-2-yl)benzyl)-7-(pyrrolidin-2-ylmethyl)-2H-pyrazolo[3,4-d]pyrimidine-4,6(5H,7H)-dione

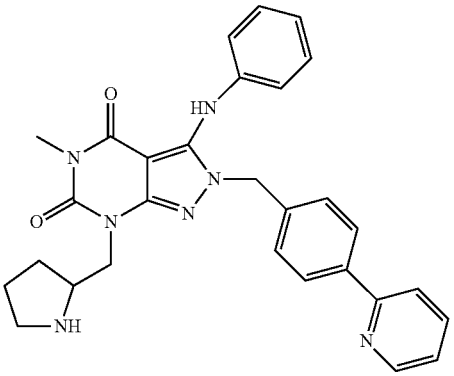 [SMILES: Cn1c(=O)c2c(Nc3ccccc3)n(Cc3ccc(-c4ccccn4)cc3)nc2n(CC2CCCN2)c1=O]

The synthesis method is analogous to example 12 wherein tert-butyl 2-(bromomethyl)pyrrolidine-1-carboxylate is used instead of tert-butyl 3-(bromomethyl)pyrrolidine-1-carboxylate. MS (ESI) m/z 508.2 [M+H]+.

Example 14

5-methyl-7-((1-methylpyrrolidin-2-yl)methyl)-3-(phenylamino)-2-(4-(pyridin-2-yl)benzyl)-2H-pyrazolo[3,4-d]pyrimidine-4,6(5H,7H)-dione

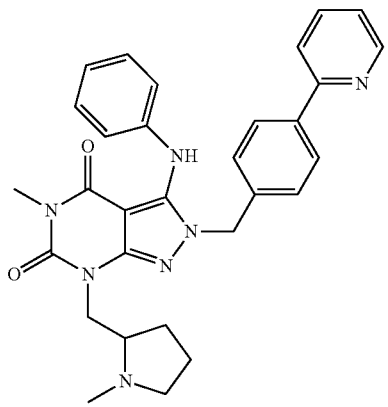 [SMILES: CN1CCCC1Cn1c(=O)n(C)c(=O)c2c(Nc3ccccc3)n(Cc3ccc(-c4ccccn4)cc3)nc21]

5-methyl-3-(phenylamino)-2-(4-(pyridin-2-yl)benzyl)-7-(pyrrolidin-2-ylmethyl)-2H-pyrazolo[3,4-d]pyrimidine-4,6(5H,7H)-dione is dissolved in CH$_3$OH (200 μL), and then 37% formaldehyde (2.3 μL) is added at room temperature. After 5 min, NaBH$_3$CN (1.8 mg, 0.028 mmol) in CH$_3$OH (100 μL) is added. The reaction mixture is stirred at r.t. for 30 min. The mixture is purified by HPLC to give pure product as white solids. MS (ESI) m/z 522.3 [M+H]+.

Example 15

7-isobutyl-5-methyl-3-(phenylamino)-2-(4-(pyrrolidin-1-ylmethyl)benzyl)-2H-pyrazolo[3,4-d]pyrimidine-4,6(5H,7H)-dione

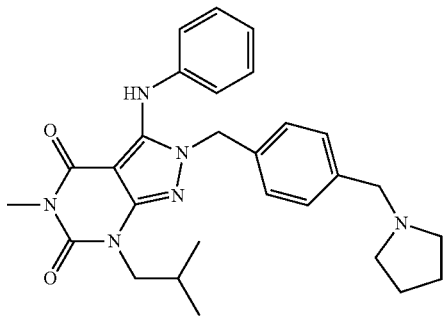 [SMILES: CC(C)Cn1c(=O)n(C)c(=O)c2c(Nc3ccccc3)n(Cc3ccc(CN4CCCC4)cc3)nc21]

(a) 2-(4-(bromomethyl)benzyl)-7-isobutyl-5-methyl-3-(phenylamino)-2H-pyrazolo[3,4-d]pyrimidine-4,6(5H,7H)-dione The synthesis method is analogous to example 7 wherein 1,4-bis(bromomethyl)benzene is used instead of (3-bromoprop-1-ynyl)benzene. MS (ESI) m/z 496.2 [M+H]+.

(b) 7-isobutyl-5-methyl-3-(phenylamino)-2-(4-(pyrrolidin-1-ylmethyl)benzyl)-2H-pyrazolo[3,4-d]pyrimidine-4,6(5H,7H)-dione 2-(4-(bromomethyl)benzyl)-7-isobutyl-5-methyl-3-(phenylamino)-2H-pyrazolo[3,4-d]pyrimidine-4,6(5H,7H)-dione (30 mg, 0.06 mmol), K₂CO₃ (16 mg, 0.12 mmol) and pyrrolidine (10 µL, 0.12 mmol) in THF is stirred at room temperature for 2 days. The mixture is then purified by HPLC to give final product as white powder. MS (ESI) m/z 487.3 [M+H]⁺.

Example 16

2-(4-(aminomethyl)benzyl)-7-isobutyl-5-methyl-3-(phenylamino)-2H-pyrazolo[3,4-d]pyrimidine-4,6(5H,7H)-dione

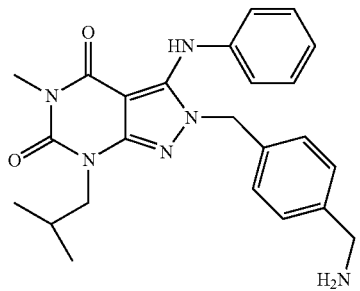 [SMILES: CC(C)Cn1c(=O)n(C)c(=O)c2c(Nc3ccccc3)n(Cc3ccc(CN)cc3)nc21]

The synthesis method is analogous to example 15 wherein ammonia is used in step (b) instead of pyrrolidine. MS (ESI) m/z 433.2 [M+H]⁺.

Example 17

7-isobutyl-2-(4-(((isobutylamino)methyl)benzyl)-5-methyl-3-(phenylamino)-2H-pyrazolo[3,4-d]pyrimidine-4,6(5H,7H)-dione

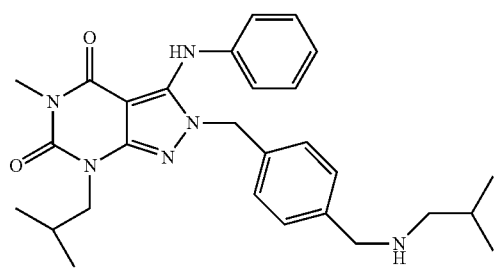 [SMILES: CC(C)CNCc1ccc(Cn2nc3c(c2Nc2ccccc2)c(=O)n(C)c(=O)n3CC(C)C)cc1]

The synthesis method is analogous to example 15 wherein 2-methylpropan-1-amine is used in step (b) instead of pyrrolidine. MS (ESI) m/z 489.3 [M+H]⁺.

Example 18

7-Isobutyl-5-methyl-3-(phenylamino)-2-(4-(piperidin-2-yl)benzyl)-2H-pyrazolo[3,4-d]pyrimidine-4,6(5H,7H)-dione

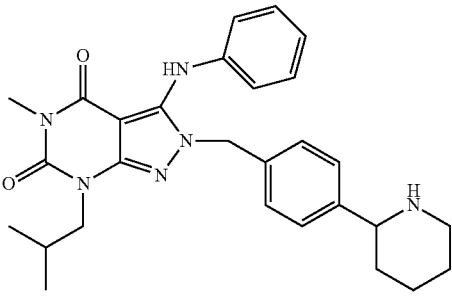 [SMILES: CC(C)Cn1c(=O)n(C)c(=O)c2c(Nc3ccccc3)n(Cc3ccc(C4CCCCN4)cc3)nc21]

(a) (4-(piperidin-2-yl)phenyl)methanol

To a suspension of LiAlH₄ (72 mg, 1.8 mmol) in 2 ml of anhydrous THF is added dropwise a solution of methyl 4-(piperidin-2-yl)benzoate hydrochloride (250 mg, 0.98 mmol) in THF at 0° C. The reaction mixture is stirred at room temperature for 4 hours, and is then carefully quenched with water at 0° C. After filtration, the filtrate is evaporated to dryness to give 187 mg of crude product as white solids, which is used for the next reaction without further purification. MS (ESI) m/z 192.1 [M+H]⁺.

(b) tert-butyl 2-(4-(hydroxymethyl)phenyl)piperidine-1-carboxylate

Crude (4-(piperidin-2-yl)phenyl)methanol (187 mg) is dissolved in 3 mL of DMF, and then Boc anhydride is added. The mixture is stirred at room temperature for 3 hours, and then purified by basic alumina column chromatography to give 200 mg of product as clear oil with a 70% overall yield.

(c) tert-butyl 2-(4-((7-isobutyl-5-methyl-4,6-dioxo-3-(phenylamino)-4,5,6,7-tetrahydropyrazolo[3,4-d]pyrimidin-2-yl)methyl)phenyl)piperidine-1-carboxylate tert-butyl 2-(4-(hydroxymethyl)phenyl)piperidine-1-carboxylate (47 mg, 0.16 mmol) is dissolved in 1 mL of anhydrous THF, and then triphenylphosphine (42 mg, 0.16 mmol) is added, followed by 7-isobutyl-5-methyl-3-(phenylamino)-2H-pyrazolo[3,4-d]pyrimidine-4,6(5H,7H)-dione (50 mg, 0.16 mmol). The mixture is cooled to −78° C., and then DIAD (95%, 50 µL) is added slowly. After the reaction is complete, the mixture is purified on a basic alumina column to give 76 mg of product (yield: 81%). MS (ESI) m/z 587.3 [M+H]⁺.

(d) 7-isobutyl-5-methyl-3-(phenylamino)-2-(4-(piperidin-2-yl)benzyl)-2H-pyrazolo[3,4-d]pyrimidine-4,6(5H,7H)-dione tert-butyl 2-(4-((7-isobutyl-5-methyl-4,6-dioxo-3-(phenylamino)-4,5,6,7-tetrahydropyrazolo[3,4-d]pyrimidin-2-yl)methyl)phenyl)piperidine-1-carboxylate (76 mg) is dissolved in 2 mL of dichloromethane, and then TFA (2 mL) is added.

The mixture is stirred at room temperature for an hour. After evaporation, the residue is purified by a semi-preparative HPLC to give 32 mg of pure product as white solids. MS (ESI) m/z 487.3 [M+H]$^+$.

Example 19

Measurement of PDE1B Inhibition In Vitro Using IMAP Phosphodiesterase Assay Kit

Phosphodiesterase 1B (PDE1B) is a calcium/calmodulin dependent phosphodiesterase enzyme that converts cyclic guanosine monophosphate (cGMP) to 5'-guanosine monophosphate (5'-GMP). PDE1B can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein—IMAP complex is large relative to cGMP-fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMP-fluorescein, which, when bound to IMAP, yields a large increase in fluorescence polarization (Δmp). Inhibition of phosphodiesterase, therefore, is detected as a decrease in Δmp.

Enzyme Assay

Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: 3',5'-cyclic-nucleotide-specific bovine brain phosphodiesterase (Sigma, St. Louis, Mo.) is reconstituted with 50% glycerol to 2.5 U/ml. One unit of enzyme will hydrolyze 1.0 μmole of 3',5'-cAMP to 5'-AMP per min at pH 7.5 at 30° C. One part enzyme is added to 1999 parts reaction buffer (30 μM CaCl$_2$, 10 U/ml of calmodulin (Sigma P2277), 10 mM Tris-HCl pH 7.2, 10 mM MgCl$_2$, 0.1% BSA, 0.05% NaN$_3$) to yield a final concentration of 1.25 mU/ml. 99 μl of diluted enzyme solution is added into each well in a flat bottom 96-well polystyrene plate to which 1 μl of test compound dissolved in 100% DMSO is added. The compounds are mixed and pre-incubated with the enzyme for 10 min at room temperature.

The FL-GMP conversion reaction is initiated by combining 4 parts enzyme and inhibitor mix with 1 part substrate solution (0.225 μM) in a 384-well microtiter plate. The reaction is incubated in dark at room temperature for 15 min. The reaction is halted by addition of 60 μl of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (Δmp).

A decrease in GMP concentration, measured as decreased Δmp, is indicative of inhibition of PDE activity. IC$_{50}$ values are determined by measuring enzyme activity in the presence of 8 to 16 concentrations of compound ranging from 0.0037 nM to 80,000 nM and then plotting drug concentration versus ΔmP, which allows IC$_{50}$ values to be estimated using nonlinear regression software (XLFit; IDBS, Cambridge, Mass.).

The Compounds of the Invention are selected and tested in this assay or in similar assay for PDE1 inhibitory activity. The Compounds of the Invention, e.g., compounds of formula 5.22 are shown to have an IC$_{50}$ of generally less than 250 nM.

Example 19

PDE1 Inhibitor Effect on Sexual Response in Female Rats

The effect of PDE1 inhibitors on Lordosis Response in female rats is measured as described in Mani, et al., Science (2000) 287: 1053. Ovariectomized and cannulated wild-type rats are primed with 2 μg estrogen followed 24 hours later by intracerebroventricular (icv) injection of progesterone (2 μg), PDE1 inhibitors of the present invention (0.1 mg, 1.0 mg or 2.5 mg) or sesame oil vehicle (control). The rats are tested for lordosis response in the presence of male rats. Lordosis response is quantified by the lordosis quotient (LQ=number of lordosis/10 mounts×100). It will be observed that the LQ for estrogen-primed female rats receiving Compounds of the Invention will be similar to estrogen-primed rats receiving progesterone and higher than for estrogen-primed rats receiving vehicle.

What is claimed is:
1. A compound of formula Q:

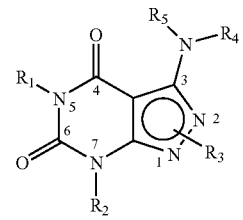

Formula Q wherein
(i) R$_1$ is H or C$_{1-6}$alkyl;
(ii) R$_2$ is
H,
C$_{1-6}$alkyl,
C$_{3-8}$cycloalkyl optionally substituted with one or more amino,
C$_{3-8}$heterocycloalkyl optionally substituted with C$_{1-6}$alkyl,
C$_{3-8}$cycloalkyl-C$_{1-6}$alkyl,
C$_{1-6}$haloalkyl,
C$_{0-6}$alkylaminoC$_{0-6}$alkyl,
hydroxyC$_{1-6}$alkyl,
arylC$_{0-6}$alkyl,
heteroarylalkyl,
C$_{1-6}$alkoxyarylC$_{1-6}$alkyl, or
-G-J wherein:
G is a single bond or, alkylene;
J is cycloalkyl or heterocycloalkyl optionally substituted with alkyl;

(iii) $R_3$ is
a) -D-E-F wherein
1. D is single bond, $C_{1-6}$alkylene or aryl$C_{1-6}$alkylene;
2. E is a $C_{1-6}$alkylene, arylene, $C_{1-6}$alkylarylene, amino$C_{1-6}$alkylene or amino; and
3. F is hetero$C_{3-8}$cycloalkyl substituted with $C_{1-6}$alkyl or F is pyrrolidin-1-yl, pyrrolidin-2-yl or piperidin-2-yl;
(iv) $R_4$ is aryl optionally substituted with one or more halo, hydroxy or $C_{1-6}$alkoxy; heteroaryl; or hetero$C_{3-6}$cycloalkyl; and
(v) $R_5$ is H, $C_{1-6}$alkyl, $C_{3-8}$cycloalkyl, heteroaryl, aryl or p-benzylaryl;

in free or salt form.

2. The compound according to claim 1, wherein said compound is a compound of formula Q-I

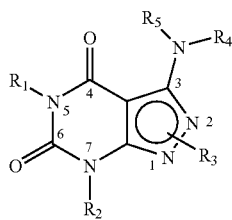

Formula Q-I wherein
(i) $R_1$ is H or $C_{1-6}$alkyl;
(ii) $R_2$ is H, $C_{1-6}$alkyl, $C_{3-8}$cycloalkyl, $C_{1-6}$haloalkyl, $C_{1-6}$alkylamino $C_{1-6}$alkyl, hydroxy $C_{1-6}$alkyl, aryl $C_{1-6}$alkyl, heteroarylalkyl, or $C_{1-6}$alkoxyaryl $C_{1-6}$alkyl;
(iii) $R_3$ is -D-E-F wherein
1. D is single bond, $C_{1-6}$alkylene, or aryl$C_{1-6}$alkylene;
2. E is a $C_{1-6}$alkylene, arylene, $C_{1-6}$alkylarylene, amino$C_{1-6}$alkylene or amino; and
3. F is selected from a group consisted of piperidinyl, pyrrolidin-2-yl, 1-methylpyrrolidin-2-yl, 1-methylpiperidin-2-yl and 1-ethylpiperidin-2-yl;
(iv) $R_4$ is aryl, heteroaryl or heterocyclo$C_{3-6}$alkyl; and
(v) $R_5$ is H, $C_{1-6}$alkyl, $C_{3-8}$cycloalkyl, heteroaryl, aryl, p-benzylaryl;

in free or salt form.

3. The compound according to claim 1, wherein said compound is a compound of formula Q-II:

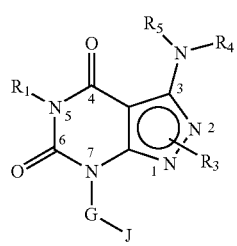

Formula Q-II wherein
(i) $R_1$ is H or $C_{1-6}$alkyl;
(ii) -G-J is
$C_{3-8}$heterocycloalkyl optionally substituted with $C_{1-6}$alkyl,
or $C_{3-8}$cycloalkyl-$C_{1-6}$alkyl;

(iv) $R_3$ is
a) -D-E-F wherein
1. D is single bond, $C_{1-6}$alkylene, or aryl$C_{1-6}$alkylene;
2. E is a $C_{1-6}$alkylene, arylene, $C_{1-6}$alkylarylene, amino$C_{1-6}$alkylene or amino; and
3. F is selected from a group consisted of piperidinyl, pyrrolidin-2-yl, 1-methylpyrrolidin-2-yl, 1-methylpiperidin-2-yl and 1-ethylpiperidin-2-yl;
(v) $R_4$ is aryl optionally substituted with one or more halo or hydroxy; heteroaryl; or hetero$C_{3-6}$cycloalkyl; and
(vi) $R_5$ is H, $C_{1-6}$alkyl, $C_{3-8}$cycloalkyl, heteroaryl, aryl, p-benzylaryl, in free or salt form.

4. The compound according to claim 1, wherein said compound is a compound of formula Q-III:

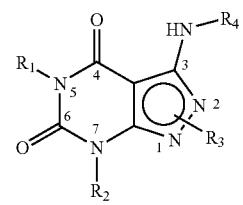

Formula Q-III wherein
(i) $R_1$ is H or $C_{1-6}$alkyl;
(ii) $R_2$ is $C_{1-6}$alkyl;
(iii) $R_3$ is -D-E-F wherein
1. D is single bond, $C_{1-6}$alkylene or aryl$C_{1-6}$alkylene;
2. E is a $C_{1-6}$alkylene, arylene, $C_{1-6}$alkylarylene, amino$C_{1-6}$alkylene or amino; and
3. F is selected from a group consisted of piperidinyl, pyrrolidin-2-yl, 1-methylpyrrolidin-2-yl, 1-methylpiperidin-2-yl and 1-ethylpiperidin-2-yl;
(iv) $R_4$ is aryl optionally substituted with one or more halo, hydroxy or $C_{1-6}$alkoxy; heteroaryl; or hetero$C_{3-6}$cycloalkyl;

in free or salt form.

5. The compound according to claim 1, wherein D is a methylene, in free or salt form.

6. The compound according to claim 5, wherein E is phenylene, in free or salt form.

7. The compound according to claim 6, wherein F is 1-methylpyrrolidin-2-yl or 1-methylpiperidin-2-yl, in free or salt form.

8. The compound according to claim 7, wherein $R_2$ is $C_{1-6}$alkyl, in free or salt form.

9. The compound according to claim 8, wherein $R_4$ is phenyl optionally substituted with one or more halo, hydroxy or $C_{1-6}$alkoxy, in free or salt form.

10. The compound according to claim 9, wherein $R_5$ is H, in free or salt form.

11. A compound according to claim 1 selected from the following:

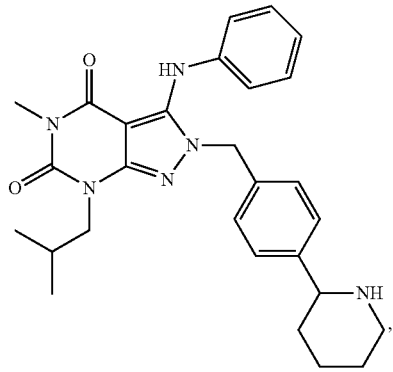

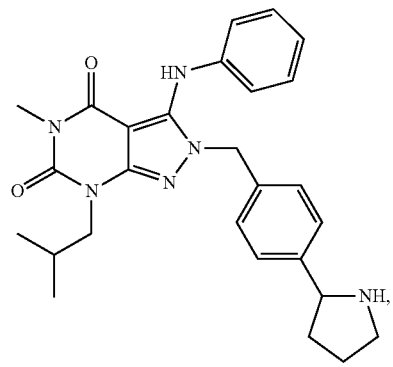

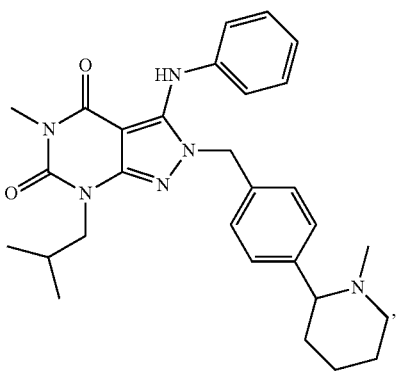

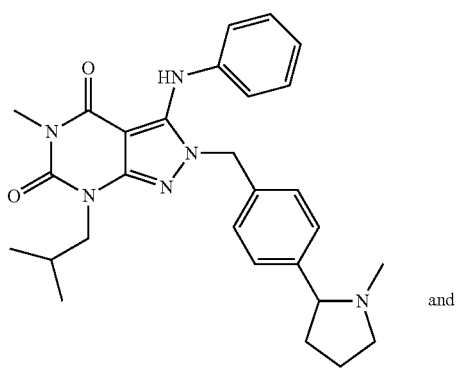
and

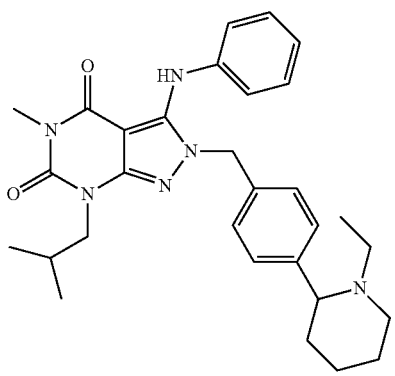 [SMILES: CCN1CCCCC1c1ccc(Cn2nc3c(c2Nc2ccccc2)c(=O)n(C)c(=O)n3CC(C)C)cc1]

in free or salt form.

12. A pharmaceutical composition comprising a compound according 1, in free or pharmaceutically acceptable salt form, in admixture with a pharmaceutically acceptable diluent or carrier.

13. A method for the treatment of diseases involving disorders of the dopamine D1 receptor intracellular pathway, wherein treatment embraces amelioration of symptoms or causes of diseases, comprising administering a therapeutically effective amount of a PDE 1 Inhibitor according to claim 1, in free or pharmaceutically acceptable salt form, to a person in need thereof.

14. The method according to claim 13, wherein said disease is any of the following: Parkinson's disease, depression, attention deficit disorder, attention deficit hyperactivity disorder, stroke, hypertension, pulmonary hypertension and female sexual dysfunction.

15. The method of claim 13, wherein the condition is Parkinson's disease.

16. The method of claim 13, wherein said condition is female sexual dysfunction.

17. A method of making a compound according to claim 1 wherein $R_5$ is H, comprising reacting a pyrazolo[3,4-d]pyrimidine-4,6(5H,7H)-dione of Formula IIIC:

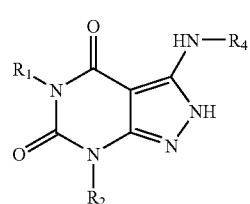

(IIIc)

with a compound of formula X—$R_3$, wherein X is a leaving group and $R_1$, $R_2$, $R_3$ and $R_4$ are as described in claim 1, and isolating the compound thus obtained.

18. A method of making a compound according to claim 1 wherein $R_5$ is H, comprising reacting a pyrazolo[3,4-d]pyrimidine-4,6(5H or 7H)-dione of Formula IIh:

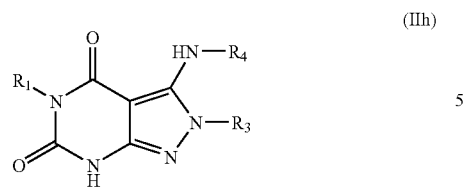 (IIh)

with a compound of formula X—$R_2$ wherein X is a leaving group and $R_1$, $R_2$, $R_3$ and $R_4$ are as defined in claim 1 wherein $R_5$ is H and isolating the compound thus obtained.

19. The compound according to claim 7, wherein $R_2$ is $C_{1-6}$alkyl, in free or salt form.

20. The compound according to claim 19, wherein $R_4$ is phenyl optionally substituted with one or more halo, hydroxy or $C_{1-6}$alkoxy; and $R_5$ is H, in free or salt form.

* * * * *

UNITED STATES PATENT AND TRADEMARK OFFICE
CERTIFICATE OF CORRECTION

PATENT NO. : 8,846,693 B2  
APPLICATION NO. : 12/746231  
DATED : September 30, 2014  
INVENTOR(S) : Peng Li et al.

Page 1 of 1

It is certified that error appears in the above-identified patent and that said Letters Patent is hereby corrected as shown below:

In the Claims

Column 72, line 22, claim 12, "according 1" should be changed to "according to claim 1".

Column 72, line 66-67, claim 18, "pyrazolo[3,4-d]pyrimidine-4,6(5H or 7H)-dione" should be changed to "pyrazolo[3,4-d]pyrimidine-4,6(5H,7H)-dione".

Signed and Sealed this  
Thirty-first Day of March, 2015

Michelle K. Lee  
*Director of the United States Patent and Trademark Office*